United States Patent
Wong et al.

(10) Patent No.: US 12,318,485 B2
(45) Date of Patent: Jun. 3, 2025

(54) METHODS AND COMPOSITIONS FOR TARGETED DELIVERY BY POLYMERSOMES

(71) Applicant: Rock BioMedical Inc., Taipei (TW)

(72) Inventors: Chi-Huey Wong, Rancho Santa Fe, CA (US); Jeng Shin Lee, Lincoln, MA (US); Chen-Yo Fan, Taipei (TW); Szu-Wen Wang, Taipei (TW)

(73) Assignee: ROCK BIOMEDICAL, INC., Taipei (TW)

( * ) Notice: Subject to any disclaimer, the term of this patent is extended or adjusted under 35 U.S.C. 154(b) by 0 days.

(21) Appl. No.: 18/629,675

(22) Filed: Apr. 8, 2024

(65) Prior Publication Data

US 2025/0041222 A1 Feb. 6, 2025

Related U.S. Application Data

(60) Provisional application No. 63/575,056, filed on Apr. 5, 2024, provisional application No. 63/587,231, filed on Oct. 2, 2023, provisional application No. 63/458,102, filed on Apr. 8, 2023.

(51) Int. Cl.
| | | |
|---|---|---|
| A61K 9/1273 | (2025.01) | |
| A61K 45/06 | (2006.01) | |
| C12N 15/88 | (2006.01) | |

(52) U.S. Cl.
CPC ............ *A61K 9/1273* (2013.01); *A61K 45/06* (2013.01); *C12N 15/88* (2013.01)

(58) Field of Classification Search
None
See application file for complete search history.

(56) References Cited

U.S. PATENT DOCUMENTS

| | | |
|---|---|---|
| 7,871,626 B2 | 1/2011 | Hoffmann et al. |
| 10,301,377 B2 | 5/2019 | Graham et al. |
| 10,906,944 B2 | 2/2021 | He et al. |
| 10,953,089 B1 | 3/2021 | Smith et al. |
| 10,954,289 B1 | 3/2021 | Babb et al. |
| 11,480,391 B2 | 10/2022 | Wong et al. |
| 11,866,485 B2 | 1/2024 | Lin et al. |
| 11,918,641 B2 | 3/2024 | Wong et al. |

(Continued)

FOREIGN PATENT DOCUMENTS

| | | |
|---|---|---|
| CN | 105934441 A | 9/2016 |
| CN | 112626124 A | 4/2021 |

(Continued)

OTHER PUBLICATIONS

Zhang et al. Adv Mater. 29, 1702311 (Year: 2017).*

(Continued)

*Primary Examiner* — Mark S Kaucher
(74) *Attorney, Agent, or Firm* — Prosyla Group PC

(57) ABSTRACT

The present disclosure relates to a copolymer and a polymersome for targeted delivery of biomolecules to a living organism. The exemplary copolymer comprises an initiator block, a propagator block, and a linkage connecting the initiator block and the propagator block. The initiator block comprises a glycan head configured to provide a targeted delivery, and the propagator block comprises a functional moiety configured to provide desired properties for the polymersome.

122 Claims, 9 Drawing Sheets

(56) References Cited

U.S. PATENT DOCUMENTS

| | | | |
|---|---|---|---|
| 12,085,340 | B2 | 9/2024 | Wong et al. |
| 2006/0073542 | A1 | 4/2006 | Bayer et al. |
| 2010/0041740 | A1 | 2/2010 | Wong et al. |
| 2010/0247571 | A1 | 9/2010 | Wong et al. |
| 2013/0309176 | A1 | 11/2013 | Port et al. |
| 2014/0107049 | A1 | 4/2014 | Bennani et al. |
| 2015/0132330 | A1 | 5/2015 | Garcia-Sastre et al. |
| 2016/0199481 | A1 | 7/2016 | Bloom |
| 2016/0376321 | A1 | 12/2016 | Hotez et al. |
| 2018/0043007 | A1 | 2/2018 | LeFebvre et al. |
| 2019/0388460 | A1 | 12/2019 | Hedrick et al. |
| 2020/0046826 | A1 | 2/2020 | Wong et al. |
| 2020/0078452 | A1 | 3/2020 | Wong et al. |
| 2020/0079808 | A1 | 3/2020 | Pfister et al. |
| 2020/0231633 | A1 | 7/2020 | Berman et al. |
| 2020/0283743 | A1 | 9/2020 | Zhang et al. |
| 2021/0017563 | A1 | 1/2021 | Bhatnagar et al. |
| 2021/0207106 | A1 | 7/2021 | Anthony et al. |
| 2021/0316002 | A1 | 10/2021 | Ellis |
| 2022/0233713 | A1 | 7/2022 | Callan et al. |
| 2023/0000741 | A1 | 3/2023 | Wong et al. |
| 2023/0074185 | A1 | 3/2023 | Wong et al. |
| 2023/0105209 | A1 | 4/2023 | Lin et al. |
| 2023/0002790 | A1 | 9/2023 | Lin et al. |
| 2023/0279080 | A1 | 9/2023 | Lin et al. |
| 2023/0302114 | A1 | 9/2023 | Wong |
| 2024/0016917 | A1 | 1/2024 | Ma et al. |
| 2024/0066113 | A1 | 2/2024 | Wong et al. |
| 2024/0100147 | A1 | 3/2024 | Wong et al. |
| 2024/0228591 | A1 | 7/2024 | Lin et al. |

FOREIGN PATENT DOCUMENTS

| | | | | |
|---|---|---|---|---|
| CN | 116478948 | A | 7/2023 | |
| EP | 1987068 | A1 | 11/2008 | |
| EP | 2949665 | A1 | 12/2015 | |
| JP | 2012530499 | A | 12/2012 | |
| JP | 2017518989 | A | 7/2017 | |
| RU | 2720614 | C1 | 5/2020 | |
| RU | 2730897 | C1 | 8/2020 | |
| WO | 2004099240 | A2 | 11/2004 | |
| WO | 2004099240 | A3 | 11/2004 | |
| WO | 2007008918 | A2 | 1/2007 | |
| WO | 2007095506 | A1 | 8/2007 | |
| WO | 2009002516 | A1 | 12/2008 | |
| WO | 2009007427 | A2 | 1/2009 | |
| WO | 2010022737 | A1 | 3/2010 | |
| WO | 2010111687 | A2 | 9/2010 | |
| WO | 2010148511 | A1 | 12/2010 | |
| WO | WO-2011115862 | A1 * | 9/2011 | ............ A61K 45/06 |
| WO | 2012054907 | A2 | 4/2012 | |
| WO | 2012088428 | A1 | 6/2012 | |
| WO | 2013043729 | A1 | 3/2013 | |
| WO | 2013067652 | A1 | 5/2013 | |
| WO | 2014115797 | A1 | 7/2014 | |
| WO | 2015057942 | A1 | 4/2015 | |
| WO | 2015073727 | A1 | 5/2015 | |
| WO | 2015176662 | A1 | 11/2015 | |
| WO | 2015184004 | A1 | 12/2015 | |
| WO | 2017062496 | A2 | 4/2017 | |
| WO | WO2017081082 | A2 | 5/2017 | |
| WO | 2018089407 | | 11/2017 | |
| WO | 2018089407 | A1 | 5/2018 | |
| WO | 2019028190 | A1 | 2/2019 | |
| WO | 2015028478 | A1 | 6/2019 | |
| WO | 2019246363 | A1 | 12/2019 | |
| WO | 2020011275 | A1 | 1/2020 | |
| WO | 2020058239 | A1 | 3/2020 | |
| WO | 2019246363 | | 4/2020 | |
| WO | 2020172072 | A1 | 8/2020 | |
| WO | 2020198865 | A1 | 10/2020 | |
| WO | WO2020205034 | A1 | 10/2020 | |
| WO | 2021019102 | A2 | 2/2021 | |
| WO | 2021035325 | A1 | 3/2021 | |
| WO | 2021045632 | A1 | 3/2021 | |
| WO | 2021045836 | A1 | 3/2021 | |
| WO | 2021174128 | A1 | 9/2021 | |
| WO | 2021180602 | A1 | 9/2021 | |
| WO | 2021183195 | A1 | 9/2021 | |
| WO | 2021186028 | A1 | 9/2021 | |
| WO | 2021214204 | A1 | 10/2021 | |
| WO | 2021219897 | A1 | 11/2021 | |
| WO | 2021226533 | A1 | 11/2021 | |
| WO | 2021233989 | A1 | 11/2021 | |
| WO | 2021257586 | A1 | 12/2021 | |
| WO | WO-2022047401 | A1 * | 3/2022 | ............ A61K 45/06 |
| WO | 2022221835 | A2 | 10/2022 | |
| WO | 2022221837 | A2 | 10/2022 | |
| WO | 2022229854 | A1 | 11/2022 | |
| WO | WO-2022227927 | A1 * | 11/2022 | ............ C08G 75/00 |
| WO | PCTUS2282428 | | 12/2022 | |
| WO | 2023021111 | A1 | 2/2023 | |
| WO | 2023056482 | A1 | 4/2023 | |
| WO | 2023069551 | A1 | 4/2023 | |
| WO | 2023129928 | A2 | 7/2023 | |

OTHER PUBLICATIONS

Bang et al. J. Am. Chem. Soc. 135, 2088-2091 (Year: 2013).*
Chuard et al. Org. Biomol. Chem. 13, 64-67 (Year: 2015).*
Levit et al. Polymers 12, 183 (Year: 2020).*
Zhang et al. Biomacromolecules, 23, 1-19 (Year: 2022).*
Sun et al., "N-Linked Glycosylation of the Hemagglutinin Protein Influences Virulence and Antigenicity of the 1918 Pandemic and Seasonal H1N1 Influenza A Viruses", 2013, Journal of Virology, vol. 87, No. 15, pp. 8756-8766.
Tai, Wanbo et al., "Characterization of the receptor-binding domain (RBD) of 2019 novel coronavirus: implication for development of RBD protein as a viral attachment inhibitor and vaccine," Cell Mol Immunol. Jun. 2020; 17(6):613-620 https://pubmed.ncbi.nlm.nih.gov/32203189/.
Tian, Jing-Hui et al., "SARS-COV-2 spike glycoprotein vaccine candidate NVX-CoV2373 immunogenicity in baboons and protection in mice," Nature Communications, 2021, 14 pages. Downloaded Sep. 27, 2023: https://doi.org/10.1038/s41467-020-20653-8.
Torres-Vanegas, Julian D., "Delivery Systems for Nucleic Acids and Proteins: Barriers, Cell Capture Pathways and Nanocarriers," Pharmaceutics, vol. 13, No. 3, Mar. 22, 2021, pp. 428.
Vogel, Annette B. et al. "BNT162b vaccines protect rhesus macaques from SARS-COV-2," Nature, vol. 592, Feb. 1, 2021, pp. 283-289.
Watanabe, Yasunori et al., "Exploitation of glycosylation in enveloped virus pathobiology," BBA—General Subjects 1863, 2019), pp. 1480-1497.
Watanabe, Yasunori et al., "Site-specific glycan analysis of the SARS-COV-2 spike," Science, Jul. 2020, vol. 369, pp. 330-333.
Weissman, Drew et al., "D614G Spike Mutation Increases Sars COV-2 Susceptibility to Neutralization," Cell Host & Microbe, Jan. 13, 2021, vol. 29, pp. 23-31 (e1-e4).
Wu, Chung-Yi et al., "Influenza A surface glycosylation and vaccine design", PNAS, Jan. 2017, (Epub Dec. 27, 2016), vol. 114, No. 2, pp. 280-285.
Yang, Zhiwei et al., "Mutation effects of neuraminidases and their docking with ligands: a molecular dynamics and free energy calculation study", J Comput Aided Mol Des, 27: 935-950, 2013.
Zaraket, Hassan et al., "Full Genome Characterization of Human Influenza A/H3N2 Isolates from Asian Countries Reveals a Rare Amantadine Resistance-Conferring Mutation and Novel PB1-F2 Polymorphisms", Frontiers in Microbiology, vol. 7, Article 262, Mar. 2016.
Zhang, Xiaojian et al., "Role of stem glycans attached haemagglutinin in the biological characteristics of H5N1 avian influenza virus", Journal of General Virology, 96, 1248-1257, 2015.
Zhang, Yan et al., "Glycosylation on Hemagglutinin Affects the Virulence and Pathogenicity of Pandemic H1N1/2009 Influenza A Virus in Mice", PLOS ONE, vol. 8, Issue 4, Apr. 2013.
Zhao, "Glycans of SARS-COV-2 Spike Protein in Virus Infection and Antibody Production", Frontiers in Molecular Biosciences, Apr. 13, 2021; Entire Document; DOI: 10.3389/fmolb.2021.629873.

(56) References Cited

OTHER PUBLICATIONS

Zheng, J. et al., "Identification of N-linked glycosylation sites in the spike protein and their functional impact on the replication and infectivity of coronavirus infectious bronchitis virus in cell culture", Virology, Oct. 13, 2017, vol. 513, pp. 65-74; abstract; p. 65, 1st column, second paragraph; p. 66, column 5th paragraph; p. 68, first column, first, third paragraphs; Table 3; figure 5; http://dx.doi.org/10.1016/j.virol.2017.10.003.
Bernstein, David et al., "Immunogenicity of chimeric haemagglutinin-based, universal influenza virus vaccine candidates: interim results of a randomized, placebo-controlled, phase 1 clinical trial", The Lancet Infectious Disease, Elsevier, Amerstdam, NL, vol. 20, No. 1, Oct. 17, 2019, pp. 80-91, XP085982810. ISSN: 1473-3099, DOI: 10.1016/S1473-3099(19)30393-7.
Bosch, Berend Jan et al., "Coronavirus Escape from Heptad Repeat 2 (HR2)-Derived Peptide Entry Inhibition as a Result of Mutations in the HR1 Domain of the Spike Fusion Protein," J of Virol., Mar. 2008, vol. 82, No. 5, pp. 2580-2585.
Cao, Yiwei et al., "Dynamic Interactions of Fully Glycosylated SARS-COV-2 Spike Protein with Various Antibodies," JCTC, Sep. 16, 2021, vol. 17, pp. 6559-6569.
Castrucci, M.R. et al., "Biologic importance of neuramindase stalk length in influenza A virus", Journal of Virology, 1993, vol. 67, No. 2, pp. 759-764.
Chokhawala, H.A. et al., "Enzymatic Synthesis of Fluorinated Mechanistic Proves for Sialidases and Sialyltransferases", J.Am. Chem. Soc., 2007, p. 10630; scheme 1.
Dang, Juanjuan et al., "Multivalency-assisted membrane-penetrating siRNA delivery sensitizes photothermal ablation via inhibition of tumor glycolysis metabolism," Biomaterials, vol. 223, Dec. 2019, 119463.
Davies, Nicholas G. et al., "Estimated transmissibility and impact of SARS-COV-2 lineage B. 1.1.7 in England," Science, Apr. 2021, vol. 372, p. 149 (10 pages).
Dowling, W. et al., "Influences of Glycosylation on Antigenicity, Immunogenicity, and Protective Efficacy of Ebola Virus GP DNA Vaccines", J. of Virology, 2007, vol. 81, No. 4, pp. 1821-1837, p. 1822, second column, fourth paragraph; p. 1823, second column, third paragraph; doi:10.1128/JVI.02098-06.
Edwards, et al., "The Remarkable Flexibility of the Human Antibody Repertoire; Isolation of Over One Thousand Different Antibodies to a Single Protein, BLyS," J. Mol. Biol., Nov. 2003, 14:334(1):103-18; doi: 10.1016/jmb.2003.09.054. PMID 14596803.
Feng et al., "A Glycolipid Adjuvant, 7DW8-5, Enhances the Protective Immune Response to the Current Slpit Influenza Vaccine in Mice", Frontiers in Microbiology, Sep. 18, 2019, vol. 10, No. 2157M, pp. 1-9; abstract.
Focosi, Daniele, "Neutralising antibody escape of SARS-COV-2 spike protein: Risk assessment for antibody-based Covid-19 therapeutics and vaccines," Rev. Med Virol., 2021, vol. 31, 21 pages. e2231.
Galili, "Amplifying immunogenicity of prospective Covid-19 vaccines by glycoengineering the coronavirus glycan-shield to present alpha-gal epitopes", Vaccine, Aug. 19, 2020; abstract; Fig. 1; DOI: 10.1016/j.vaccine.2020.08032.
Galili, Uri, "Amplifying immunogenicity of prospective Covid-19 vaccines by glycoengineering the coronavirus glycan-shield to present [alpha]-gal epitopes," Vaccine, 2020, vol. 38, pp. 6487-6499.
Galili, Uri, "COVID-19 variants as moving targets and how to sop them by glycoengineered whole-virus vaccines," Virulence, 12:1, 1717-1720, DOI:10.1080/21505594.2021. 1939924. (https://doi.org/10.1080/21505594.2021.1939924).
GenBank Accession BCN86353.1 accessed on Jan. 22, 2021. https://www.ncbi.nlm.nih.gov/protein/BCN86353.1?report=genbank&log$=protalign&blast_rank=2&RID=EYKWWEAA016.
GenBank Accession CCH23214, haemagglutinin [Influenza A virus (A/WSN/1933(H1N1))], 2013.
GenBank accession MN908947.3, Mar. 18, 2020, 11 pages. (https://www.ncbi.nlm.nih.gov/nuccore/MN908947).
GenBank Accession, ACF54601, neuraminidase [Influenza A virus (A/WSN/1933(H1N1))], 2008.
GenBank Accession: QHD43416.1, (Mar. 18, 2020) [Described in the Office Action as Appendix A] (Year: 2020).
GenBank: QLB39105.1 accessed on Jan. 1, 2020. https://www.ncbi.nlm.nih.gov/protein/QLB39105.1?report=genbank&log$=protalign&blast_rank=1&RID=EYKWWEAA016.
GenBank: QTA38985.1 accessed Mar. 21, 2021. https://www.ncbi.nlm.nih.gov/protein/QTA38985.1?report=genbank&log$=protalign&blast_rank=3&RID=EYKWWWVEAA016.
Gillian, M. Air, "Influenza neuraminidase", Influenza and Other Respiratory Viruses, 2011.
Goel, Manisha et al., "Plasticity within the Antigen-Combining Site May Manifest as Molecular Mimicry in the Humoral Immune Response," J. Immunol., Dec. 15, 2004, 173(12):7358-67 PMID: 15585860 DOI: 10.4049/jimmunol.173.12.7358.
Hayashi, T. et al., "Stereospecific a-Sialylation by SIte-Selective Fluorination", Agnew. Chem. Int. Ed., Jan. 25, 2019, vol. 58, pp. 3814-3818. (Whole Document).
Huang et al., "Impact of glycosylation on SARS-COV-2 infection and broadly protective vaccine design," BioRxiv, May 25, 2021, DOI: https://doi.org/10.1101/2021.05.25.445523, internal pp. 1-48.
Hughes et al., "Adaptation of Influenza A Viruses to Cells Expressing Low Levels of Sialic Acid Leads to Loss of Neuraminidase Activity", Journal of Virology, 2001, vol. 75, No. 8, pp. 3766-3770.
International Search Report and Written Opinion issued on Jun. 22, 2023 in International Patent Application No. PCT/US22/82428.
Janeway Jr., Charles A et al., "Immunobiology: The Immune System in Health and Disease," 3rd edition, Garland Publishing Inc., 1997, pp. 3:1-3:11.
Kanyavuz, Alexia et al., "Breaking the law: unconventional strategies for antibody diversification," Nat Rev Immunol., Jun. 2019, 19(6):355-368. doi: 10.1038/S41577-019-0126-7. PMID: 30718829.
Lescar et al., "Crystal Structure of a Cross-reaction Complex between Fab F9.13.7 and Guinea Fowl Lysozyme," J Biol Chem., Jul. 1995, 270(30):18067-76. doi: 10.1074/jbc.270.30.18067. PMID: 7629116.
Li, et al., Glycosylation of Neuraminidase Determines the Neurovirulence of Influenza A/WSN/33 Virus, 1993, Journal of Virology, vol. 67, No. 11, pp. 6667-6673.
Liu, Wen-Chun et al., "Unmasking Stem-Specific Neutralizing Epitopes by Abolishing N-Linked Glycosylation Sites of Influenza Virus Hemagglutinin Proteins for Vaccine Design", Journal of Virology, vol. 90 No. 19, Oct. 2016.
Lloyd, C. et al., "Modelling the human immune response: performance of a 10(11) human antibody repertoire against a broad panel of therapeutically relevant antigens," Protein Engineering Design & Selection, 2009, vol. 22, No. 3, pp. 159-168. doi: 10.1093/protein/gzn058.
Lo, H.-J. et al., "Synthesis of Sialidase-Resistant Oligosaccharide and Antibody Glycoform Containing α2,6-Linked 3Fax-Neu5Ac", J. Am. Chem. Soc., Apr. 10, 2019, vol. 141, No. 16, pp. 6484-6488. (Whole Document.).
Lostalé-Seijo, Irene and Montenegro, Javier, "Synthetic materials at the forefront of gene delivery," Nature Reviews Chemistry, vol. 2, Sep. 21, 2018, pp. 258-277.
Magazine, Nicholas et al., "Mutations and Evolution of the SARS-COV-2 Spike Protein," Viruses, 2022, vol. 14, 640, 11 pgs.
Medina, Rafael A. et al., "Glycosylations in the globular head of the hemagglutinin protein modulate the virulence and antigenic properties of the H1N1 influenza viruses", Sci Transl Med., May 29, 2013.
Nobusawa et al., "Comparison of Complete Amino Acid Sequences and Receptor-Binding Properties among 13 Serotypes of Hemagglutinins of Influenza A Viruses", Virology, 182, 475-485 (1991).
Non-Final Office Action issued in U.S. Appl. No. 17/937,744 dated Jul. 5, 2023.
Office Action and Search Report issued in Taiwan Patent Application No. 111113933 on Mar. 26, 2024. English translation of search report.
Office Action issued in Taiwan Patent Application No. 111113932 on Oct. 16, 2023.

(56) References Cited

OTHER PUBLICATIONS

Office Action issued on Nov. 14, 2022, in Israel Patent Application No. 293502.
Official Action, dated Aug. 31, 2023, received in Russia Patent Application No. 2023100504. English translation provided.
Okamoto, K. et al., "An effective synthesis of α-glycosides of N-acetylneuraminic acid by use of 2β-halo-3β-hydroxy-4,7,8,9-tetra-O-acetyl-N-acetylneuraminic acid methyl ester", Tetrahedron Letters, 1986, vol. 27, No. 43, pp. 5233-5236.
Rahman, M Shaminur et al., "Epitope-based chimeric peptide vaccine design against S, M, and E proteins of SARS-CoV-2, the etiologic agent of COVID-19 pandemic, an in silico approach", PeerJ, Jul. 27, 2020 (publication date), DOI 10.7717/peerj.9572, Internal pp. 1-30, Supplemental Information pp. 1, 2. Abstract; and supplemental information pp. 1, 2.
Rees-Spear, Chloe et al., "The effect of spike mutations on SARS-COV-2 neutralization," Cell Rep., Mar. 2023, 34(12): 108890. Published online Mar. 6, 2021. doi: 10.1016/j.celrep.2021.108890: 10.1016/j.celrep.2021.108890 PMCID: PMC7936541 PMID: 33713594.
Roberts, Paul C. et al., "Role of Conserved Glycosylation Sites in Maturation and Transport of Influenza A Virus Hemagglutinin", Journal of Virology, Jun. 1993, p. 3048-3060.
Rudikoff et al., "Single amino acid substitution altering antigen-binding specificity," Proc. Natl Acad Sci U S A, Mar. 1982, vol. 79(6), pp. 1979-1983. doi: 10.1073/pnas.79.6.1979. PC/D: 6804947.
Sanda, Miloslav et al., "N- and O-Glycosylation of the SARS-COV-2 Spike Protein," Anal. Chem., vol. 93, No. 4, Jan. 7, 2021, pp. 2003-2009.
Search Report, dated Aug. 31, 2023, received in Russia Patent Application No. 2023100504.
Alam, MM et al., "Glycan-Modified Virus-Like Particles Evoke T Helper Type 1-Like Immune Responses," ACS Nano, vol. 15, No. 1, Jan. 26, 2021, published online Aug. 17, 2020, doi: 10.1021/acsnano.0c03023, pp. 309-321; (p. 19, figure 1b).
Avinash, MB et al., "Nanoarchitectonics of biomolecular assemblies for functional applications," Nanoscale, vol. 6, No. 22, Nov. 21, 2014, doi: 10.1039/c4nr04340e, pp. 13348-13369. (p. 18, figure 13c).
Bej, Raju et al., "Disulfide chemistry in responsive aggregation of amphiphilic systems," Royal Society of Chemistry, 2020, vol. 16, pp. 11-26. DOI: 10.1039/C9SM01960J.
Bellato, Frederica, "Targeting dendritic cells with mannosylated cationic glycopolymers for nucleic acid-mediated cancer immunotherapy," UNITesi, Magazzini Digitali, 2019, 25 pages. (https://tesidottorato.depositolegale.it/handle/20.500.14242/98191).
Bennua-Skalmowski, B. et al., "A Facile Conversion of Primary or Secondary Alcohols with n-Perfluorobutane-sulfonyl Fluoride/1,8-Diazabicyclo[5.4.0]undec-7-ene into their Corresponding Fleorides," Tetrahedron Letters, vol. 36, No. 15, pp. 2611-2614, 1995.
Byrne et al., "CRISPR/Cas9 gene editing for the creation of an MGAT1-deficient CHO cell line to control HIV-1 vaccine glycosylation," PLOS Biology, 2018, vol. 16, No. 8: e2005817.
Chokhawala, Harshai A. et al., "Enzymatic Synthesis of Fluorinated Mechanistic Probes for Sialidases and Sialytransferases," JACS Communications, 2007, vol. 129, pp. 10630-10631.
Definition of hemagglutinin [Influenza A virus (A/chicken/Jembrana/BPPV6/2004(H5N1))]. GenBank: ABE97562.1. https://www.ncbi.nlm.nih.gov/protein/ABE97562.1?report=genbank&log$=prottop&blast_rank=1&RID=CGUKON57013.
Definition of hemagglutinin [Influenza A virus (A/Singapore/GP4444/2010(H1N1))]. GenBank: AEH59357.1. https:// www.ncbi.nlm.nih.gov/protein/AEH59357.1?report=genbank&log$=prottop&blast_rank=1&RID=CGTA0JCD016.
Doboszewski, Bogdan et al., "The rapid synthesis of deoxyfluoro sugars using tris(dimethylamino)sulfonium difluorotrimethylsilicate (TASF)1," 1987, Canadian Journal of Chemistry, 65(2): 412-419.
Fan, CY et al., "Synthesis of Dendritic Cell-Targeted Polymeric Nanoparticles for Selective Delivery of mRNA Vaccines to Elicit Enhanced Immune Responses," bioRxiv, Epub: Nov. 14, 2023; pp. 1-12; entire document; DOI: 10.1101/2023.11.13.566827.
GenBank Accession NCBI No. QHD43416.1 (surface glycoprotein [Severe acute respiratory syndrome coronavirus 2]; published Mar. 18, 2020.
GenBank Accession No. nC_048600.1 (Cricetulus griseus strain 17A/GY chromosome 7, alternate assembly CriGri-PICRH-1.0, whole genome shotgun sequence. Jul. 12, 2020.
Huang et al., "Vaccination with SARS-COV-2 spike protein lacking glycan shields elicits enhanced protective responses in animal models," Sci Transl Med., Apr. 6, 2022, vol. 14(639):eabm0899.
Huang, Han-Yi et al., "Vaccination with SARS-COV-2 spike protein lacking glycan shields elicits enhanced protective responses in animal models," Sci. Transl. Med., vol. 14, eabm0899, (2022), 13 pages.
Krammer, Florian et al., "Chimeric Hemagglutinin Influenza Virus Vaccine Constructs Elicit Broadly Protective Stalk-Specific Antibodies," Journal of Virology, Jun. 2013, vol. 87, No. 12, pp. 6542-6550.
Kurzawa, Timon, "1,1,2,2,3,3,4,4,4-Nonafluorobutane-1-sulfonyl fluoride (NfF)," Synlett, 2015, vol. 26, pp. 1422-1423.
Shin et al., "CRISPR/Cas9 targeting events cause complex deletions and insertions at 17 sites in the mouse genome," Nature Communications, 2017, vol. 8, Art. 15464.
Wang, Shih-Chi et al., "Development of a universal influenza vaccine using hemagglutinin stem protein produced from Pichia pastoris," Virology, 2019, vol. 526, pp. 125-137.
Yang et al., "Glucoproteomic Characterization of FUT8 Knock-Out Cells Reveals Roles of FUT8 in the Glycosylation," Frontiers in Chemistry, Oct. 28, 2021, vol. 9, No. 755238, pp. 1-9, entire document.
Ding, Li et al., "A Photobacterium sp. [alpha]2-6-sialyltransferase (Psp2,6ST) mutant with an increased expression level and improved activities in sialylating Tn antigens," Carbohydrate Research, 2014, vol. 408, 127-133 (7 pages).
Du, Dan et al., "The role of glucose transporters in the distribution of p-aminophenyl-[alpha]-D-mannopyranoside modified liposomes within mice brain," Journal of Controlled Released, 2014, vol. 182. pp. 99-110.
Engdahl, Cecilia et al., "Estrogen induces St6gal1 expression and increases IgG sialylation in mice and patients with rheumatoid arthritis: a potential explanation for the increased risk of rheumatoid arthritis in postmenopausal women," Arthritis Research & Therapy, 2018, vol. 20:84 (11 pages).
Geisler, Christoph et al., "Engineering [beta]1,4-galactosyltransferase I to reduce secretion and enhance N-glycan elongation in insect cells," Journal of Biotechnology, 2015, vol. 193, 52-65 (14 pages).
Gong, Yanqiu et al., "The glycosylation in SARS-CoV-2 and its receptor ACE2," Signal Transduction and Targeted Therapy, 2021, vol. 6, 396 (24 pages).
Goswami, Roshan et al., "Conjugation of Mannans to Enhance the Potency of Liposome Nanoparticles for the Delivery of RNA Vaccines," Pharmaceutics, 2021, vol. 13, 240, 13 pages.
Grant, Oliver C. et al., "Analysis of the SARS-CoV-2 spike protein glycan shield reveals implications for immune recognition," Scientific Reports, 2020, vol. 10, 14991. https://doi.org/10.1038/s41598-020-71748-7.
Gutierrez Reyes, Cristian D., et al. "N-Glycome Profile of the Spike Protein S1: Systemic and Comparative Analysis from Eleven Variants of SARS-CoV-2," Biomolecules, 2023, vol. 13, pp. 1421 (17 pages).
He, P. et al., "Advances in aluminum hydroxide-based adjuvant research and its mechanism," Human Vaccine and Immunotherapeutics, 2015, vol. 11, iss. 2, pp. 477-488.
Hombu, Ryoma et al., "Cellular and Molecular Engineering of Glycan Sialylation in Heterologous Systems," Molecules, 2021, vol. 26, 5950 (27 [ages).
Ma et al., "The Role of Glucose Transporters in the Distribution of p-aminophenyl mannppyranose modified liposomes within mice brains," Journal of Controlled Release, 182, pp. 99-110. (Year: 2014).
Pappalardo, Juan Sebastian et al., "Characterization of a Nanovaccine Platform Based on an [alpha]1,2-Mannobiose Derivative Shows

(56) References Cited

OTHER PUBLICATIONS

Species-non-specific Targeting to Human, Bovine, Mouse, and Teleost Fish Dendritic Cells," Molecular Pharmaceutics, 2021, vol. 18, 2540-2555.
Wang, Ce et al., "Lymphatic-targeted cationic liposomes: A robust vaccine adjuvant for promoting long-term immunological memory," Vaccine, 2014, vol. 32, 5475-5483.
Wang, Ce et al., Supplementary Data, 2014, Vaccine, 32, 5475-5483.
Wang, Qiong et al., "Antibody glycoengineering strategies in mammalian cells," Biotechnology and Bioengineering, 2018, vol. 115:1378-1393.
Wu, Chung-Yi et al., "Glycosite-deleted mRNA of SARS-CoV-2 spike protein as a broad-spectrum vaccine," PNAS, 2022, vol. 119, No. 9. https://doi.irg/10.1073/pnas.2119995119.
Zhang, Yong et al., "Site-specific N-glycosylation Characterization of Recombinant SARS-CoV-2 Spike Proteins," Mol Cell Proteomics, 2021, vol. 20, 100058. https://doi.org/10.1074/mcp.RA120.002295.

\* cited by examiner

METHODS AND COMPOSITIONS FOR TARGETED DELIVERY BY POLYMERSOMES

CROSS-REFERENCE TO RELATED APPLICATIONS

This application claims the priority of U.S. Provisional Patent Applications No. 63/458,102, filed on Apr. 8, 2023, U.S. Provisional Patent Applications No. 63/587,231, filed on Oct. 2, 2023, and U.S. Provisional Patent Applications No. 63/575,056, filed on Apr. 5, 2024, The entirety of the aforementioned application is incorporated herein by reference.

FIELD

The present disclosure is generally directed to compositions and methods relating to polymeric nanocarriers, particularly pharmaceutical formulations comprising polymersomes capable of selective/targeted delivery of a payload to a desired target region in a tissue or to a cell.

BACKGROUND OF THE INVENTION

Delivery by nanotechnology has been widely used in scientific, industrial, and clinical applications. It has become a promising way for drug delivery, providing advantages including improving solubility and penetration of drug molecules. In a recent example, the mRNA vaccines developed against COVID-19 viruses used a special lipid nanoparticle (LNP) adapted to encapsulate and stabilize mRNA molecules given that the mRNA molecules were generally unstable and needed to be stored at low temperatures (e.g., −70° C.). The typical lipid nanoparticles are usually composed of several types of lipids. The ratio of those lipids requires fine-tuning, and the manufacturing of the lipid nanoparticles can be costly, and the lipid nanoparticles generally cannot deliver the mRNA molecules selectively. Therefore, there is a need in the field for a nanoparticle with simpler construction and the ability to be selectively delivered.

BRIEF SUMMARY OF THE INVENTION

In one aspect, the present disclosure provides a copolymer for forming a polymersome. The copolymer comprises an initiator block, comprising a glycan head, and a propagator block, further comprising a functional moiety, which comprises a guanidine group, a zwitterion group, a diethylene triamine, or a combination thereof; and a linkage, covalently connecting the initiator block and the propagator block, wherein the linkage comprises a disulfide bond.

In one aspect, the present disclosure provides a polymersome. The polymersome comprises a membrane defining an inner space, wherein the membrane comprises the exemplary copolymer of the present disclosure.

In one aspect, the present disclosure provides a pharmaceutical formulation comprising, which comprises a polymersome of the present disclosure.

In one aspect, the present disclosure provides a kit for preparing a polymersome. The kit comprises a first reagent, comprising an initiator, wherein the initiator comprises a glycan head and an initiator linking moiety, and a second reagent, comprising a propagator, wherein the propagator comprises a functional moiety and a propagator linking moiety, wherein the functional moiety comprises a guanidine group, a zwitterion group, a diethylene triamine, or a combination thereof; and wherein the initiator linking moiety is configured to couple with the propagator linking moiety via a linkage comprising a disulfide bond.

In one aspect, the present disclosure provides a method for targeted delivery of a payload in a subject. The method comprises administering to the subject an effective amount of a pharmaceutical formulation comprising a polymersome, wherein the polymersome comprises a membrane encapsulating the payload, and wherein the membrane comprises a copolymer of the present disclosure.

In one aspect, the present disclosure provides a method of preventing or treating a disease in a subject, comprising administering to the subject an effective amount of a pharmaceutical formulation comprising a polymersome, wherein the polymersome comprises a membrane, wherein the membrane comprises the polymeric component of any one of claims 1 to 34; and a payload, encapsulated within the membrane; and wherein the payload is a therapeutic agent or derives a therapeutic agent.

In one aspect, the present disclosure provides a method of boosting an adaptive immune response, comprising administering to a subject an effective amount of a pharmaceutical formulation comprising a polymersome, wherein the polymersome comprises a membrane encapsulating the payload, and wherein the membrane comprises a copolymer of the present disclosure, wherein the payload is immunogenic or derives an immunogenic biomolecule.

DETAILED DESCRIPTION OF THE INVENTION

Figure 1A:
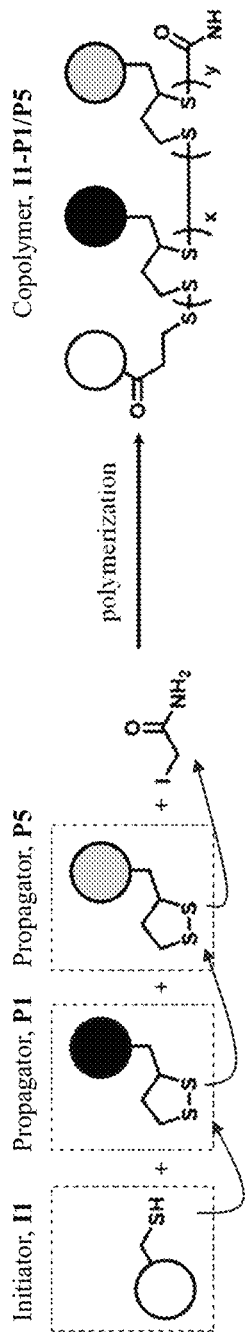
FIG. 1A represents a schematic illustrating an exemplary synthesis of the exemplary copolymer of the present disclosure. X and Y are both integers and are independently from 9 to 14.

Delivery by nanoparticles has been widely used in various applications. In addition to lipid nanoparticles (LNP), arguably the most common type of nanoparticle, polymersomes, another type of nanoparticle, have also gained increasing attention in industrial and clinical applications. Polymersomes (i.e., polymer-based nanoparticles, polymer vesicles, or polymer nanoparticles (PNP)) are enclosures, self-assembled from amphiphilic block copolymers. These amphiphilic block copolymers are macromolecules comprising at least one hydrophobic polymer block and at least one hydrophilic polymer block. When hydrated, these amphiphilic block copolymers self-assemble into enclosures such that the hydrophobic blocks tend to associate with each other to minimize direct exposure to water and form the inner surface of the enclosure, and the hydrophilic blocks face outward, forming the outer surface of the enclosure. The hydrophobic core of these aqueous soluble polymersomes can provide an environment to solubilize additional hydrophobic molecules. As such, these aqueous soluble polymersomes can act as carrier polymers for hydrophobic molecules encapsulated within the polymersomes. Moreover, the self-assembly of the amphiphilic block polymers occurs in the absence of stabilizers, which would otherwise provide colloidal stability and prevent aggregation.

Polymersomes offer many advantages, such as high stability in storage, more accessibility to manufacture, convenient surface modification, high biocompatibility, and controlled release mechanisms. However, the industry still lacks polymersomes that efficiently deliver drug molecules to specific regions of an organism. It is presumably due to the fact that the conventional polymersomes do not encapsulate the payload (e.g., a biomolecule administered for its therapeutic effect) effectively and are generally unstable in serum. Moreover, they are also not capable of selective delivery.

Polymersome

Accordingly, one aspect of the present disclosure provides a polymersome. The polymersome of the present disclosure is designed to provide selective delivery (or targeted delivery) and good encapsulation efficiency, especially for nucleic acid-type payloads. The exemplary polymersome comprises a membrane, which defines an inner space configured to encapsulate or carry a payload. The membrane of the polymersome of the present disclosure comprises a copolymer comprising an initiator block, a propagator block, and a linkage, wherein the linkage covalently connects the initiator block and the propagator block and comprises a disulfide bond. The initiator block comprises a glycan head, and the propagator block comprises a functional moiety comprising a guanidine group, a zwitterion group, a diethylene triamine, or a combination thereof.

Without wishing to be bound by theories, the disulfide bond (i.e., a disulfide linkage) of the linkage is selected for its biodegradable property in intracellular environments and/or for thiol-mediated uptake. Therefore, the disulfide bond can facilitate the uptake of the polymersome of the present disclosure and degradation thereof after uptake to release the encapsulated payload via, for example, an intracellular glutathione-mediated cleavage.

In some embodiments, the copolymer might comprise more than one initiator block and more than one propagator block. For example, the copolymer might comprise one initiator block, a first propagator block, and a second propagator block, wherein the initiator block and the first propagator block and the first propagator block and the second propagator block are both connected via a linkage.

Initiator Block

In certain embodiments, the initiator block comprises a glycan head configured to provide selective delivery. To that end, the glycan head might have a targeting moiety that is a ligand of a target (e.g., a receptor on a target cell). In some embodiments, the targeting moiety can be a terminal moiety of the glycan head for a better chance to interact and bind the target. Nevertheless, the present disclosure is not limited to that configuration. In some embodiments, the target cell for the selective delivery is an antigen-presenting cell (APC, e.g., a dendritic cell). In some embodiments, the target cell can be other types of immune cells. In yet some other embodiments, the target can be any biological cells with which the payload is designed to interact.

In certain embodiments, the initiator block is configured to bind to a lectin receptor, such as Siglec-1 (sialoadhesin), Siglec-2, Siglec-5/E, and DC-SIGN, with a certain degree of affinity, thereby exhibiting a better uptake by a specific type of APCs. In some embodiments, the glycan head of the initiator block comprises a mannosidase, which can be a terminal mannose configured to bind DC-SIGN on a dendritic cell. In some embodiments, the glycan head comprises a sialoside. In some embodiments, to target Siglec-1, the glycan head can comprise 9-N-(4H-thieno[3,2-c]chromene-2-carbamoyl)-Neu5Ac-α2,3-Gal-GlcNAc. In some embodiments, to target Siglec-2, the glycan head can comprise 9-Biphenyl Neu5Ac-α2,6-Gal. In some embodiments, to target Siglec-5/E, the glycan head can comprise Neu5Ac-α2,3-Gal-GlcNAc.

Binding in Acidic Conditions.

In some embodiments, the binding between the initiator block and a target is $Ca^{2+}$-correlated, and the calcium coordination might decrease at a low pH environment, resulting in lower binding affinity. Therefore, to provide a better binding affinity under acidic conditions, the glycan head of the initiator block can comprise an aryl group. Without wishing to be bound by any theories, the aryl group may engage in the CH-π and hydrophobic interactions that enhance the binding under acidic conditions. The aryl group can be an unsubstituted benzene or a benzene substituted with a halide or an alkyl halide (e.g., a $CF_3$). In some embodiments, the aryl group is coupled with the targeting moiety. For example, the glycan head of the initiator block can comprise an O-aryl mannoside.

Structural Configuration of Glycan Head.

In certain embodiments, the glycan head can be a linear structure or a branched structure. In some embodiments, the glycan head might have a plurality of targeting moieties, for example, 2, 3, 4, 5, 6, 7, 8, 9, or 10 targeting moieties. The plurality of targeting moieties can be arranged in a linear, branched, or star configuration. For example, the glycan head of the initiator block might comprise a mono-mannoside, a di-mannoside, or a tri-mannoside, and when the glycan head comprises a tri-mannoside, the tri-mannoside can be a linear form or a branched structure, such as a α-1,3-α-1,6-trimannoside. In certain embodiments, it is noticed that, in some circumstances, a branched configuration (e.g., a tri-mannoside glycan head) shows superior binding affinity to its target receptor.

Initiator Spacer.

In some embodiments, the initiator block further comprises an initiator spacer. The initiator spacer is configured to provide structural flexibility to the glycan head and/or provide hydrophobicity to the entire copolymer to facilitate the assembly of the polymersome. Without wishing to be bound by theories, the flexibility allows the glycan head to move during the interaction between the initiator block and the target, thereby facilitating the binding between them.

A preferred spacer is biocompatible. In some embodiments, the initiator spacer comprises a saturated carbon moiety, a polyethylene glycol (PEG) moiety, or a combination thereof. For example, the spacer can be a polyethylene glycol (PEG) moiety, formed by 1, 2, 3, 4, 5, 6, 7, 8, 9, 10, 12, 15, 18, 20, 24, 30, 36, 40, 48, 50, 55, 60, 65, or 72 ($OCH_2CH_2$) subunits, or any ranges defined by the foregoing endpoints, such as 2 to 72, 2 to 60, 2 to 48, 2 to 36, 2 to 24, 2 to 18, 2 to 15, 2 to 10, 4 to 72, 4 to 60, 4 to 48, 4 to 36, 4 to 24, 4 to 18, 4 to 15, 4 to 10, 8 to 72, 8 to 60, 8 to 48, 8 to 36, 8 to 24, 8 to 18, 8 to 15, or 8 to 10 ($OCH_2CH_2$) subunits. In some embodiments, the PEG moiety can be a linear, branched, or star structure.

In some embodiments, the spacer is a saturated carbon moiety, which can be a lipid tail connecting to the glycan head. In some embodiments, the saturated carbohydrate comprises at least 2, 3, 4, 5, 6, 7, 8, 9, 10, 11, 12, 13, 14, or 15 carbons, or any range of carbons defined by the foregoing endpoints, such as 2 to 15, 2 to 12, 2 to 10, 2 to 8, 2 to 6, 2 to 4, 3 to 15, 3 to 14, 3 to 13, 3 to 12, 3 to 11, 3 to 10, 3 to 9, 3 to 8, 3 to 7, 3 to 6, 3 to 5, 4 to 15, 4 to 14, 4 to 13, 4 to 12, 4 to 11, 4 to 10, 4 to 9, 4 to 8, 4 to 7, 4 to 6, 6 to 15, 6 to 14, 6 to 13, 6 to 12, 6 to 11, 6 to 10, 6 to 9, or 6 to 8 carbons.

Binding Affinity.

In some embodiments, the binding affinity between the glycan head of the initiator block and a target can be defined by a dissociation constant ($K_D$). In some embodiments, the $K_D$ at pH 7.4 can be 5, 10, 15, 20, 30, 40, 50, 75, 100, 125, 150, 200, 250, 300, 350, 400, 450, 500, 600, 700, 800, 900, 1000, 1250, 1500, 1750, 2000, 2250, 2500, 3000, 3250, 3500, 3750, 4000, 4250, 4500, 4750, 5000, 5250, 5500, 5750, 6000, 6250, 6500, 6750, 7000, 7250, 7500, 7750, or 8000 nM, or any range defined by the foregoing endpoints, such as, 5 to 8000, 5 to 7000, 5 to 6000, 5 to 5000, 5 to 4000, 5 to 3000, 5 to 2500, 5 to 2000, 5 to 1500, 5 to 1250, 5 to 1000, 5 to 900, 5 to 800, 5 to 700, 5 to 600, 5 to 500, 5 to 400, 5 to 300, 5 to 200, 5 to 150, 5 to 100, 5 to 75, 5 to 50, 5 to 30, 5 to 20, 10 to 8000, 10 to 7000, 10 to 6000, 10 to 5000, 10 to 4000, 10 to 3000, 10 to 2500, 10 to 2000, 10 to 1500, 10 to 1250, 10 to 1000, 10 to 900, 10 to 800, 10 to 700, 10 to 600, 10 to 500, 10 to 400, 10 to 300, 10 to 200, 10 to 150, 10 to 100, 10 to 75, 10 to 50, 10 to 30, or 10 to 20 nM.

In some other embodiments, the $K_D$ at pH 5 can be 1, 2, 3, 4, 5, 10, 15, 20, 30, 40, 50, 75, 100, 125, 150, 200, 250, 300, 350, 400, 450, 500, 550, 600, 650, 700, 750, 800, 850, 900, 1000, 1250, 1500, 1750, or 2000 nM, or any range defined by the foregoing endpoints, such as, 1 to 2000, 1 to 1500, 1 to 1000, 1 to 900, 1 to 800, 1 to 750, 1 to 700, 1 to 650, 1 to 600, 1 to 550, 1 to 500, 1 to 450, 1 to 400, 1 to 350, 1 to 300, 1 to 250, 1 to 200, 1 to 150, 1 to 100, 1 to 75, 1 to 50, 1 to 40, 1 to 30, 1 to 20, 1 to 10, or to 5, 5 to 2000, 5 to 1500, 5 to 1000, 5 to 900, 5 to 800, 5 to 750, 5 to 700, 5 to 650, 5 to 600, 5 to 550, 5 to 500, 5 to 450, 5 to 400, 5 to 350, 5 to 300, 5 to 250, 5 to 200, 5 to 150, 5 to 100, 5 to 75, 5 to 50, 5 to 40, 5 to 30, 5 to 20, 5 to 10 nM.

Examples

In some embodiments, the glycan head of the initiator block comprises a $9^{BPC}$Neu5Ac conjugated N-glycan head (e.g., IB2), Neu5Ac conjugated N-glycan (e.g., IB3), $9^{TCC}$Neu5Ac conjugated N-glycan (e.g., IB4), or a combination thereof. In certain embodiments, the glycan head comprises at least one of the following structures (Please note that "IB" stands for initiator block, which describes an initiator conjugated in the copolymer of the present disclosure. Nevertheless, "IB" can be used interchangeably with "I," standing for initiator, for concise description):

IB2
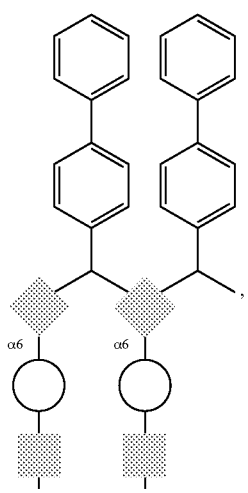
IB3
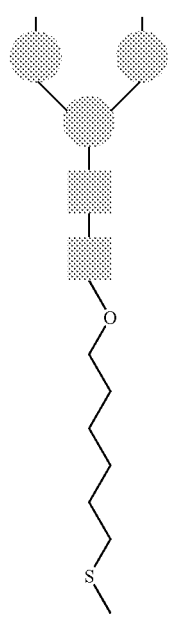
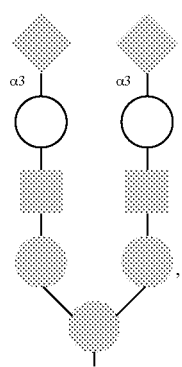
-continued
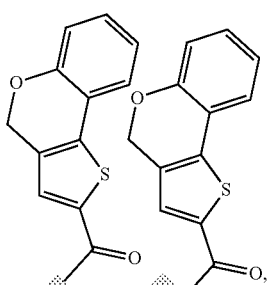
IB4
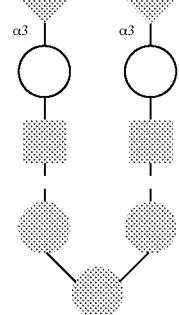

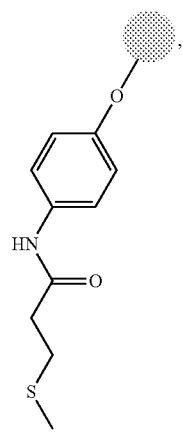
IB5
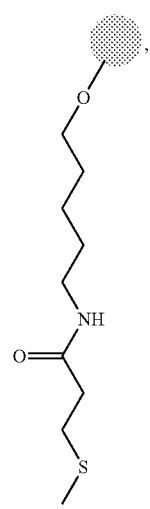
IB6
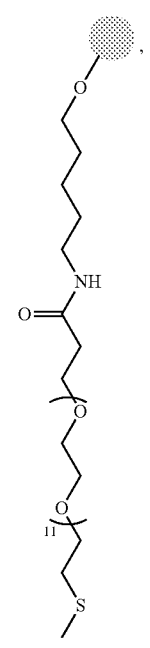
IB8
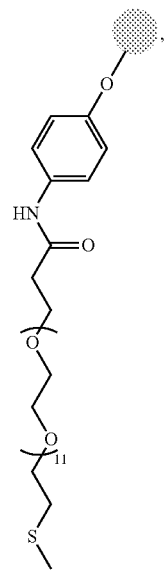
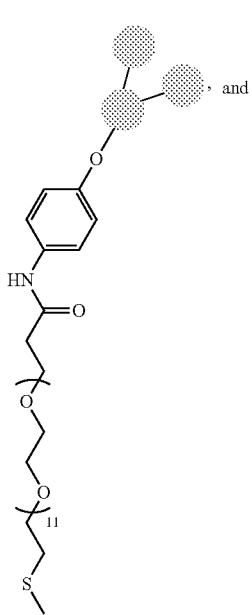
IB9

IB10

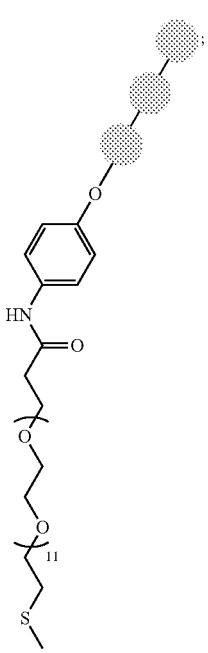

wherein the solid circle represents mannoside, the open circle represents Galactose, the solid square represents GlcNAc, and the diamond represents Neu5Ac.

Propagator Block

In certain embodiments, an exemplary polymersome of the present disclosure exhibits desired properties such as efficient payload encapsulation, reduced serum protein adsorption, enhanced membrane fusion, and efficient payload release after uptake. At least one of the desired properties is provided by the propagator block of the present disclosure. To that end, the propagator block of the present disclosure comprises a functional moiety comprising a guanidine group, a zwitterion group, a diethylene triamine, or a combination thereof.

In some embodiments, the copolymer of the present disclosure comprises a single propagator block providing at least one of the desired properties. In some embodiments, the copolymer of the present disclosure comprises a plurality of propagator blocks, each providing at least one of the desired properties.

Efficient Payload Encapsulation.

In some embodiments, the polymersome of the present disclosure is designed to carry a nucleic acid-type payload, such as an mRNA molecule or a DNA molecule. In such embodiments, the propagator block of the copolymer of the polymersome can comprise a guanidine group. In some embodiments, the propagator block comprises 1, 2, 3, 4, 5, or more guanidine groups. Without wishing to be bound by theories, a plurality of guanidine groups in the propagator block provides a stronger salt bridge between the guanidinium groups of the copolymer and the phosphate groups of a nucleic acid molecule (e.g., a mRNA). In certain embodiments, the propagator block comprises three guanidine groups.

Reduced Serum Protein Adsorption and Enhanced Membrane Fusion.

As mentioned above, one of the common disadvantages of polymersomes is their purported instability in serum because of serum protein absorption. To reduce serum protein absorption to enhance serum stability, the copolymer of the present disclosure can comprise a zwitterion, which also enhances the polymersome's membrane fusion with a target cell. The zwitterion of the present disclosure can be a molecule/moiety with overall zero charge by carrying an equal number of positively charged and negatively charged functional groups at pH 4.5 to 7.5. In some embodiments, the zwitterion of the present disclosure comprises an isoelectric point between pH 4.5 and 7.5. The zwitterion can be, but is not limited to, choline phosphates (CP), sulfothetins, phosphonium sulfonates, or psilocybin. In some embodiments, the zwitterion of the present disclosure comprises an alkylphosphobetaine group comprising a phosphate group and an amine group, providing a negative charge and a positive charge, respectively.

Efficient Payload Release after Uptake.

Another desired property of a polymersome is the ability to release the entrapped/encapsulated payloads efficiently after uptake. Releasing the entrapped/encapsulated payloads takes place in the lysosome of a target cell, which results from an escape from the endosomal/lysosomal pathway or degradation of the polymersome. In some embodiments, the zwitterion of the propagator block can facilitate the endosomal escape. Yet, in some embodiments, the propagator block can further comprise an alkyl chain, which also contributes to the endosomal escape.

On the other hand, in some embodiments, to facilitate the lysosomal degradation, the propagator block of the present disclosure can comprise a diethylene-triamine moiety. The terminal amine residue of the diethylene-triamine moiety can also be used for additional functionalization. Alternatively, the propagator block of the present disclosure can comprise ethylenediamine, 1-(2-aminoethyl)piperazine, and/or tris(2-aminoethyl)amine.

Propagator Spacer.

In some embodiments, the propagator block of the present disclosure comprises a propagator spacer mainly configured to provide the copolymer with the required hydrophobicity for assembly into a polymersome. In some embodiments, the propagator spacer comprises a saturated carbon moiety, a polyethylene glycol (PEG) moiety, or a combination thereof.

In some embodiments, the spacer can be a polyethylene glycol (PEG) moiety, formed by 1, 2, 3, 4, 5, 6, 7, 8, 9, 10, 12, 15, 18, 20, 24, 30, 36, 40, 48, 50, 55, 60, 65, or 72 ($OCH_2CH_2$) subunits, or any ranges defined by the foregoing endpoints, such as 2 to 72, 2 to 60, 2 to 48, 2 to 36, 2 to 24, 2 to 18, 2 to 15, 2 to 10, 4 to 72, 4 to 60, 4 to 48, 4 to 36, 4 to 24, 4 to 18, 4 to 15, 4 to 10, 8 to 72, 8 to 60, 8 to 48, 8 to 36, 8 to 24, 8 to 18, 8 to 15, or 8 to 10 ($OCH_2CH_2$) subunits. In some embodiments, the PEG moiety can be a linear, branched, or star structure.

In some embodiments, the saturated carbon moiety can be a lipid tail extending from the propagator block. In some embodiments, the saturated carbohydrate comprises at least 2, 3, 4, 5, 6, 7, 8, 9, 10, 11, 12, 13, 14, or 15 carbons, or any range of carbons defined by the foregoing endpoints, such as 2 to 15, 2 to 12, 2 to 10, 2 to 8, 2 to 6, 2 to 4, 3 to 15, 3 to 14, 3 to 13, 3 to 12, 3 to 11, 3 to 10, 3 to 9, 3 to 8, 3 to 7, 3 to 6, 3 to 5, 4 to 15, 4 to 14, 4 to 13, 4 to 12, 4 to 11, 4 to 10, 4 to 9, 4 to 8, 4 to 7, 4 to 6, 6 to 15, 6 to 14, 6 to 13, 6 to 12, 6 to 11, 6 to 10, 6 to 9, or 6 to 8 carbons. In certain embodiments, the propagator spacer comprises a monocarboxylic acid amide moiety (e.g., a lipoamide moiety) or other biocompatible structure, which provides a saturated carbohydrate and a functional group for conjugation.

Examples

In some embodiments, the propagator block of the present disclosure comprises at least one of the following structures (Please note that "PB" stands for propagator block, which describes a propagator conjugated in the copolymer of the present disclosure. Nevertheless, "PB" can be used interchangeably with "P," standing for propagator, for concise description.):

in the desired property it provides, thereby forming the copolymer as a hetero-copolymer.

In some embodiments, a hetero-copolymer comprises any two or more propagator blocks PB1, PB2, PB3, PB4, and PB5. In some embodiments, the copolymer comprises at

PB1

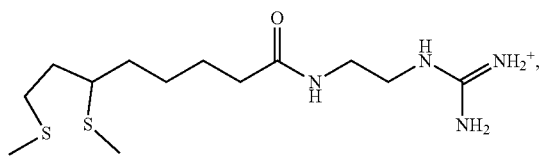

PB2

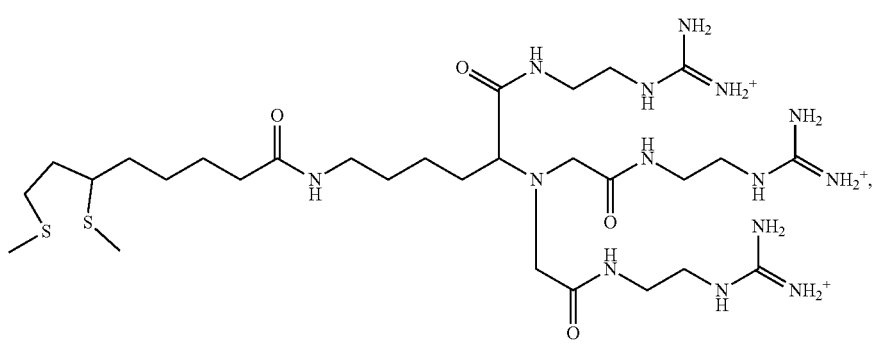

PB3

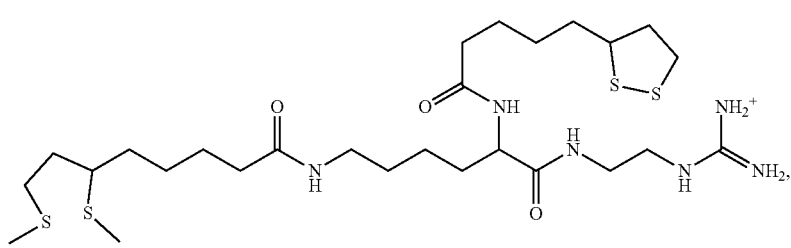

PB4

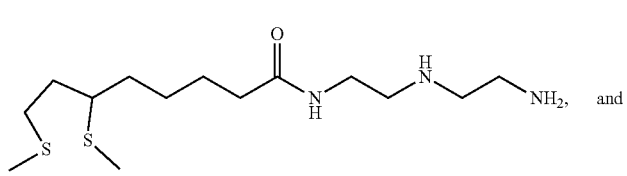

and

PB5

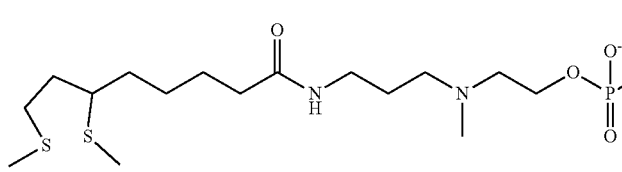
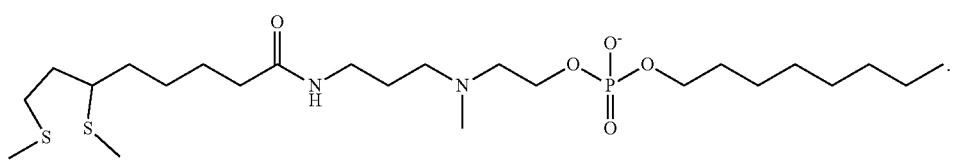

Copolymer Propagator Block.

In some embodiments, the copolymer comprises a plurality of the propagator blocks and a plurality of the linkages, wherein each propagator block of the plurality of the propagator blocks connects to at least another propagator block of the plurality of the propagator blocks or the initiator block via one of the plurality of the linkages. Without wishing to be bound by theories, the present disclosure contemplates that having two or more propagators in the structure of the copolymer is beneficial. Each of the two or more propagators can provide at least one of the desired properties of efficient payload encapsulation, reduced serum protein adsorption, enhanced membrane fusion, and efficient payload release after uptake. In some embodiments, each of the two or more propagators is different in structure and/or least two propagator blocks being (1) PB1 and PB5, (2) PB1 and PB4, (3) PB2 and PB5, (4) PB2 and PB5, or (5) PB1, PB4, and PB5, wherein the two or more propagators in a copolymer can be expressed by the formula numbers of the two or more propagators separated by a symbol "/." For example, the two propagator blocks of PB1 and PB5 in a copolymer can be expressed as PB1/PB5. Nevertheless, the order and the amounts of the propagator blocks in the referring copolymer are not limited by how they are named. Without wishing to be bound by theories, the present disclosure found that a copolymer of PB1/PB4, PB2/PB4, PB1/PB5, and PB2/PB5 exhibited superior intracellular delivery due to efficient membrane fusion and payload release.

In certain embodiments, the hetero-copolymer copolymer having two or more different types of propagator blocks can be configured with any initiator of I2, I3, I4, I5, I6, I7, I8, I9, and I10. The conjugation of the initiator and the propagator can be expressed by the formula numbers of the initiator and the propagator separated by a hyphen symbol "-." For example, a copolymer comprising the initiator I5 and the propagator P5 can be expressed as I5-P5. Nevertheless, the order and the amounts of the initiator blocks and/or the propagator blocks in the referring copolymer are not limited by how they are named. In some embodiments, a copolymer of a hetero-copolymer having two or more different types of propagators conjugated with one initiator of the present disclosure can be selected from a group consisting of I5-P1/P5, I5-P1/P4, I5-P2/P5, I5-P2/P4, I5-P1/P4/P5, I6-P1/P5, I6-P1/P4, I6- P2/P5, I6-P2/P4, I6-P1/P4/P5, I7-P1/P5, I7-P1/P4, I7-P2/P5, I7-P2/P4, I7-P1/P4/P5, I8-P1/P5, I8-P1/P4, I8-P2/P5, I8-P2/P4, I8-P1/P4/P5, I9-P1/P5, I9-P1/P4, I9-P2/P5, I9-P2/P4, I9-P1/P4/P5, I10-P1/P5, I10-P1/P4, I10-P2/P5, I10-P2/P4, and I10-P1/P4/P5.

In some embodiments, the hetero-copolymer copolymer comprises a number of a first propagator blocks and a number of a second propagator blocks. In certain embodiments, the number of the first propagator blocks is 1, 2, 3, 4, 5, 6, 7, 8, 9, 10, 11, 12, 13, 14, 15, 16, 17, 18, 19, 20, or more, or any range defined by the foregoing endpoints, such as 1 to 20, 1 to 18, 1 to 16, 1 to 14, 1 to 12, 1 to 10, 1 to 8, 1 to 6, 1 to 4, 3 to 20, 3 to 18, 3 to 16, 3 to 14, 3 to 12, 3 to 10, 3 to 8, 3 to 6, 3 to 4, 6 to 20, 6 to 18, 6 to 16, 6 to 14, 6 to 12, 6 to 10, 6 to 8, 9 to 20, 9 to 18, 9 to 16, 9 to 14, 9 to 12, 12 to 20, 12 to 18, 12 to 16. In certain embodiments, the number of the second propagator blocks is 1, 2, 3, 4, 5, 6, 7, 8, 9, 10, 11, 12, 13, 14, 15, 16, 17, 18, 19, 20, or more, or any range defined by the foregoing endpoints, such as 1 to 20, 1 to 18, 1 to 16, 1 to 14, 1 to 12, 1 to 10, 1 to 8, 1 to 6, 1 to 4, 3 to 20, 3 to 18, 3 to 16, 3 to 14, 3 to 12, 3 to 10, 3 to 8, 3 to 6, 3 to 4, 6 to 20, 6 to 18, 6 to 16, 6 to 14, 6 to 12, 6 to 10, 6 to 8, 9 to 20, 9 to 18, 9 to 16, 9 to 14, 9 to 12, 12 to 20, 12 to 18, 12 to 16. In some embodiments, the numbers of the first propagator blocks and/or the numbers of the second propagator blocks can be determined using Mass Spectrometry, but it is not limited.

Polymersome Comprising the Copolymer of the Present Disclosure

A polymersome of the present disclosure comprises a membrane, which comprises the copolymer of the present disclosure. In some embodiments, the membrane comprises a plurality of the copolymers of the present disclosure, which assemble into the membrane with the propagator blocks coupling with one another via hydrophobic interaction. The initiator block of each copolymer of the polymersome extends from the membrane and is exposed to the surrounding environment.

In some embodiments, the copolymer of the present disclosure comprises at least 50%, 60%, 70%, 80%, 90%, 95%, or 99% of the membrane of the polymersome, or any range defined by the foregoing endpoints, such as 50% to 99%, 50% to 95%, 50% to 90%, 50% to 85%, 50% to 80%, 50% to 75%, 50% to 70%, 50% to 65%, 50% to 60%, 60% to 99%, 60% to 95%, 60% to 90%, 60% to 85%, 60% to 80%, 60% to 75%, 60% to 70%, 60% to 65%, 70% to 99%, 70% to 95%, 70% to 90%, 70% to 85%, 70% to 80%, 50% to 75%, 80% to 99%, 80% to 95%, 80% to 90%, 80% to 85%, 90% to 99%, or 90% to 95%.

In some embodiments, the membrane comprises at least two different types of copolymers of the present disclosure. In certain embodiments, the membrane comprises copolymers comprising at least two different types of propagator blocks of the present disclosure. For example, the membrane comprises copolymers comprising a first propagator block and a second propagator block, wherein the molecular ratio of the first propagator block and the second propagator block in the membrane is 1, 1.5, 2, 2.5, 3, 3.5, 4, 4.5, 5, 5.5, 6, 6.5, 7, 8, 9, 10, 15, 20, or 25, or any range defined by the foregoing endpoints, such as 1 to 25, 1 to 20, 1 to 15, 1 to 10, 1 to 8, 1 to 6, 1 to 5, 1 to 4, 1 to 3, 1 to 2.5, 1 to 2, 1 to 1.5, 2 to 25, 2 to 20, 2 to 15, 2 to 10, 2 to 8, 2 to 6, 2 to 5, 2 to 4, 2 to 3, or 2 to 2.5.

In some embodiments, the polymersome of the present disclosure can be a dendritic cell targeting vaccine (DCTV) for specifically targeted delivery of the payload to dendritic cells, thereby achieving and or improving the immunogenic response of the vaccine.

Size of the Polymersome.

In some embodiments, the polymersome of the present disclosure has a diameter of 0.001, 0.005, 0.01, 0.05, 0.1, 0.15, 0.2, 0.3, 0.4, 0.5, 0.6, 0.7, 0.8, 0.9, 1, 1.5, 2, 2.5, 3, 3.5, 4, 4.5, or 5 microns, or any range defined by the foregoing endpoints, such as 0.001 to 5, 0.001 to 4, 0.001 to 3, 0.001 to 2, 0.001 to 1, 0.001 to 0.8, 0.001 to 0.6, 0.001 to 0.4, 0.001 to 0.2, 0.001 to 0.1, 0.001 to 0.05, 0.001 to 0.01, 0.001 to 0.005, 0.05 to 5, 0.05 to 4, 0.05 to 3, 0.05 to 2, 0.05 to 1, 0.05 to 0.8, 0.05 to 0.6, 0.05 to 0.4, 0.05 to 0.2, 0.05 to 0.1, 0.1 to 5, 0.1 to 4, 0.1 to 3, 0.1 to 2, 0.1 to 1, 0.1 to 0.8, 0.1 to 0.6, 0.1 to 0.4, 0.1 to 0.2, 0.5 to 5, 0.5 to 4, 0.5 to 3, 0.5 to 2, 0.5 to 1, 0.5 to 0.8, 1 to 5, 1 to 4, 1 to 3, or 1 to 2 microns. The size of the polymersome can be determined by using, but not limited to, Dynamic Light Scattering (DLS). In some embodiments, the polymersome of the present disclosure has a polydispersity index (PDI) of about 0.01, 0.05, 0.1, 0.2, 0.3, 0.4, 0.5, 0.6, 0.7, 0.8, 0.9, or 1, or any range defined by the foregoing endpoints, such as 0.01 to 1, 0.01 to 0.9, 0.01 to 0.8, 0.01 to 0.7, 0.01 to 0.6, 0.01 to 0.5, 0.01 to 0.4, 0.01 to 0.3, 0.01 to 0.2, 0.01 to 0.1, 0.01 to 0.05, 0.1 to 1, 0.1 to 0.9, 0.1 to 0.8, 0.1 to 0.7, 0.1 to 0.6, 0.1 to 0.5, 0.1 to 0.4, 0.1 to 0.3, or 0.1 to 0.2.

Zeta Potential and Molecular Weight.

Without wishing to be bound by theories, the zeta potential and molecular weight of a polymersome may affect the cellular uptake of the polymersome. In some embodiments, the polymersome of the present disclosure comprises a zeta potential of about −50, −40, −30, −20, −15, −10, −5, 0, +5, +10, +15, +20, +30, +40, or +50, or any range defined by the foregoing endpoints, such as −50 to +50, −50 to +40, −50 to +30, −50 to +20, −50 to +15, −50 to +10, −50 to +5, −50 to −5, −50 to −10, −50 to −15, −50 to −20, −20 to +50, −20 to +40, −20 to +30, −20 to +20, −20 to +15, −20 to +10, −20 to +5, −20 to −5, −20 to −10, −20 to −15, −15 to +50, −15 to +40, −15 to +30, −15 to +20, −15 to +15, −15 to +10, −15 to +5, −15 to −5, −15 to −10, +5 to +50, +5 to +40, +5 to +30, +5 to +20, +5 to +15, or +5 to +10. In some embodiments, the polymersome of the present disclosure comprises a molecular weight of about 1, 2, 3, 4, 5, 6, 7, 8, 10, 12, 15, 20, 25, 30, 35, 40, 45, 50 kDa, or any range defined by the foregoing endpoints, such as 1 to 50 kDa, 1 to 40 kDa, 1 to 30 kDa, 1 to 20 kDa, 1 to 15 kDa, 1 to 10 kDa, 1 to 5 kDa, 2 to 50 kDa, 2 to 40 kDa, 2 to 30 kDa, 2 to 20 kDa, 2 to 15 kDa, 2 to 10 kDa, 2 to 5 kDa, 5 to 50 kDa, 5 to 40 kDa, 5 to 30 kDa, 5 to 20 kDa, 5 to 15 kDa, 5 to 10 kDa, 8 to 50 kDa, 8 to 45 kDa, 8 to 40 kDa, 8 to 35 kDa, 8 to 30 kDa, 8 to 25 kDa, 8 to 20 kDa, 8 to 15 kDa, 8 to 10 kDa, 12 to 50 kDa, 12 to 45 kDa, 12 to 35 kDa, 12 to 25 kDa, 12 to 15 kDa, 25 to 50 kDa, 25 to 40 kDa, or 25 to 30 kDa.

Payload.

In some embodiments, the membrane of the polymersome defines an inner space configured to encapsulate or carry a payload. As described herein, "encapsulate a payload," "encapsulated within the inner space," or similar description refers to the condition that the payload is retained, enclosed, or surrounded by the membrane of the polymersome. The payload can move freely within the inner space or be attached covalently or non-covalently to the membrane. The encapsulation can be substantial, complete, or partial and does not exclude the possibility that part of the payload might be exposed to the environment outside the polymersome. In the embodiments of partial encapsulation, at least 1%, 5%, 10%, 20%, 30%, 40%, 50%, 60%, 70%, 80%, 90%, or 95% of the payload is retained, enclosed, or surrounded by the membrane of the polymersome. In some embodiments, the payload can be a biomolecule such as a nucleic acid, a compound, a polypeptide, a protein, a glycan head, or a combination thereof.

In some embodiments, the payload is a ribonucleic acid (RNA, e.g., an mRNA) or deoxyribonucleic acid (DNA, e.g., a double-strand DNA or a single-strand DNA), which, after being delivered by using the polymersome of the present disclosure to a target cell, can encode a polypeptide or a protein in vivo. Nucleic acid, such as a mRNA molecule used in the present disclosure, can be prepared by in vitro transcription from a reference nucleic acid. The in vitro transcription can be performed as described in the PCT patent publication WO2014/152027, filed on Mar. 13, 2014, which is incorporated by reference in its entirety.

In some embodiments, the polypeptide or the protein is immunogenic (e.g., antigenic) to an organism to which the polymersome is administered. In such embodiments, the polymersome of the present disclosure is used to encapsulate and carry an immunogenic protein or a nucleic acid configured to encode the immunogenic protein in vivo, such as an mRNA molecule in an RNA vaccine. The immunogenic protein can be a protein of a pathogen of viral (e.g., SARS-CoV-2, influenza (flu), respiratory syncytial virus (RSV), EBV, DENGUE, VZV, HIV, ZIKA, or NIPAH), bacterial, or fungal origin. In some embodiments, an immunogenic protein can be a spike protein of a virus. In certain embodiments, the spike protein can be of coronavirus (CoV) origin, such as SARS-CoV, MERS-CoV, and SARS-CoV-2. In some embodiments, examples of the coronavirus (CoV) described herein include but are not limited to, alpha-SARS-CoV2, beta-SARS-CoV2, gamma-SARS-CoV2, delta-SARS-CoV2, omicron-SARS-CoV2, and variants thereof.

In some embodiments, the payload is a nucleic acid, which can be a polynucleotide having an open reading frame configured to encode a polypeptide or protein in vivo. Such a polynucleotide might be modified with a 5'terminal cap, which is generated during an in vitro-transcription reaction using the following chemical RNA cap analogs: 3"-O-Me-m7G(5')ppp(5') G [the ARCA cap], G(5)ppp(5')A, G(5')ppp(5')G, m7G(5')ppp(5')A, or m7G(5')ppp(5')G (New England BioLabs, Ipswich, Mass.). A 5'-capping of a modified polynucleotide may be completed post-transcriptionally using a Vaccinia Virus Capping Enzyme to generate the "Cap 0" structure: m7G(5')ppp(5')G (New England BioLabs, Ipswich, Mass.). Cap 1 structure may be generated using both Vaccinia Virus Capping Enzyme and a 2'-O methyl-transferase to generate m7G(5')ppp(5')G-2'-O-methyl. Cap 2 structure may be generated from the Cap 1 structure followed by the 2'-O-methylation of the 5'-antepenultimate nucleotide using a 2'-O methyl-transferase. Cap 3 structure may be generated from the Cap 2 structure followed by the 2'-O-methylation of the 5'-preantepenultimate nucleotide using a 2'-0 methyl-transferase. Enzymes may be derived from a recombinant source. After being transfected into mammalian cells, the modified polynucleotides have a stability of between 12-18 hours, or greater than 18 hours, e.g., 24, 36, 48, 60, 72, or greater than 72 hours.

In some embodiments, the nucleic acid might be modified. In some embodiments, the nucleic acid might have several (more than one) modifications, the same or different from each other. In some embodiments, the nucleic acid contains, in a particular region, one, two, or more (optionally different) nucleoside or nucleotide modifications. In some embodiments, a modified nucleic acid (e.g., a modified mRNA polynucleotide) exhibits reduced degradation in a cell or organism relative to unmodified ones. In some embodiments, a modified nucleic acid may exhibit reduced immunogenicity in an organism, respectively (e.g., a reduced innate response).

In some embodiments, the modification can comprise chemical modifications. In some embodiments, the modification can be naturally-occurring, non-naturally-occurring, or both. Some exemplary modifications useful in the present disclosure include but are not limited to, modifications of a sugar, a nucleobase, an internucleoside linkage (e.g., to a linking phosphate, to a phosphodiester linkage, or to the phosphodiester backbone), or a combination thereof. In some embodiments, the nucleic acid (e.g., RNA) used as a payload of the present disclosure can be codon optimized. For example, the nucleic acid can be modified to enhance its G/C content. The G/C content of a nucleic acid may influence its stability. A nucleic acid having an increased amount of guanine (G) and/or cytosine (C) residues may be functionally more stable than those containing a large amount of adenine (A) and thymine (T) or uracil (U) nucleotides. For example, WO2002/098443 discloses a pharmaceutical composition containing an mRNA stabilized by sequence modifications in the translated region. Due to the degeneracy of the genetic code, the modifications work by substituting existing codons for those that promote greater RNA stability without changing the resulting amino acid.

In some embodiments, the nucleic acid might further comprise a sequence encoding a signal peptide. The signal peptide might comprise three regions: (1) an N-terminal region of differing length, which usually comprises positively charged amino acids, (2) a hydrophobic region, and (3) a short carboxy-terminal peptide region. In eukaryotes, the signal peptide of a nascent precursor protein (pre-protein) directs the ribosome to the rough endoplasmic reticulum (ER) membrane and initiates the transport of the growing peptide chain across it. A signal peptide usually is not responsible for the final destination of the mature protein, but it is not limited in the present disclosure. Signal peptides are usually cleaved from precursor proteins by an endoplasmic reticulum (ER)-resident signal peptidase. They might remain uncleaved and function as a membrane anchor. In some embodiments, a signal peptide might be designed to fuse with the polypeptide or protein to be encoded by the payload at its C-terminus or N-terminus.

In some embodiments, the payload can be a therapeutic or prophylactic reagent for treating or preventing a disease (e.g., cancer or an infectious disease). For example, the payload can be an anti-viral agent, including but not limited to ribavirin, penciclovir, nitazoxanide, nafamostat, chloroquine, remdesivir (GS-5734) and favipiravir (T-705), interferon, adefovir, tenofovir, acyclovir, brivudin, cidofovir, fomivirsen, foscarnet, ganciclovir, amantadine, rimantadine, zanamivir, remdesivir, molnupiravir, and paxlovid. In other examples, the payload can be an anti-cancer agent. In certain embodiments, the payload is a nucleic acid configured to encode a therapeutic or prophylactic reagent.

In some embodiments, the N/P ratio (positively-chargeable polymer amine (N=nitrogen) groups to negatively-charged nucleic acid phosphate (P) groups) of the polymersome encapsulating a nucleic acid is about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45, or 50, or any range defined by the foregoing endpoints, include or exclude, such as 1 to 50, 1 to 40, 1 to 30, 1 to 20, 1 to 10, 1 to 5, 5 to 50, 5 to 40, 5 to 30, 5 to 20, 5 to 10, 10 to 50, 10 to 40, 10 to 30, 10 to 20, 8 to 40, 8 to 20, 8 to 12, 9 to 50, 9 to 30, or 9 to 15. In another embodiment, a polymersome encapsulating a mRNA has a nanoparticle/mRNA (N/P) ratio of about 10 or about 20.

In some embodiments where the payload of the polymersome is a nucleic acid configured to encode a polypeptide or protein in a target cell, after uptake by the target cell, the polymersome is configured to encode in vivo 1, 2, 3, 4, 5, 6, 7, 8, 9, 10, 15, 20, 25, 30, 35, 40, 45, or 50 copies of the polypeptide or protein, or any range defined by the foregoing endpoints, include or exclude, such as, 1 to 50, 1 to 40, 1 to 30, 1 to 20, 1 to 10, 1 to 5, 2 to 50, 2 to 40, 2 to 30, 2 to 20, 2 to 15, 2 to 10, 2 to 8, 2 to 6, 2 to 5, 2 to 4, 5 to 50, 5 to 40, 5 to 30, 5 to 20, 5 to 15, 5 to 10, 5 to 8, 4 to 50, 4 to 45, 4 to 35, 4 to 25, 4 to 15, 4 to 9, 4 to 6, 7 to 50, 7 to 45, 7 to 35, 7 to 25, 7 to 15, or 7 to 9 copies. In some embodiments, after uptake by the target cell, the polymersome is configured to encode in vivo the polypeptide or protein continually and instantly until the nucleic acid (i.e., the payload) is deactivated in vivo.

Compositions/Formulation

One aspect of the present disclosure is directed to a composition (i.e., a formulation) comprising the polymersome of the present disclosure. The polymersome of the composition might encapsulate a payload and is configured to deliver the payload to a target region of an organism. The payload can be as described herein, comprising a nucleic acid, a compound, a peptide, a protein, a glycan head, or a combination thereof. In some embodiments, the payload can be an immunogenic protein or a nucleic acid configured to encode the immunogenic protein in vivo. In some embodiments, the formulation further comprises a pharmaceutically acceptable excipient, adjuvant, or a combination thereof. In certain embodiments, the composition is a pharmaceutical composition or pharmaceutical formulation.

In some embodiments, the composition comprises 0.01, 0.05, 0.1, 0.5, 1, 2, 3, 4, 5, 10, 15, 20, 25, 30, 40, 50, 60, 70, 80, 90, 95% (w/w) the polymersome of the present disclosure, which encapsulates or does not encapsulate a payload, or any range defined by the foregoing endpoints, such as, included or excluded, 0.01% to 95% (w/w), 0.01% to 90% (w/w), 0.01% to 80% (w/w), 0.01% to 70% (w/w), 0.01% to 60% (w/w), 0.01% to 50% (w/w), 0.01% to 40% (w/w), 0.01% to 30% (w/w), 0.01% to 20% (w/w), 0.01% to 10% (w/w), 0.01% to 5% (w/w), 0.01% to 1% (w/w), 0.01% to 0.1% (w/w), 0.1% to 95% (w/w), 0.1% to 90% (w/w), 0.1% to 80% (w/w), 0.1% to 70% (w/w), 0.1% to 60% (w/w), 0.1% to 50% (w/w), 0.1% to 40% (w/w), 0.1% to 30% (w/w), 0.1% to 20% (w/w), 0.1% to 10% (w/w), 0.1% to 5% (w/w), 0.1% to 1% (w/w), 1% to 95% (w/w), 1% to 90% (w/w), 1% to 80% (w/w), 1% to 70% (w/w), 1% to 60% (w/w), 1% to 50% (w/w), 1% to 40% (w/w), 1% to 30% (w/w), 1% to 20% (w/w), 1% to 10% (w/w), 1% to 5% (w/w), 5% to 95% (w/w), 5% to 90% (w/w), 5% to 80% (w/w), 5% to 70% (w/w), 5% to 60% (w/w), 5% to 50% (w/w), 5% to 40% (w/w), 5% to 30% (w/w), 5% to 20% (w/w), or 5% to 10% (w/w). The rest of the percentages of the composition can be an excipient as described herein.

In some embodiments, the composition is an mRNA vaccine, wherein the polymersome encapsulates an mRNA configured to encode an immunogenic protein in vivo. The immunogenic protein can be a virus spike protein or other antigenic molecule of a pathogen. In certain embodiments, the composition of the present invention can be a COVID-19 mRNA vaccine.

An exemplary COVID-19 mRNA vaccine, as described herein, can be designed based on an mRNA technology to remove the glycan shields of a coronavirus (e.g., SARS-CoV-2) spike protein for better exposing the conserved regions of the spike protein. The mRNA vaccine of coronavirus spike protein has a deletion of glycosylation sites in the receptor binding domain (RBD) or the subunit 2 (S2) domain to expose highly conserved epitopes and elicit antibodies and CD8 T-cell response with broader protection against the alpha, beta, gamma, delta, omicron and various variants, as compared to the unmodified mRNA. The vaccine can be a Low Sugar Universal Vaccine (LSUV) as described in WO2022/221835, WO2022/221837A2 and US20200046826A1, which are herein incorporated by reference in their entirety.

In some embodiments, the composition of the present invention is configured for treating or preventing a disease (e.g., cancer). In such embodiments, the payload carried by the polymersome can be a therapeutic reagent, a prophylactic reagent, or a nucleic acid configured to encode the therapeutic reagent or the prophylactic reagent in vivo. For example, the composition can be a personalized cancer vaccine (e.g., melanoma), a KRAS vaccine (KRAS-driven), or a checkpoint vaccine (e.g., PD-1, PD-L1 related).

In some embodiments, the composition of the present invention can be administered together with another composition (e.g., a vaccine or a medicine). Examples of another composition can be, but are not limited to, influenza (flu) vaccine, adenovirus vaccine, anthrax vaccine, cholera vaccine, diphtheria vaccine, hepatitis A or B vaccine, HPV vaccine, measles vaccine, mumps vaccine, smallpox vaccine, rotavirus vaccine, tuberculosis vaccine, pneumococcal vaccine, and *Haemophilus influenzae* type b vaccine.

Combination Compositions

In some embodiments, the composition can be a combo composition (e.g., a combo vaccine) comprising a first polymersome encapsulating a first payload and a second polymersome encapsulating a second payload. The first polymersome and the second polymersome can be as the polymersomes described herein but are different from each other in terms of the structure or properties of the copolymers thereof. For example, wherein the first polymersome and the second polymersome are different in size, copolymers forming the membrane thereof, payload encapsulated within the polymersomes, or a combination thereof.

For example, the first polymersome comprises a glycan head configured to bind DC-SIGN, while the second polymersome comprises a glycan head configured to bind Siglec-1. In another example, the first polymersome comprises a glycan configured to target an antigen-presenting cell, while the second polymersome comprises a glycan configured to target a cancer cell.

In some embodiments, the first payload and the second payload are different from each other. For example, the first payload can be a protein or peptide, while the second payload can be a nucleic acid. In certain embodiments, the first payload and the second payload can both be mRNA molecules but encode different proteins. For example, the first payload can be a mRNA configured to encode a spike protein of delta-SARS-CoV2, while the second payload can be a mRNA configured to encode a spike protein of omicron-SARS-CoV2.

Additional Components of the Composition

In some embodiments, the composition of the present disclosure can further comprise an adjuvant and/or a non-active substance, such as a pharmaceutically acceptable excipient. In certain embodiments, the adjuvant can be but is not limited to C34, Gluco-C34, 7DW8-5, C17, C23, C30, α-galactosylceramide (α-GalCer), Aluminum salt (e.g., aluminum hydroxide, aluminum phosphate, alum (potassium aluminum sulfate), mixed aluminum salts), Squalene, MF59, QS-21, Freund's complete adjuvant, Freund's incomplete adjuvant, AS03 (GlaxoSmithKline), MF59 (Seqirus), CpG 1018 (Dynavax), or a combination thereof.

In certain embodiments, the pharmaceutically acceptable excipient might comprise a solvent, dispersion media, diluent, dispersion, suspension aid, surface active agent, isotonic agent, thickening or emulsifying agent, preservative, polymer, peptide, protein, cell, hyaluronidase, or mixtures thereof. Various excipients for formulating pharmaceutical compositions and techniques for preparing the composition are known in the art (see Remington: The Science and Practice of Pharmacy, 22$^{nd}$ Edition, Edited by Allen, Loyd V., Jr, Pharmaceutical Press). The use of a conventional excipient medium may be contemplated within the scope of the present disclosure, except insofar as any conventional excipient medium may be incompatible with a substance or its derivatives, such as by producing any undesirable biological effect or otherwise interacting in a deleterious manner with any other component(s) of the pharmaceutical composition. Formulation of standard pharmaceutically acceptable excipients may be carried out using routine methods in the pharmaceutical art (See Remington's Pharmaceutical Sciences, 19th Edition, Mack Publishing Company, Eastern Pennsylvania, USA.).

In some embodiments, the composition further comprises a phosphate conjugate. Without wishing to be bound by theories, the phosphate conjugate can increase in vivo circulation times and/or increase the targeted delivery of the polymersome of the present disclosure. Phosphate conjugates for use with the present disclosure may be made using the methods described in the PCT Publication No. WO2013/033438, filed on Aug. 30, 2012, or U.S. Publication No. US2013/0196948, filed on Jun. 23, 2011, the content of each of which is herein incorporated by reference in its entirety. As a non-limiting example, the phosphate conjugates may include a compound of any of the formulas described in the PCT Publication No. WO2013/033438, filed on Aug. 30, 2012, herein incorporated by reference in its entirety.

In some embodiments, the composition further comprises a conjugate to enhance the delivery of the polymersome of the present disclosure. Without wishing to be bound by theories, the conjugate selected to be used may inhibit the phagocytic clearance of the polymersome in a subject. In some examples, the conjugate may be a human membrane protein CD47 or a "self" peptide derived therefrom (e.g., the "self" particles described by Rodriguez et al. (Science 2013, 339, 971-975), herein incorporated by reference in its entirety).

In some embodiments where the payload is an immunogenic agent or a nucleic acid configured to encode the immunogenic agent, the composition further comprises an immunostimulatory agent to enhance the immune response induced by the immunogenic agent. As a non-limiting example, the composition may comprise a Th1 immunostimulatory agent, which may enhance a Th1-based response of the immune system (see PCT Publication No. WO2010/123569 and U.S. Publication No. 2011/0223201, each of which is herein incorporated by reference in its entirety).

In some embodiments, the composition does not include viral components (e.g., viral capsids, viral enzymes, or other viral proteins, for example, those needed for viral-based replication), nor is it packaged within, encapsulated within, linked to, or otherwise associated with a virus or viral particle.

Kit for Preparing a Polymersome

One aspect of the present disclosure is directed to a kit for preparing a polymersome of the present disclosure. The kit comprises a first reagent and a second reagent, wherein the first reagent comprises an initiator, comprising a glycan head and an initiator linking moiety, and the second reagent comprises a propagator, comprising a functional moiety and a propagator linking moiety, wherein the functional moiety comprises a guanidine group, a zwitterion group, a diethylene triamine, or a combination thereof; and wherein the initiator linking moiety is configured to couple with the propagator linking moiety via a linkage comprising a disulfide bond.

In some embodiments, the initiator linking moiety is configured to couple with the propagator linking moiety, thereby forming the linkage of the copolymer of the present disclosure. In some embodiments, the initiator linking moiety and the propagator linking moiety is independently a thiol group or a dithiolane group.

In some embodiments, the kit further comprises a reagent comprising a payload to be encapsulated by a polymersome prepared by using the kit of the present disclosure. In certain embodiments, the payload can be as described herein.

Initiator

The initiator comprises a glycan head and an initiator linking moiety. In some embodiments, the glycan head is described above in the initiator block of the copolymer of the present disclosure.

In some embodiments, the initiator molecule further comprises an initiator spacer, as described herein in the copolymer of the present disclosure. In certain embodiments, the initiator spacer comprises a saturated carbon moiety, a polyethylene glycol (PEG) moiety, or a combination thereof.

In some embodiments, the initiator is selected from a group consisting of:

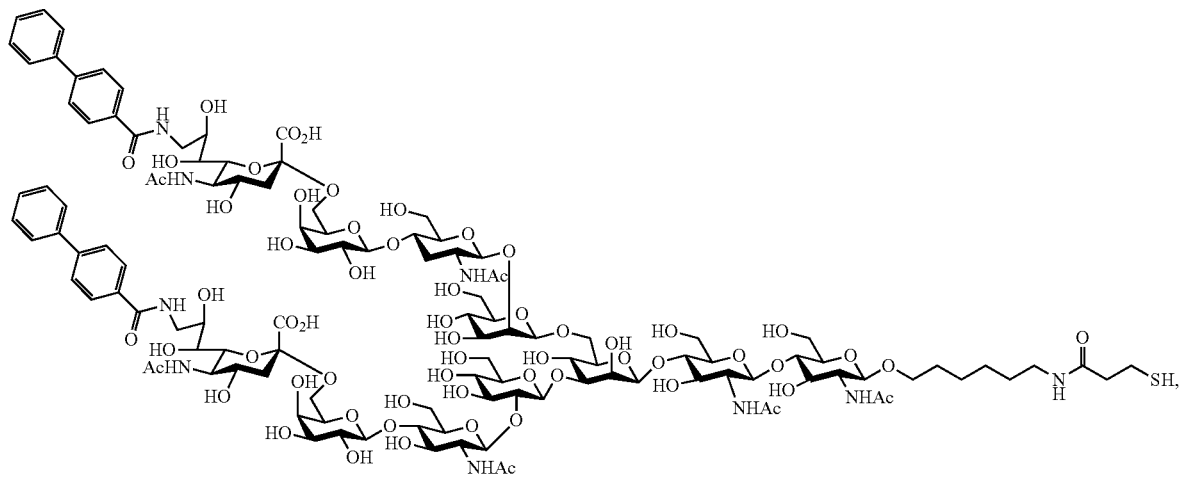
I2
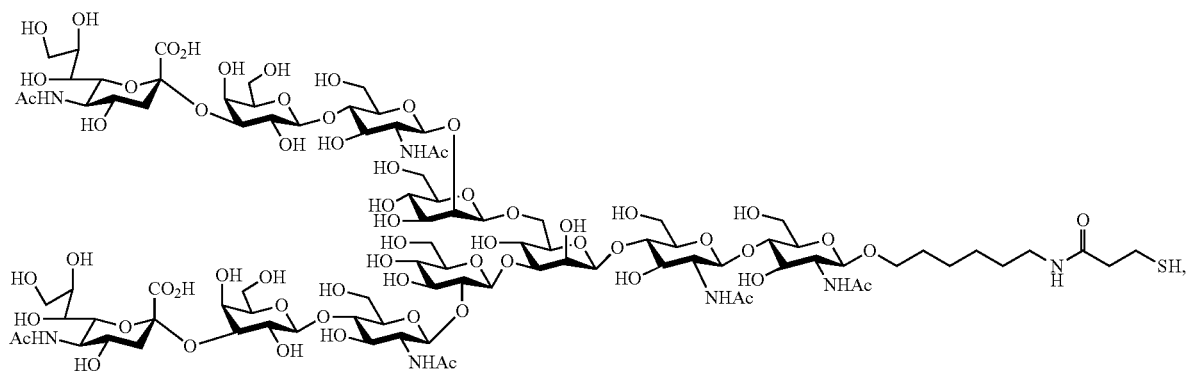
I3
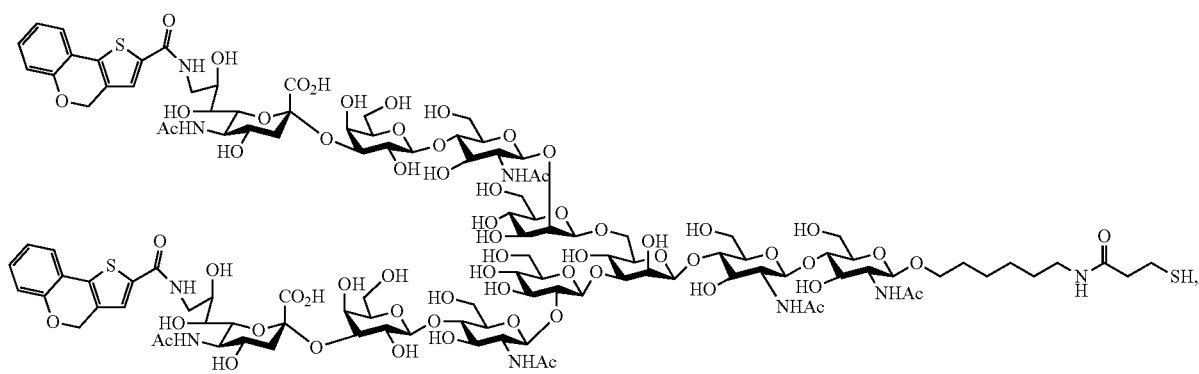
I4
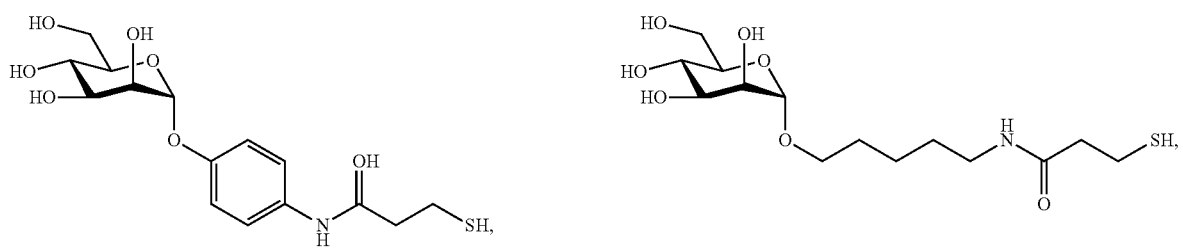
I5, I6

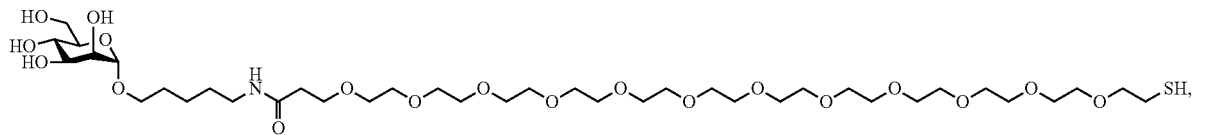

I7

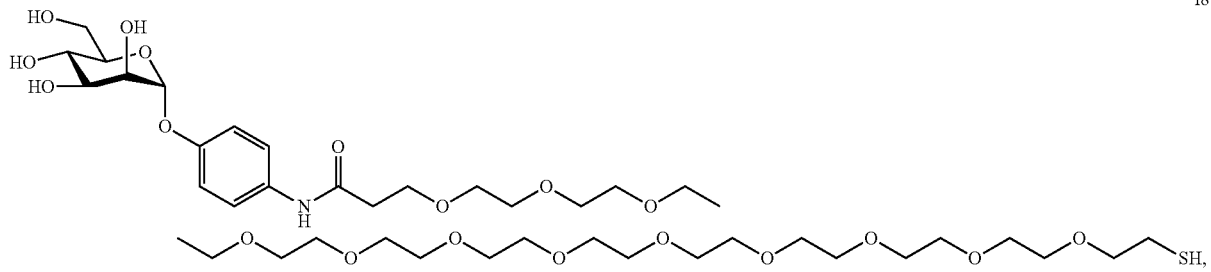

I8

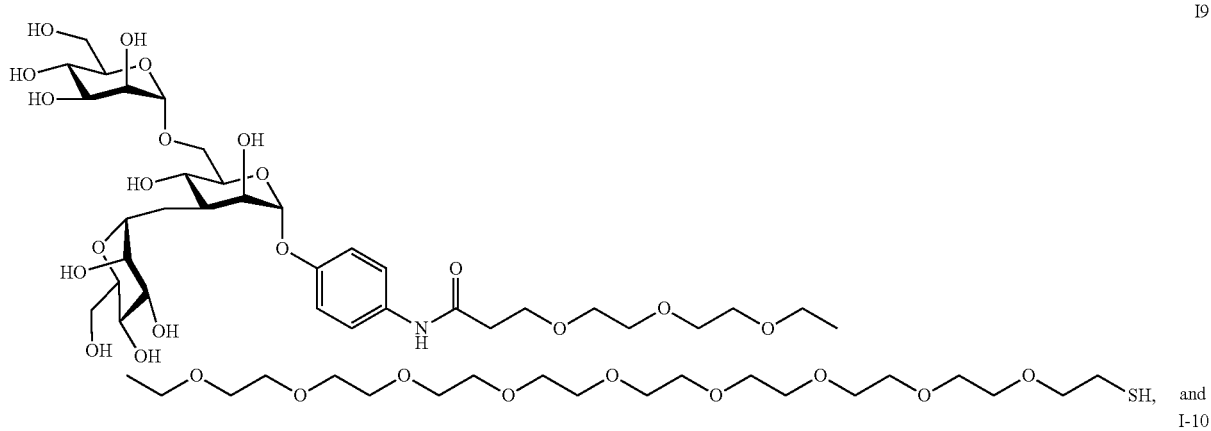

I9

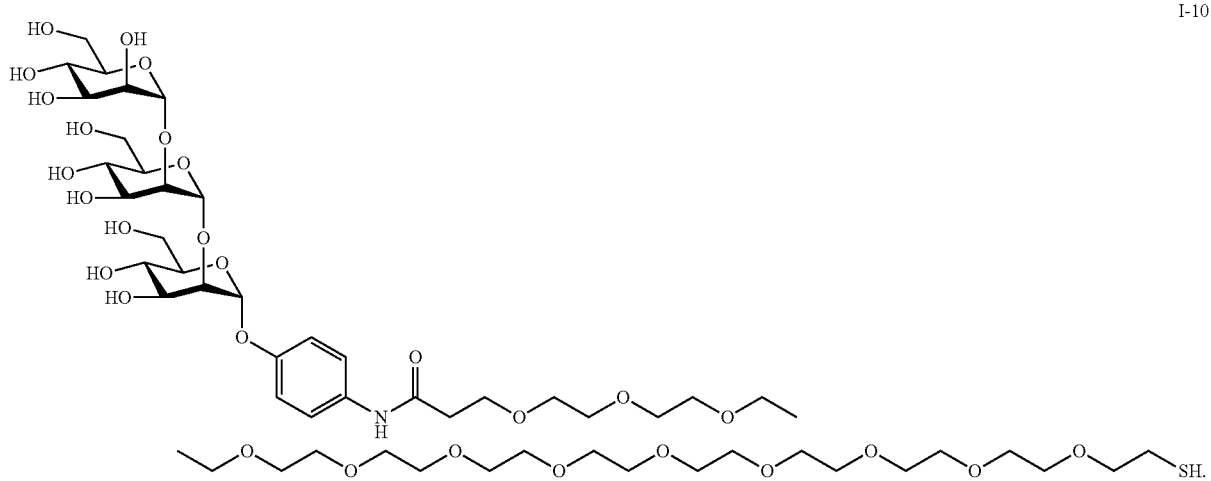

I-10

Propagator

The propagator comprises a functional moiety and a propagator linking moiety, wherein the functional moiety comprises a guanidine group, a zwitterion group, a diethylene triamine, or a combination thereof. In some embodiments, the functional moiety of the propagator molecule is as described above in the propagator block of the copolymer of the present disclosure.

In some embodiments, the propagator further comprises a propagator spacer, as described herein in the copolymer of the present disclosure. In certain embodiments, the propagator spacer comprises a saturated carbon moiety, a polyethylene glycol (PEG) moiety, or a combination thereof.

In some embodiments, the second reagent comprises two types of propagators, each being different from one another in structure or in the desired properties it provides. For example, the second reagent might comprise a first propagator and a second propagator, each independently comprising a functional moiety comprising a guanidine group, a zwitterion group, a diethylene triamine, or a combination thereof. In certain embodiments, the first propagator comprises the guanidine group, and the second propagator comprises the zwitterion group. In other embodiments, the first propagator comprises the guanidine group, and the second propagator comprises the diethylene triamine.

In some other embodiments, the kit further comprises a third reagent, comprising a propagator different from the propagator of the second reagent in structure or in the desired properties it provides. For example, the propagator of the second reagent is a first propagator molecule, and the third reagent comprises a second propagator. The first propagator and the second propagator might independently comprise a functional moiety comprising a guanidine group, a zwitterion group, a diethylene triamine, or a combination thereof. In certain embodiments, the first propagator comprises the guanidine group, and the second propagator comprises the zwitterion group. In other embodiments, the first propagator comprises the guanidine group, and the second propagator comprises the diethylene triamine.

In some embodiments, the propagator is selected from a group consisting of:

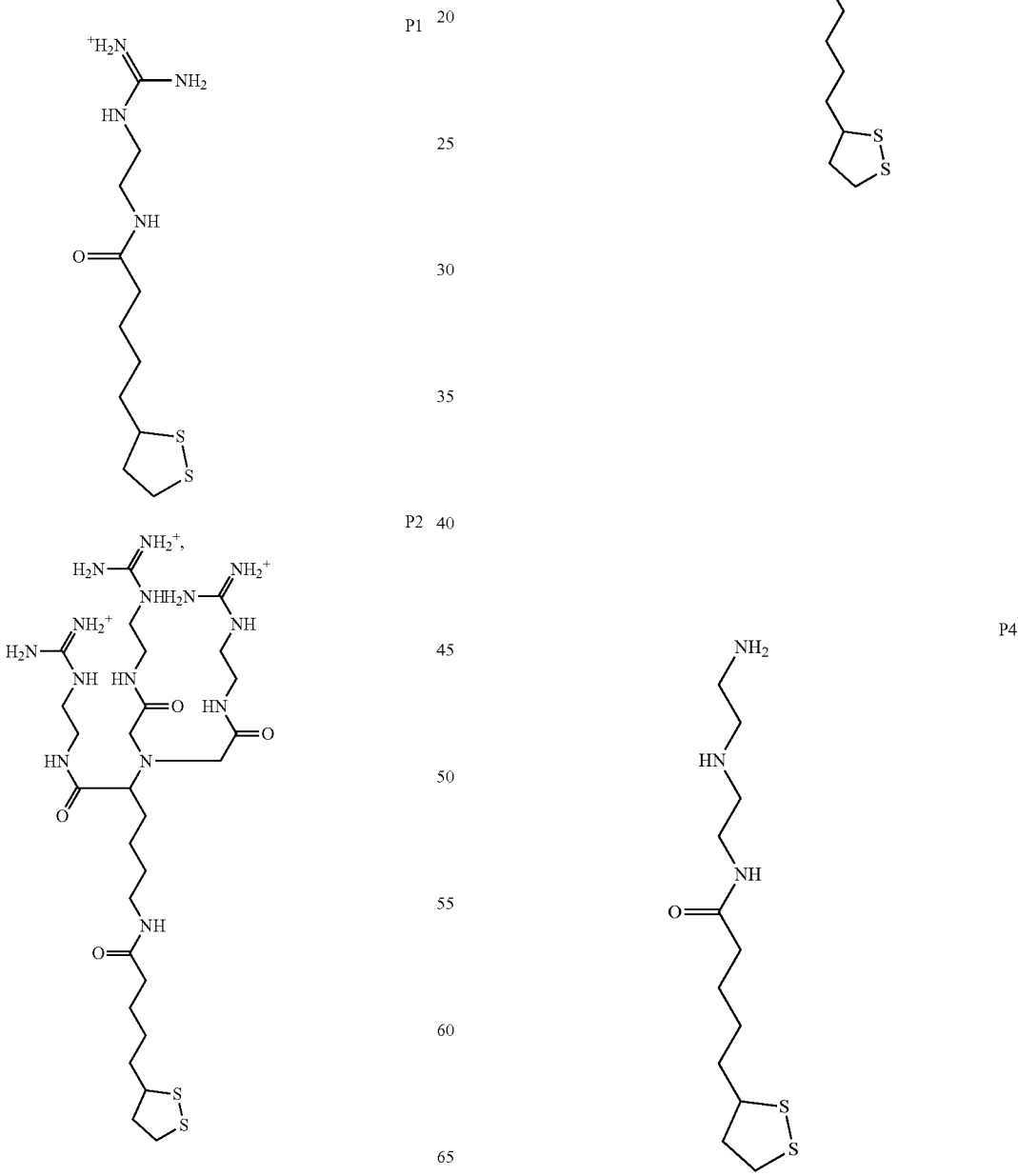

P5

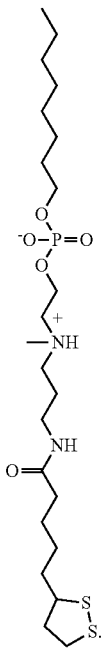

Packaging

All the components of the kit of the present disclosure can be packaged in a physical container, respectively. In some embodiments, the first reagent and the second reagent are contained in the same container; in other words, they are in a ready-to-use package. In some other embodiments, the first reagent and the second reagent are contained in separate containers so a user can decide whether and when to mix them.

Methods of Use

One aspect of the present disclosure is directed to methods of using the polymersome of the present disclosure. Particularly, the methods are conducted to obtain a desired effect, such as targeted delivering a payload, preventing or treating a disease, or boosting an adaptive immune response in a subject. In some embodiments, the subject can be but not limited to an animal or a human, to whom the payload is designed to exhibit its efficacy, to whom the treatment or prevention of disease is needed, or to whom the adaptive immune response thereof is required to be boosted.

Methods of Targeted Delivering a Payload in a Subject

In some embodiments, a method of targeted delivering a payload in a subject is provided, which comprises administering to the subject an effective amount of the polymersome of the present disclosure. In some embodiments, a method of targeted delivering a payload in a subject is provided, which comprises administering to the subject an effective amount of the pharmaceutical formulation of the present disclosure. The polymersome and the payload are as described herein, and the polymersome encapsulates the payload within an inner space defined by a membrane of the polymersome.

Without wishing to be bound by any theories, the targeted delivery is fulfilled by the initiator blocks of the copolymers forming the polymersome. Particularly, the initiator blocks provide the desired binding affinity/specificity targeting a desired region of the subject via the glycan head thereof.

Methods of Preventing or Treating a Disease in a Subject

In some embodiments, a method of preventing or treating a disease in a subject is provided, which comprises administering to the subject an effective amount of the polymersome of the present disclosure. The polymersome of this method encapsulates a payload within an inner space defined by a membrane of the polymersome, and the payload is a therapeutic agent or derives a therapeutic agent configured to prevent and/or treat the disease.

Without wishing to be bound by any theories, the polymersome of the present disclosure provides targeted delivery via the glycan heads of the copolymers thereof. Therefore, by using the polymersome of the present disclosure to deliver the payload, the efficacy of the payload can be more effectively performed. For example, in the embodiments that the glycan head comprises a structure binding specifically to the DC-SIGN on dendritic cells, an antigenic or immunogenic payload can be effectively delivered to the dendritic cells to provoke immune responses for preventing a disease of concern. This strategy is beneficial in delivering an antigen or a nucleic acid encoding an antigen of a vaccine. Some other examples include having a glycan head designed to target cancer cells so that an anti-tumor reagent can be delivered effectively to a cancer microenvironment. This strategy can increase the efficacy of the anti-tumor reagent and reduce the treatment's side effects.

In some embodiments, the disease is characterized by dysfunctional or aberrant protein or polypeptide activity. For example, the disease is selected from the group consisting of rare diseases, infectious diseases, cancer and proliferative diseases, genetic diseases (e.g., cystic fibrosis), autoimmune diseases, diabetes, neurodegenerative diseases, cardio- and reno-vascular diseases, and metabolic diseases.

In some embodiments, the disease can be cancer or infectious diseases. In certain embodiments, the disease can be a viral-associated infection, including, but not limited to, human parainfluenza virus 3, respiratory syncytial virus (RSV), cytomegalovirus (CMV), human metapneumovirus (hMPV), or SARS-CoV-2 (COVID-19) associated infections.

Methods of Boosting an Adaptive Immune Response

In some embodiments, a method of boosting an adaptive immune response is provided, comprising administering to a subject an effective amount of a polymersome of the present disclosure. The polymersome of this method encapsulates a payload within an inner space defined by a membrane of the polymersome, and the payload is a therapeutic agent or derives a therapeutic agent configured to provoke an adaptive immune response in the subject.

Without wishing to be bound by any theories, the polymersome of the present disclosure provides targeted delivery to an immune cell via the glycan heads of the copolymers thereof. In some embodiments, the glycan head comprises a structure that binds to an antigen-presenting cell with the desired specificity or affinity. For example, the glycan head might comprise a structure binding specifically to the DC-SIGN on dendritic cells so that the polymersome is able to deliver the immunogenic payload specifically to the dendritic cells to facilitate the onset of an adaptive immune response.

In some embodiments, the boosted adaptive immune response is against a disease, including but not limited to cancer or an infectious disease. The infectious disease, for example, can be a viral-associated infection, including, but not limited to, human parainfluenza virus 3, respiratory syncytial virus (RSV), cytomegalovirus (CMV), human metapneumovirus (hMPV), or SARS-CoV-2 (COVID-19) associated infections.

Administration

Regarding the methods of the present disclosure, in some embodiments, the subject is administered with a single dose of the polymersome or formulation of the present disclosure, which encapsulates or does not encapsulate a payload. Yet in some embodiments, the subject is administered with the polymersome in an initial dose followed by at least one booster dose, e.g., one, two, three, four, five, six, seven, eight, nine, ten, eleven, twelve, thirteen, fourteen, fifteen, sixteen, seventeen, eighteen, nineteen, twenty, or more follow-up doses, with an interval of each dose in about, 1, 2, 3, 4, 5, 6, 7 days, about 1, 2, 3, 4, 5, 6, 7, 8, 9, or 10 weeks, or about 1, 2, 3, 4, 5, 6, 7, 8, 9, 10, 11, or 12 months, or any range defined by the foregoing endpoints, such as, included or excluded, 1 to 7 days, 1 to 5 days, 1 to 3 days, 1 to 10 weeks, 1 to 8 weeks, 1 to 6 weeks, 1 to 4 weeks, 1 to 2 weeks, 1 to 12 months, 1 to 8 months, 1 to 6 months, 1 to 4 months, 1 to 2 months, or 6 to 12 months. In certain embodiments, the polymersome of the present disclosure encapsulating a payload is administered twice at the same or different doses, and the two administrations are separated by 1 day, 3 days, 5 days, 1 week, 2 weeks, 1 month, 2 months, 3 months, 6 months, 1 year, 1 to 5 days, 1 to 2 weeks, 1 to 3 months, 1 to 6 months, 1 month to 1 year, 3 months to 1 year, or 6 months to 1 year.

Administration Route.

The polymersome or composition as described herein may be administered by any route. Suitable routes include but are not limited to, oral, nasal, mucosal, submucosal, intravenous, intramuscular, intraperitoneal, subcutaneous, intradermal, transdermal, and buccal routes. Some practical topical applications include but are not limited to, a drop, spray, aerosol, gel, or ointment to the mucosal epithelium of the eye, nose, mouth, anus, or vagina. Other possible routes of administration are by spray, aerosol, or powder application through inhalation via the respiratory tract.

Effective Amount of Administration.

The effective amount described herein refers to the amount sufficient to provide a desired effect. In the embodiments where the purpose of administering the polymersome of the present disclosure is to treat a disease, the effective amount refers to a therapeutically effective amount, while in some other embodiments where the purpose is to prevent a disease, the effective amount refers to a prophylactically effective amount.

Yet in some other embodiments where the purpose of administering the polymersome with payload is to boost an adaptive immune response, the effective amount can be determined as an amount sufficient to induce an antigen-specific immune response in a subject to whom the polymersome and payload are administered. The antigen-specific immune response can be characterized by measuring an anti-antigenic polypeptide (i.e., the payload or the product of the payload) antibody titer produced in a subject to whom the polymersome and payload are administered. In some embodiments, the measurement can be conducted using an Enzyme-linked immunosorbent assay (ELISA).

In some embodiments, an antibody titer is used to assess whether a subject has had an infection or to determine whether immunizations are required. In some embodiments, an antibody titer is used to determine the strength of an autoimmune response, to determine whether a booster immunization is needed or whether an immunization has been boosted, to determine whether a previous vaccine was effective, and/or to identify any recent or prior infections.

The effective amount of the methods of the present disclosure can be determined based on several factors, including but not limited to the conditions of the subjects (age, gender, species, body weight, health status, etc.), the progress of the disease to be treated, the administration route, the dosage and interval of the administration, and the nature of the payload. Regarding the nature of the payload, for example, in embodiments where the polymersome of the present disclosure is used to carry an mRNA as in an mRNA vaccine, the effective amount can be determined based on the effective amount of the mRNA required to provoke sufficient immune response in the subject. Accordingly, in some embodiments that the payload is mRNA, the effective amount of the methods of the present disclosure is about 5, 10, 15, 20, 25, 30, 35, 40, 45, 50, 55, 60, 65, 70, 75, 80, 90, 100, 125, 150, 175, 200, 250, 300, 350, 400, 450, 500, 550, 600, 650, 700, 750, 800, 850, 900, 950 or 1000 micrograms (μg or ug), or any range defined by the foregoing endpoints, such as, include or exclude, 5 micrograms to 1000 micrograms, 5 micrograms to 900 micrograms, 5 micrograms to 800 micrograms, 5 micrograms to 700 micrograms, 5 micrograms to 600 micrograms, 5 micrograms to 500 micrograms, 5 micrograms to 400 micrograms, 5 micrograms to 300 micrograms, 5 micrograms to 200 micrograms, 5 micrograms to 175 micrograms, 5 micrograms to 150 micrograms, 5 micrograms to 125 micrograms, 5 micrograms to 100 micrograms, 5 micrograms to 90 micrograms, 5 micrograms to 80 micrograms, 5 micrograms to 70 micrograms, 5 micrograms to 60 micrograms, 5 micrograms to 50 micrograms, 5 micrograms to 40 micrograms, 5 micrograms to 30 micrograms, 5 micrograms to 20 micrograms, 5 micrograms to 10 micrograms, 10 micrograms to 1000 micrograms, 10 micrograms to 900 micrograms, 10 micrograms to 800 micrograms, 10 micrograms to 700 micrograms, 10 micrograms to 600 micrograms, 10 micrograms to 500 micrograms, 10 micrograms to 400 micrograms, 10 micrograms to 300 micrograms, 10 micrograms to 200 micrograms, 10 micrograms to 175 micrograms, 10 micrograms to 150 micrograms, 10 micrograms to 125 micrograms, 10 micrograms to 100 micrograms, 10 micrograms to 90 micrograms, 10 micrograms to 80 micrograms, 10 micrograms to 70 micrograms, 10 micrograms to 60 micrograms, 10 micrograms to 50 micrograms, 10 micrograms to 40 micrograms, 10 micrograms to 30 micrograms, 10 micrograms to 20 micrograms, 50 micrograms to 1000 micrograms, 50 micrograms to 900 micrograms, 50 micrograms to 800 micrograms, 50 micrograms to 700 micrograms, 50 micrograms to 600 micrograms, 50 micrograms to 500 micrograms, 50 micrograms to 400 micrograms, 50 micrograms to 300 micrograms, 50 micrograms to 200 micrograms, 50 micrograms to 175 micrograms, 50 micrograms to 150 micrograms, 50 micrograms to 125 micrograms, 50 micrograms to 100 micrograms, 50 micrograms to 90 micrograms, 50 micrograms to 80 micrograms, 50 micrograms to 70 micrograms, or 50 micrograms to 60 micrograms. 100 micrograms to 1000 micrograms, 100 micrograms to 900 micrograms, 100 micrograms to 800 micrograms, 100 micrograms to 700 micrograms, 100 micrograms to 600 micrograms, 100 micrograms to 500 micrograms, 100 micrograms to 400 micrograms, 100 micrograms to 300 micrograms, 100 micrograms to 200 micrograms, 100 micrograms to 175 micrograms, 100 micrograms to 150 micrograms, 300 micrograms to 1000 micrograms, 300 micrograms to 900 micrograms, 300 micrograms to 800 micrograms, 300 micrograms to 700 micrograms, 300 micrograms to 600 micrograms, 300 micrograms to 500 micrograms, 300 micrograms to 400 micrograms, 500 micrograms to 1000 micrograms, 500 micrograms to 900 micrograms, 500 micrograms to 800 micrograms, 500 micrograms to 700 micrograms, 500 micrograms to 600 micrograms, 600 micrograms to 800 micrograms, or 700 micrograms to 900 micrograms.

Nevertheless, given the targeted delivery provided by the polymersome of the present disclosure, one can expect that the effective amount required in the methods of the present disclosure might be lower than the effective amount required in other non-targeted delivery methods. For example, the effective amount required in the methods of the present disclosure might be lower than the effective amount required in other non-targeted delivery methods by at least 1, 2, 3, 4, 5, 6, 7, 8, 9, 10, 15, 20, 25, 30, 35, 40, 45, 50, 60, 70, 80, 90, 95, or 99%, or any range defined by the foregoing endpoints, such as, included or excluded, 1 to 99%, 1 to 95%, 1 to 90%, 1 to 80%, 1 to 70%, 1 to 60%, 1 to 50%, 1 to 40%, 1 to 30%, 1 to 20%, 1 to 10%, 1 to 5%, 5 to 99%, 5 to 95%, 5 to 90%, 5 to 80%, 5 to 70%, 5 to 60%, 5 to 50%, 5 to 40%, 5 to 30%, 5 to 20%, 5 to 10%, 10 to 90%, 10 to 80%, 10 to 70%, 10 to 60%, 10 to 50%, 10 to 40%, 10 to 30%, 10 to 20%, 30 to 99%, 30 to 95%, 30 to 90%, 30 to 80%, 30 to 70%, 30 to 60%, 30 to 50%, 30 to 40%, 50 to 99%, 50 to 95%, 50 to 90%, 50 to 80%, 50 to 70%, 50 to 60%, 70 to 99%, 70 to 95%, 70 to 90%, 70 to 80%, 80 to 99%, 80 to 95%, 80 to 90%, 90 to 99%, or 95 to 99%.

Furthermore, in some embodiments where the polymersome of the present disclosure is used to deliver an antigenic agent or a nucleic acid encoding the antigenic agent to induce antibodies against the antigenic agent, the titer of the antibody induced by the present disclosure, compared with the titer of the antibody induced by non-targeted delivery methods, increase 1, 2, 3, 4, 5, 6, 7, 8, 9, or 10 logs, or any range defined by the foregoing endpoints, such as, included or excluded 1 to 10 logs, 1 to 8 logs, 1 to 6 logs, 1 to 4 logs, 2 to 9 logs, 2 to 7 logs, 2 to 5 logs, 3 to 10 logs, 3 to 8 logs, 3 to 5 logs, or 4 to 6 logs.

In some other embodiments, where the polymersome of the present disclosure is used to deliver an antigenic agent or a nucleic acid encoding the antigenic agent to induce an immune response against the antigenic agent, the antibody titer against the antigenic agent induced by the present disclosure, compared with that of non-targeted delivery methods, is 0.1, 0.2, 0.5, 1, 2, 3, 4, 5, 6, 7, 8, 9, or 10 times higher, or any range defined by the foregoing endpoints, such as, included or excluded, 0.1 to 10, 0.1 to 9, 0.1 to 8, 0.1 to 7, 0.1 to 6, 0.1 to 5, 0.1 to 4, 0.1 to 3, 0.1 to 2, 0.1 to 1, 0.1 to 0.5, 0.5 to 10, 0.5 to 9, 0.5 to 8, 0.5 to 7, 0.5 to 6, 0.5 to 5, 0.5 to 4, 0.5 to 3, 0.5 to 2, 0.5 to 1, 1 to 10, 1 to 9, 1 to 8, 1 to 7, 1 to 6, 1 to 5, 1 to 4, 1 to 3, 1 to 2, 3 to 10, 3 to 9, 3 to 8, 3 to 7, 3 to 6, 3 to 5, 3 to 4, 5 to 10, 5 to 9, 5 to 8, 5 to 7, 5 to 6, 7 to 10, 7 to 9, 7 to 8, or 8 to 10.

Yet in some embodiments where the polymersome of the present disclosure is used to deliver an antigenic agent or a nucleic acid encoding the antigenic agent to induce an immune response against the antigenic agent, the immune response is induced 1, 2, 3, 4, 5, 6, 7, 8, 9, 10, 12, 14, 16, 18, or 20 days earlier than the immune response induced by non-targeted delivery methods, or any range defined by the foregoing endpoints, such as, included or excluded, 1 to 20, 1 to 18, 1 to 14, 1 to 10, 1 to 6, 2 to 20, 2 to 18, 2 to 14, 2 to 10, 2 to 6, 5 to 20, 5 to 18, 5 to 14, or 5 to 10 days earlier.

In some embodiments, the polymersome as described herein in the methods of the present disclosure is administered at a dosage level sufficient to deliver a payload from about 0.0001 mg/kg to about 100 mg/kg, from about 0.001 mg/kg to about 0.05 mg/kg, from about 0.005 mg/kg to about 0.05 mg/kg, from about 0.001 mg/kg to about 0.005 mg/kg, from about 0.05 mg/kg to about 0.5 mg/kg, from about 0.01 mg/kg to about 50 mg/kg, from about 0.1 mg/kg to about 40 mg/kg, from about 0.5 mg/kg to about 30 mg/kg, from about 0.01 mg/kg to about 10 mg/kg, from about 0.1 mg/kg to about 10 mg/kg, or from about 1 mg/kg to about 25 mg/kg, per subject body weight per day, one or more times a day, to obtain the desired in vivo effect.

Definition

Unless specifically defined otherwise, all technical and scientific terms used herein have the same meaning as commonly understood by one of ordinary skill in the art to which this disclosure belongs. Unless mentioned otherwise, the techniques employed or contemplated herein are standard methodologies well known to one of ordinary skill in the art. The practice of the present disclosure will employ, unless otherwise indicated, conventional techniques of microbiology, tissue culture, molecular biology, chemistry, biochemistry, and recombinant DNA technology, which are within the skill of the art. The materials, methods, and examples are illustrative only and not limiting. The following is presented by way of illustration and is not intended to limit the scope of the disclosure.

Numbers expressing quantities of ingredients, properties such as molecular weight, reaction conditions and results, and so forth, used to describe and claim certain embodiments of the present disclosure are to be understood as being modified in some instances by the term "about." A skilled artisan in the field would understand the meaning of the term "about" in the context of the value that it qualifies. The numerical values presented in some embodiments of the present disclosure may contain certain errors resulting from the standard deviation in their respective testing measurements. For example, the term "about," as used herein, refers to a measurable value such as an amount, a temporal duration, and the like and is meant to encompass variations of ±20%, ±10%, ±5%, ±1%, or ±0.1% from the specified value, as such variations are appropriate.

As used herein, "substantially" means sufficient to work for the intended purpose. The term "substantially" thus allows for minor, insignificant variations from an absolute or perfect state, dimension, measurement, result, or the like, such as expected by a person of ordinary skill in the field, but that does not appreciably affect overall performance. When used with respect to numerical values or parameters or characteristics expressed as numerical values, "substantially" means within ten percent.

As used herein, "treat," "treatment," and "treating" refer to an approach for obtaining beneficial or desired results, for example, clinical results. For this disclosure, beneficial or desired results may include inhibiting or suppressing the initiation or progression of an infection or a disease; ameliorating, or reducing the development of, symptoms of an infection or disease; or a combination thereof.

As used herein, "preventing" and "prevention" are used interchangeably with "prophylaxis" and can mean complete prevention of infection or prevention of the development of symptoms of that infection, a delay in the onset of a disease or its symptoms; or a decrease in the severity of a subsequently developed infection or its symptoms.

As used herein, "glycan" refers to a polysaccharide, oligosaccharide, or monosaccharide. Glycans can be monomers or polymers of sugar residues and can be linear or branched. A glycan may include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6' sulfo N-acetylglucosamine, etc.).

EXAMPLE

Example 1: Synthesis of Exemplary Polymersomes

Chemical Materials and Methods

For chemical synthesis, all starting materials and commercially obtained reagents were purchased from Sigma-Aldrich and used as received unless otherwise noted. All reactions were performed in oven-dried glassware under a nitrogen atmosphere using dry solvents. $^1$H and $^{13}$C NMR spectra were recorded on Brucker AV-600 spectrometer, and were referenced to the solvent used (CDCl$_3$ at δ 7.24 and 77.23, CD$_3$OD at δ 3.31 and 49.2, and D$_2$O at δ 4.80, and DMSO-d$_6$ at δ 2.5 and 39.51 for $^1$H and $^{13}$C, respectively). Chemical shifts (δ) are reported in ppm using the following convention: chemical shift, multiplicity (s=singlet, d=doublet, t=triplet, q=quartet, m=multiplet), integration, and coupling constants (J), with J reported in Hz. High-resolution mass spectra were recorded under ESI-TOF mass spectroscopy conditions. Silica gel (E, Merck) was used for flash chromatography. IMPACT™ system (Intein Mediated Purification with Affinity Chitinbinding Tag) was purchased from New England Biolabs. His-tag purification resin was purchased from Roche. HiTrap IMAC column (5 mL) was purchased from GE Healthcare Life Sciences. Gel permeation chromatography (GPC) equipped with Ultimate 3000 liquid chromatography associated with a 101 refractive index detector and Shodex columns was used to analyze the polymeric products using THF as the eluent at 30° C. with 1 mL min$^{-1}$ flow rate. The calibration was based on the narrow linear poly(styrene) Shodex standard (SM-105). The Mw and dispersity of the polymeric products were calculated using DIONEX chromeleon software. Transmission electron microscopy (TEM) images were obtained by a FEI Tecnai G2 F20 S-Twin.

The chemical materials and methods described herein apply to all examples described in the present disclosure.
Preparation of the Exemplary Propagator of the Present Disclosure Five exemplary propagators, Propagator P1, P2, P3, P4, and P5, were described herein. The preparation process for Propagator P1 (Compound 2), P2 (Compound 3), and P4 (Compound 8) is illustrated in Scheme 1 below. Propagator P3 (Compound 11) was prepared according to Scheme 2 below. Propagator P5 (Compound 14) was prepared according to Scheme 3 below. The compounds obtained in each step of the schemes were verified by NMR. Additional details and the data are described below.

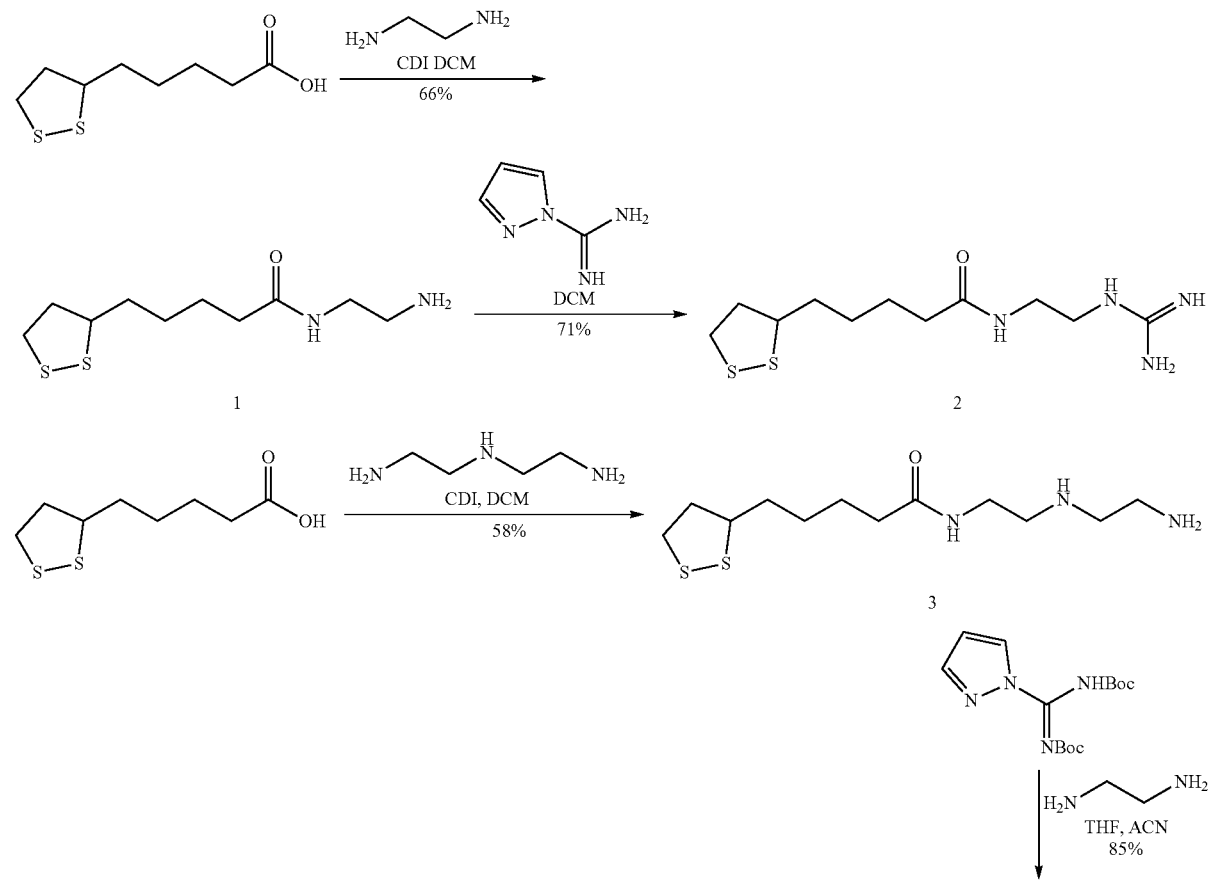

-continued
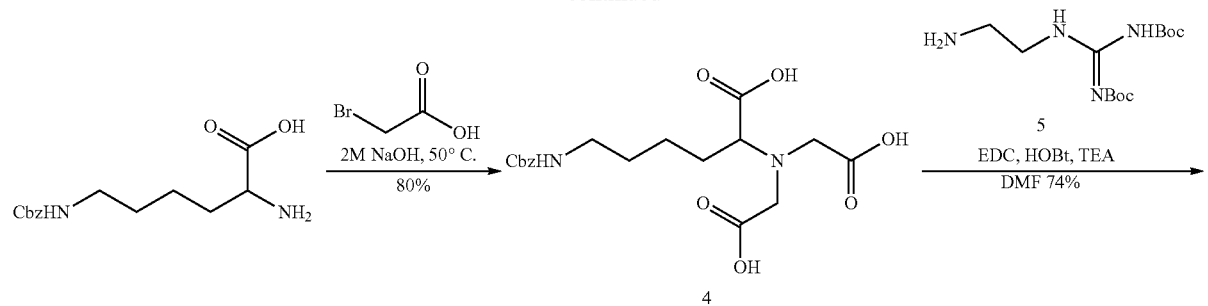
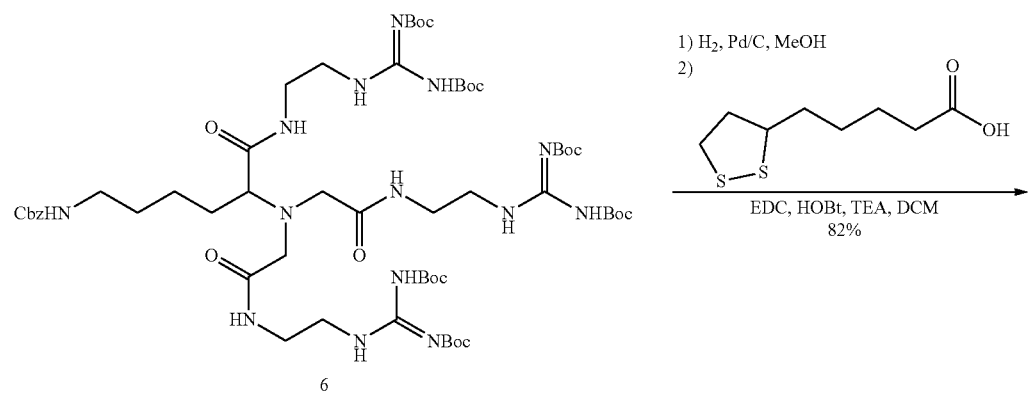
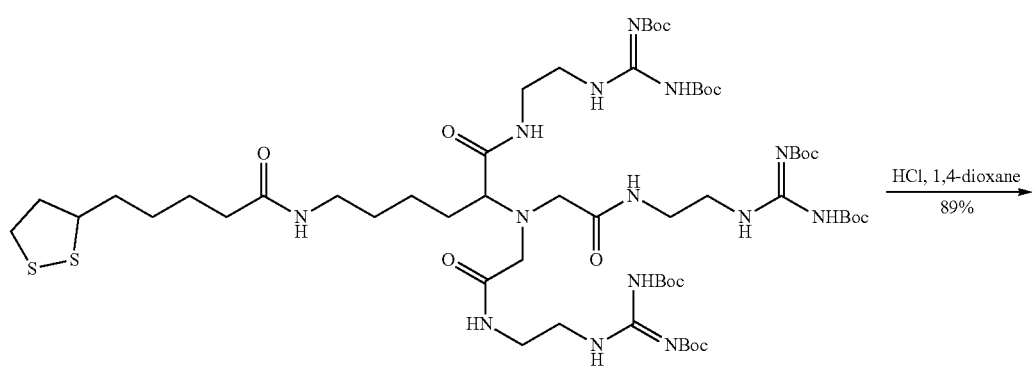
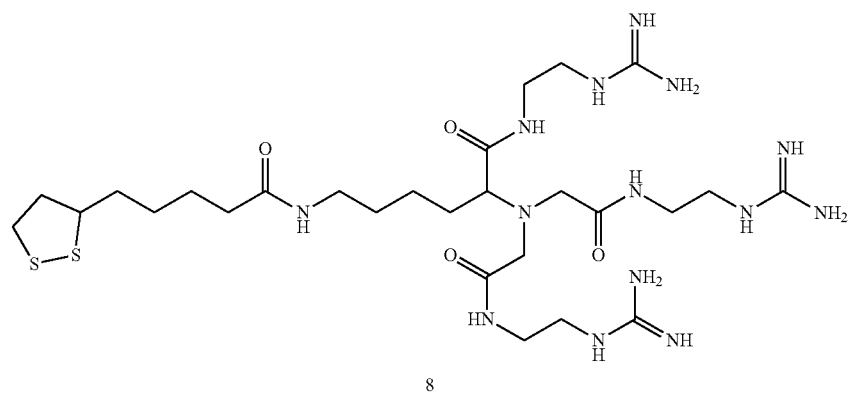

Scheme 2
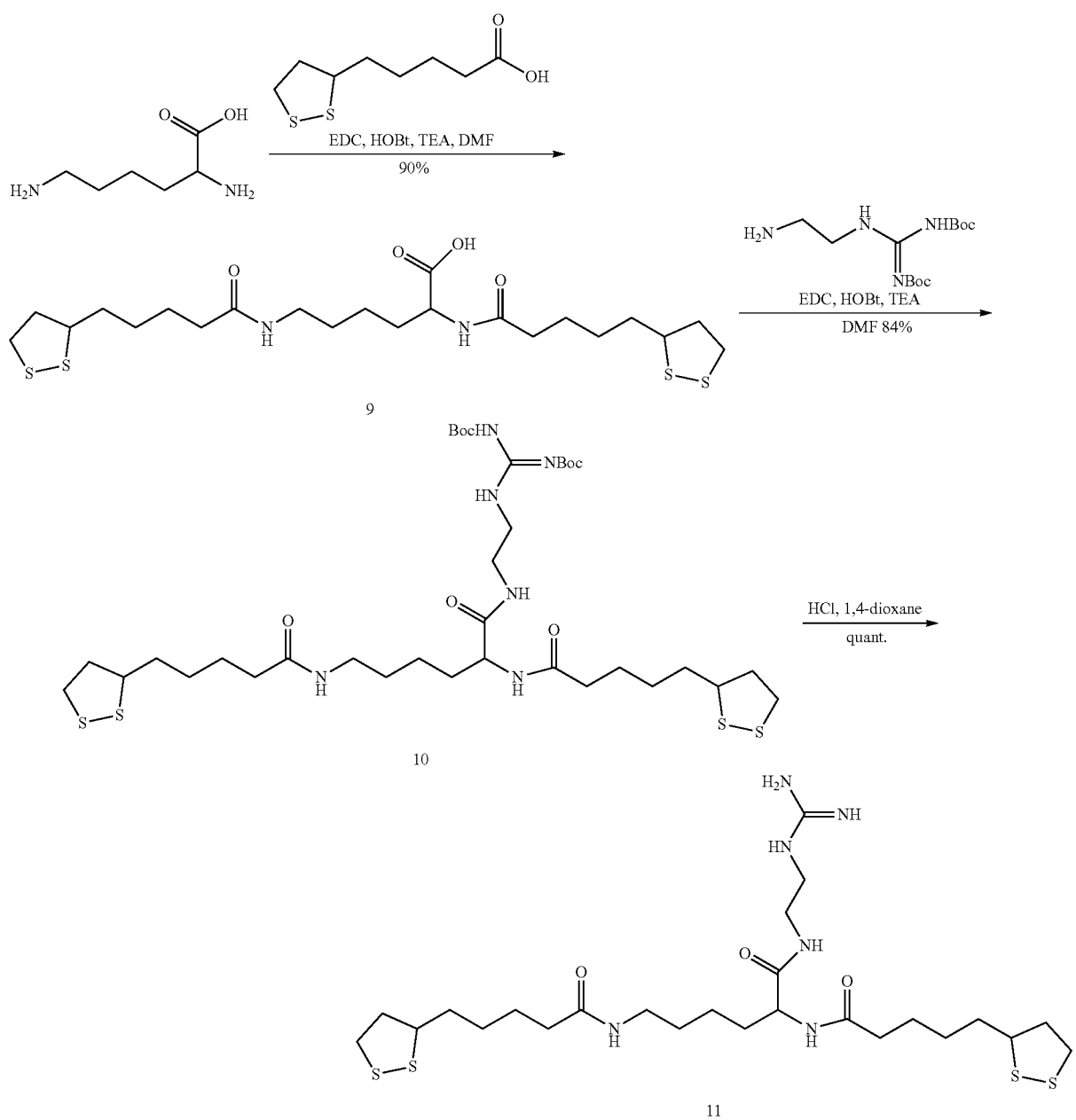
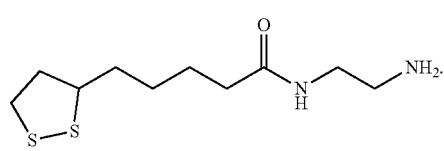
Compound 1
Compound 1 was synthesized and characterized based on a published procedure. 1H NMR (600 MHz, CDCl$_3$): δ 5.92 (br, 1H), 3.60-3.57 (m, 1H), 3.29 (dt, J=11.2 Hz, 2H), 3.21-3.10 (m, 2H), 2.86-2.79 (m, 2H), 2.55-2.31 (m, 1H), 2.21 (t, 2H, J=7.4 Hz), 1.90-1.85 (m, 1H), 1.77-1.41 (m, 8H). The synthesis was performed according to Jiaqi Fu et al., *Journal of the American Chemical Society* 2015 137 (37), 12153-12160, which is herein incorporated by reference in its entirety.
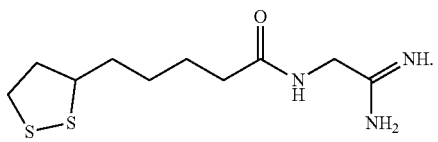
Compound 2

Compound 2 was synthesized and characterized based on a published procedure. $^1$H NMR (600 MHz, MeOD): δ 3.98 (s, 1H), 3.61-3.39 (m, 1H), 3.30-3.22 (m, 4H), 3.22-2.88 (m, 2H), 2.56-2.30 (m, 1H), 2.21 (t, J=7.4 Hz, 2H), 1.98-1.72 (m, 1H), 1.79-1.30 (m, 6H). The synthesis was performed according to Jiaqi Fu et al., *Journal of the American Chemical Society* 2015 137 (37), 12153-12160, which is herein incorporated by reference in its entirety.

Compound 3

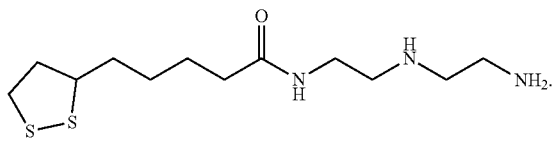

Compound 3 was synthesized and characterized based on a published procedure. $^1$H NMR (600 MHz, CDCl$_3$): δ 3.61-3.56 (m, 1H), 3.41-3.34 (m, 1H), 3.31-3.16 (m, 8H), 3.14-3.06 (m, 2H), 2.54-2.40 (m, 1H), 2.08 (t, J=7.4 Hz, 2H), 1.95-1.86 (m, 1H), 1.69 (s, 1H), 1.55 (m, 3H), 1.47-1.31 (m, 2H). The synthesis was performed according to Guo, J. et al., Rational Design of Poly(disulfide)s as a Universal Platform for Delivery of CRISPR-Cas9 Machineries toward Therapeutic Genome Editing. *ACS Central Science* 2021, 7, 990-1000, which is herein incorporated by reference in its entirety.

Compound 4

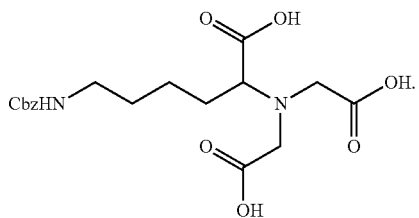

Compound 4 was synthesized and characterized according to a published protocol. $^1$H NMR (600 MHz, DMSO-d$_6$): δ 7.44-7.12 (m, 5H), 5.02 (s, 2H), 3.62-3.41 (m, 4H), 3.35 (t, 1H, J=7.2 Hz), 2.98 (d, 2H, J=5.9 Hz), 1.79-1.03 (m, 6H). The synthesis was performed according to Jiaqi Fu et al., *Journal of the American Chemical Society* 2015 137 (37), 12153-12160, which is herein incorporated by reference in its entirety.

Compound 5

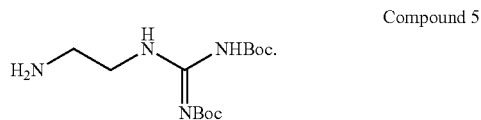

Compound 5 was synthesized and characterized according to a published protocol. $^1$H NMR (600 MHz, CDCl$_3$): δ 11.52 (br, 1H), 8.62 (s, 1H), 3.45 (q, J=4.00 Hz, 2H), 2.86 (t, J=4.00 Hz, 2H), 1.49 (s, 9H), 1.48 (s, 9H). The synthesis was performed according to Kuppusamy, R. et al., Design and synthesis of short amphiphilic cationic peptidomimetics based on biphenyl backbone as antibacterial agents. *Eur. J. Med. Chem.* 2018, 143, 1702-1722, which is herein incorporated by reference in its entirety.

Compound 6

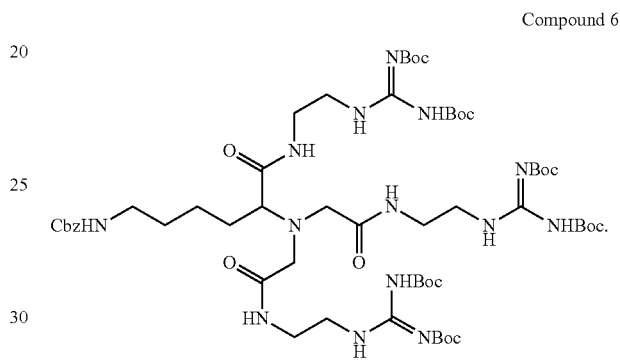

A solution of 4 (0.126 mmol) in DMF (1 mL) was preactivated with EDC (0.506 mmol), HOBt (0.506 mmol), and trimethylamine (0.57 mmol) under nitrogen for 30 min. 5 (0.506 mmol) in DMF (1 mL) was then added to the above solution and the resulting solution was stirred at rt for 12 h. The mixture was concentrated to dryness in vacuo and then diluted with ethyl acetate. The organic layer was washed with H$_2$O three times and dried over MgSO$_4$, filtered, and concentrated. The crude product was purified by column chromatography on silica gel (MeOH/DCM 1:20) to yield 6 (134 mg, 74%). $^1$H NMR (600 MHz, CDCl$_3$): δ 11.45-11.33 (m, 3H), 8.53-8.45 (m, 3H), 8.35 (t, J=4.9 Hz, 2H), 7.33-7.25 (m, 5H), 5.04 (s, 2H), 3.59-3.19 (m, 16H), 3.15-3.12 (q, J=6.0 Hz, 2H), 3.06-3.04 (t, J=6.9 Hz, 1H), 1.77-1.71 (m, 1H), 1.55-1.32 (m, 59H). HRMS (ESI) calcd for C$_{57}$H$_{97}$N$_{14}$O$_{17}$ [M+H]$^+$ m/z 1249.7156; found: 1249.7166.

Compound 7

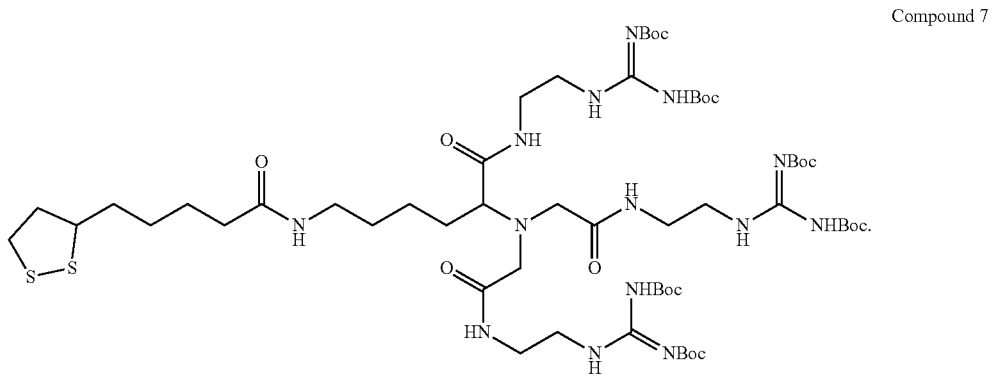

A solution of 6 (0.12 mmol) in MeOH (2 mL) was added palladium on charcoal (Pd/C, 10% Pd content, 13 mg). The mixture was stirred at rt under an atmosphere of hydrogen gas for 6 h. The solution was filtered through a pad of Celite. The residue was concentrated to dryness in vacuo, and the resulting residue was dissolved in DCM (2 mL). Lipoic acid (0.152 mmol), EDCI (0.304 mmol), HOBt (0.304 mmol), and TEA (0.304 mmol) were added to the mixture and then stirred at rt for 2 h. The mixture was concentrated to dryness in vacuo and then diluted with ethyl acetate. The organic layer was washed with H$_2$O three times, dried over MgSO$_4$, filtered, and concentrated. The crude product was purified by column chromatography on silica gel (MeOH/DCM 1:50) to yield 7 (94 mg, 82%). $^1$H NMR (600 MHz, CDCl$_3$): δ 11.48-11.30 (m, 3H), 8.57-8.46 (m, 3H), 8.40 (t, J=5.2 Hz, 2H), 8.15-8.12 (m, 1H), 6.22-6.18 (m, 1H), 3.60-3.34 (m, 16H), 3.28-3.04 (m, 7H), 2.48-2.38 (m, 1H), 2.17-2.14 (t, J=7.4 Hz, 2H), 1.92-1.71 (m, 11H), 1.71-1.59 (m, 4H), 1.57-1.34 (m, 64H). HRMS (ESI) calcd for C$_{57}$H$_{103}$N$_{14}$O$_{16}$S$_2$ [M+H]$^+$ m/z 1303.7118; found: 1303.7129.

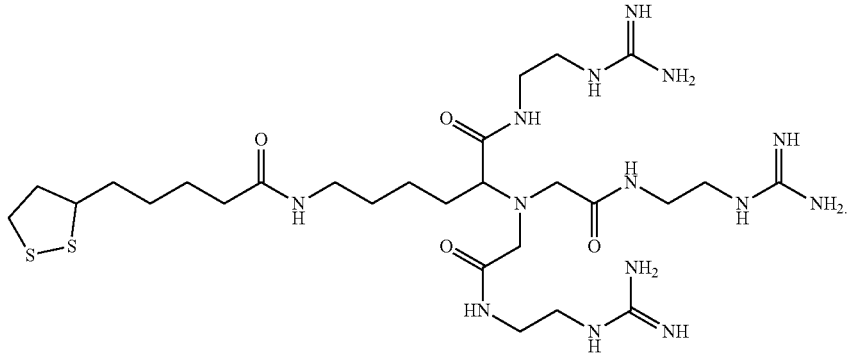

Compound 8

Compound 7 (0.08 mmol) was added to a solution of 4M HCl (0.5 mL) in 1,4-dioxane (0.5 mL), and the mixture was stirred at rt for 12 h. After that, the solution was removed and dried in vacuo to yield 8 (24 mg, 89%). $^1$H NMR (600 MHz, D$_2$O): δ 3.60-3.40 (m, 3H), 3.4-3.16 (m, 16H), 3.02 (s, 2H), 2.76 (s, 2H), 2.20-2.03 (m, 2H), 1.98-1.76 (m, 2H), 1.62-1.16 (m, 11H). $^{13}$C NMR (150 MHz, D$_2$O): δ 176.61, 175.62, 173.68, 172.92, 156.88 (x3), 66.01, 65.73, 56.57, 55.36, 55.24, 40.40 (x2), 40.27, 38.69, 37.99 (x3), 37.82, 35.44, 33.57, 28.66, 28.18, 27.73, 24.99, 22.71. HRMS (ESI) calcd for C$_{27}$H$_{55}$N$_{14}$O$_4$S$_2$ [M+H]$^+$ m/z 703.3967; found: 703.3995.

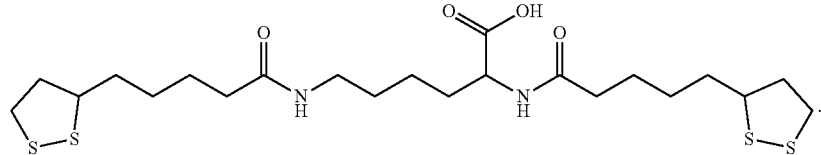

Compound 9

A solution of lipoic acid (2.5 mmol) in DMF (3 mL) was preactivated with EDCI (3 mmol), HOBt (3 mmol), and trimethylamine (3 mmol) under nitrogen for 30 min. Lysine (1 mmol) in DMF (3 mL) was then added to the above solution, and the resulting solution was stirred at rt for 2 h. The mixture was concentrated to dryness in vacuo and then diluted with ethyl acetate. The organic layer was washed with H$_2$O three times, dried over MgSO$_4$, filtered, and concentrated. The crude product was purified by column chromatography on silica gel (MeOH/DCM 1:20) to yield 9 (230 mg, 90%). $^1$H NMR (600 MHz, MeOD): δ 4.37-4.32 (dd, J=4.6, 9.2 Hz, 1H), 3.63-3.57 (qui, J=6.8 Hz, 2H), 3.22-3.17 (m, 4H), 3.14-3.09 (m, 2H), 2.51-2.45 (m, 2H), 2.29 (t, J=7.0 Hz, 2H), 2.21 (t, J=7.0 Hz, 2H), 1.95-1.86 (m, 3H), 1.79-1.62 (m, 9H), 1.60-1.40 (m, 8H). HRMS (ESI) calcd for C$_{57}$H$_{97}$N$_{14}$O$_{17}$ [M+H]$^+$ m/z 1249.7156; found: 1249.7166.

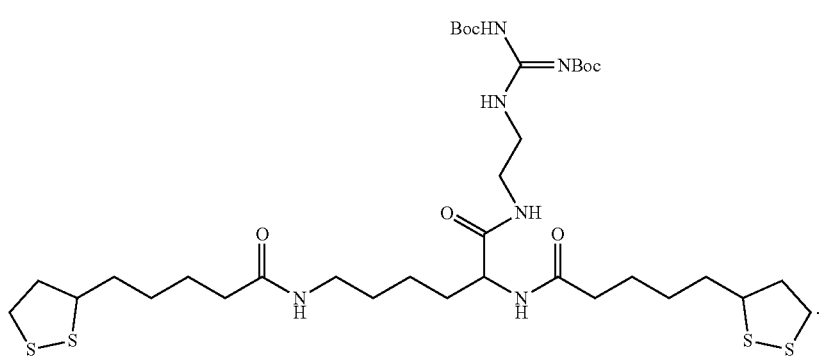

Compound 10

A solution of 9 (0.141 mmol) in DMF (1 mL) was preactivated with EDC (0.211 mmol), HOBt (0.211 mmol), and trimethylamine (0.282 mmol) under nitrogen for 30 min. 5 (0.183 mmol) in DMF (1 mL) was then added to the above solution and the resulting solution was stirred at rt for 2 h. The mixture was concentrated to dryness in vacuo and then diluted with ethyl acetate. The organic layer was washed with H$_2$O three times, dried over MgSO$_4$, filtered, and concentrated. The crude product was purified by column chromatography on silica gel (MeOH/DCM 1:20) to yield 10 (92 mg, 84%). $^1$H NMR (600 MHz, CDCl$_3$): δ 11.39 (s, 1H), 8.58 (t, J=6.0 Hz, 1H), 7.98 (t, J=4.6 Hz, 1H), 6.41 (d, J=7.4 Hz, 1H), 5.79-5.74, (m, 1H), 4.37 (q, J=7.5 Hz, 1H), 3.57-3.48 (m, 4H), 3.44-3.35 (m, 2H), 3.26-3.12 (m, 4H), 3.11-3.05 (m, 2H), 2.46-2.39 (m, 2H), 2.18 (t, J=7.4 Hz, 2H), 2.13 (t, J=7.4 Hz, 2H), 1.91-1.84 (m, 2H), 1.82-1.75 (m, 1H), 1.71-1.57 (m, 9H), 1.54-1.35 (m, 20H), 1.33-1.25 (m, 2H). $^{13}$C NMR (150 MHz, CDCl$_3$): δ 172.91, 172.55, 171.72, 162.87, 157.42, 153.03, 83.72, 79.97, 56.46, 56.44, 52.78, 41.19, 40.27, 40.26, 40.20, 38.96, 38.48 (x2), 36.48, 36.37, 36.30, 34.64, 34.61, 32.60, 29.18, 28.95, 28.88, 28.29 (x2), 28.05 (x2), 25.46, 25.36, 25.32, 22.29. HRMS (ESI) calcd for C$_{35}$H$_{63}$N$_6$O$_7$S$_4$ [M+H]$^+$ m/z 807.3641; found: 807.3655.

Compound 10 (0.1 mmol) was added to a solution of 4 M HCl (0.5 mL) in 1,4-dioxane (0.5 mL), and the mixture was stirred at rt for 12 h. After that, the solution was removed and dried in vacuo to yield 8 (59 mg, quant.). The compound was pure to use directly without further purification.

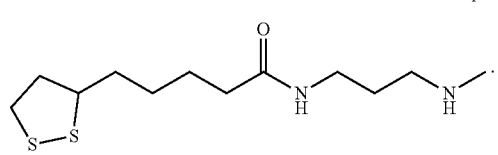

Compound 12

A solution of lipoic acid (3 mmol) and CDI (3.9 mmol) was dissolved in 25 ml of anhydrous DCM. This solution was added dropwise at 0° C. to 5 ml of anhydrous DCM containing 8 mmol of N-methyl-1,3-propanediamine. The reaction mixture was stirred for 40 min at 0° C. and 30 min at room temperature, then it was washed with H$_2$O three times and was dried over MgSO$_4$, filtered, and concentrated to give 12 (589 mg, 66%). $^1$H NMR (600 MHz, CDCl$_3$): δ 3.57-3.50 (m, 1H), 3.31 (q, J=5.8 Hz, 2H), 3.17-3.12 (m, 1H), 3.11-3.05 (m, 1H), 2.65 (t, J=6.0 Hz, 2H), 2.46-2.40 (m, 1H), 2.39 (s, 3H), 2.15-2.11 (m, 2H), 1.91-1.84 (m, 1H), 1.72-1.54 (m, 6H), 1.49-1.37 (m, 2H). HRMS (ESI) calcd for C$_{12}$H$_{26}$N$_2$OS$_2$ [M+H]$^+$ m/z 277.1408; found: 277.1399.

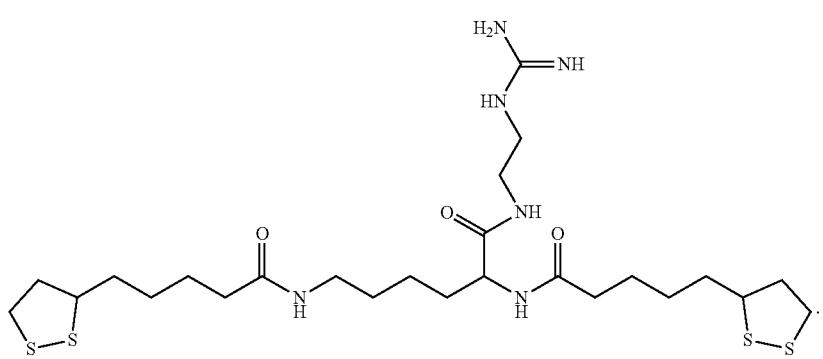

Compound 11

Compound 13

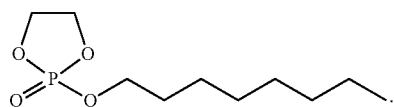

Compound 13 was synthesized and characterized according to a published protocol. $^1$H NMR (600 MHz, CDCl$_3$): δ 4.50-4.38 (m, 4H), 4.19-4.15 (m, 2H), 1.74-1.70 (m, 2H), 1.38-1.20 (m, 12H), 0.89 (t, J=7.2 Hz, 3H). The synthesis was performed according to Liu, S. et al., Zwitterionic Phospholipidation of Cationic Polymers Facilitates Systemic mRNA Delivery to Spleen and Lymph Nodes. *J. Am. Chem. Soc.* 2021, 143, 21321-21330, which is herein incorporated by reference in its entirety.

Compound 14

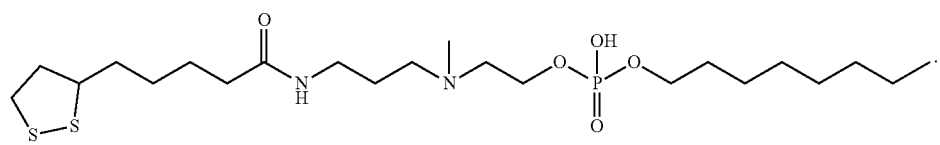

A solution of 12 (0.25 mmol) in 1 ml anhydrous DMF was added to 13 (0.25 mmol), and the reaction was stirred at 70° C. for 24 h. The mixture was concentrated to dryness in vacuo to give 14 (116 mg, 90%). $^1$H NMR (600 MHz, MeOD): δ 7.90 (s, 1H), 4.14-4.01 (m, 1H), 3.91-3.83 (m, 1H), 3.73-3.67 (m, 1H), 3.62-3.55 (m, 1H), 3.28 (t, J=6.6 Hz, 2H), 3.21-3.15 (m, 1H), 3.13-3.06 (m, 1H), 2.98 (t, J=7.2 Hz, 2H), 2.69 (s, 3H), 2.50-2.41 (m, 1H), 2.24 (t, J=7.2 Hz, 2H), 1.93-1.84 (m, 1H), 1.76-1.59 (m, 6H), 1.51-1.43 (m, 2H), 1.43-1.37 (m, 1H), 1.36-1.25 (m, 5H), 0.92-0.88 (m, 3H). $^{13}$C NMR (150 MHz, MeOD): δ 177.08, 79.68, 57.79, 48.91, 48.77, 48.04, 41.54, 39.55, 37.06, 36.91, 35.91, 33.85, 33.20, 32.09, 32.05, 30.44, 30.12, 27.73, 27.16, 26.81, 23.92, 14.65. HRMS (ESI) calcd for C$_{22}$H$_{44}$N$_2$O$_5$PS$_2$ [M−H]$^-$ m/z 511.2429; found: 511.2423.

Preparation of the Exemplary Initiators of the Present Disclosure

Nine exemplary initiators, Initiators I2, I3, I4, I5, I6, I7, I8, I9, and I10, were described herein. Initiators I2 (Compound 34), I3 (Compound 39), and I4 (Compound 37) were prepared according to Scheme 4, Scheme 5, and Scheme 6. Initiators, I5 (Compound 16), I6 (Compound 43), I7 (Compound 44), I8 (Compound 40), I9 (Compound 49), and I10 (Compound 54) were prepared according to Scheme 7, Scheme 8, Scheme 9, and Scheme 10. The compounds obtained in each step of the schemes were verified by NMR. Additional details and data are described below.

Additionally, a control Initiator I1 was prepared in this example. I1, bearing no glycan head, is an initiator without particular targeting preference and was prepared to form a copolymer of exemplary propagators of the present disclosure to characterize the propagators. The Initiator I1 has the structure below:

I1

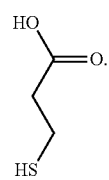

Scheme 4

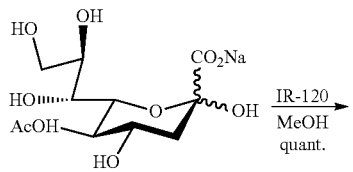

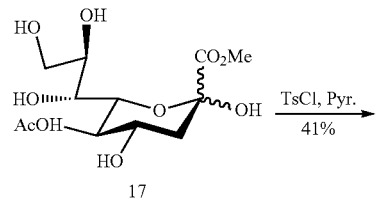

17

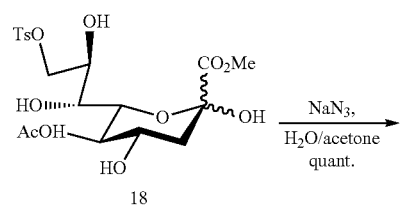

18

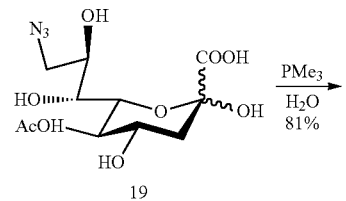

19

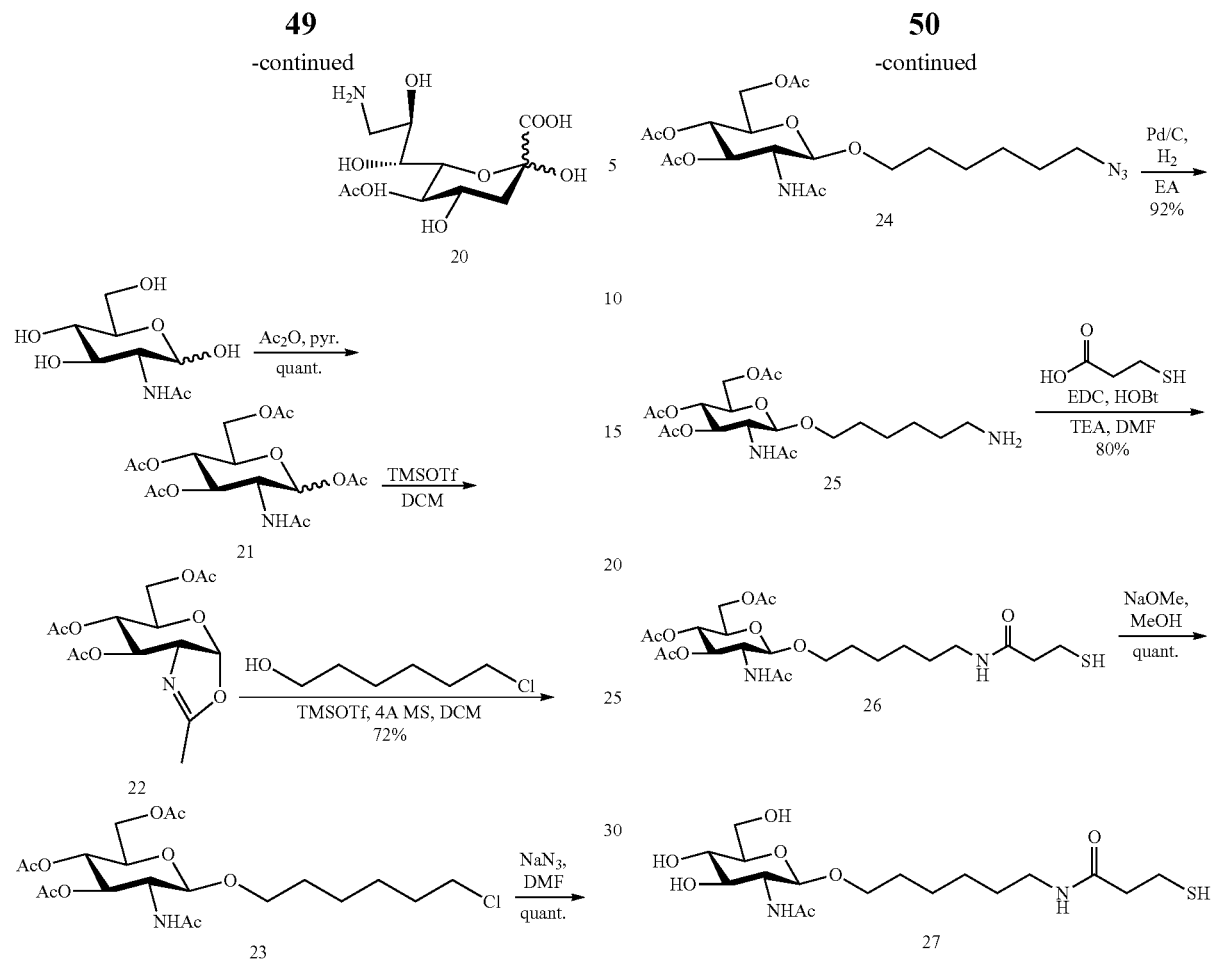

Scheme 5
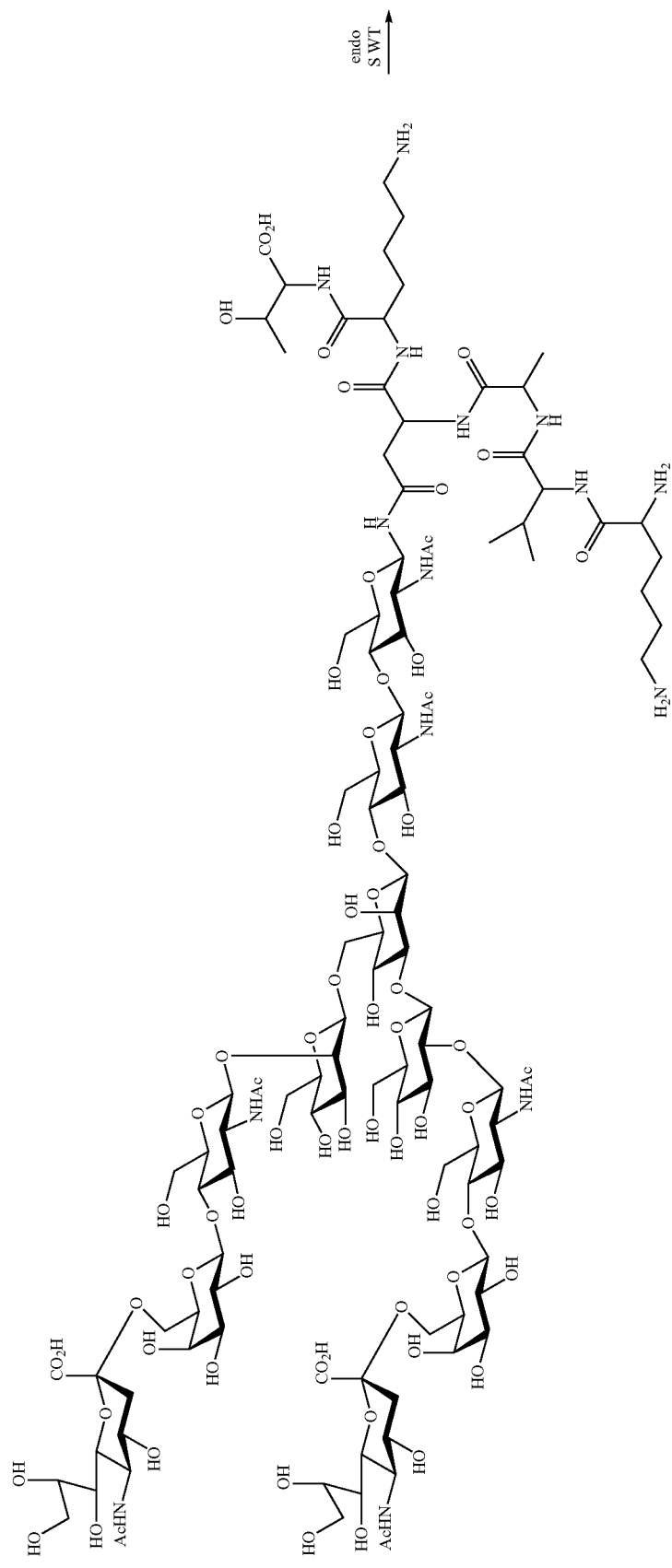

-continued
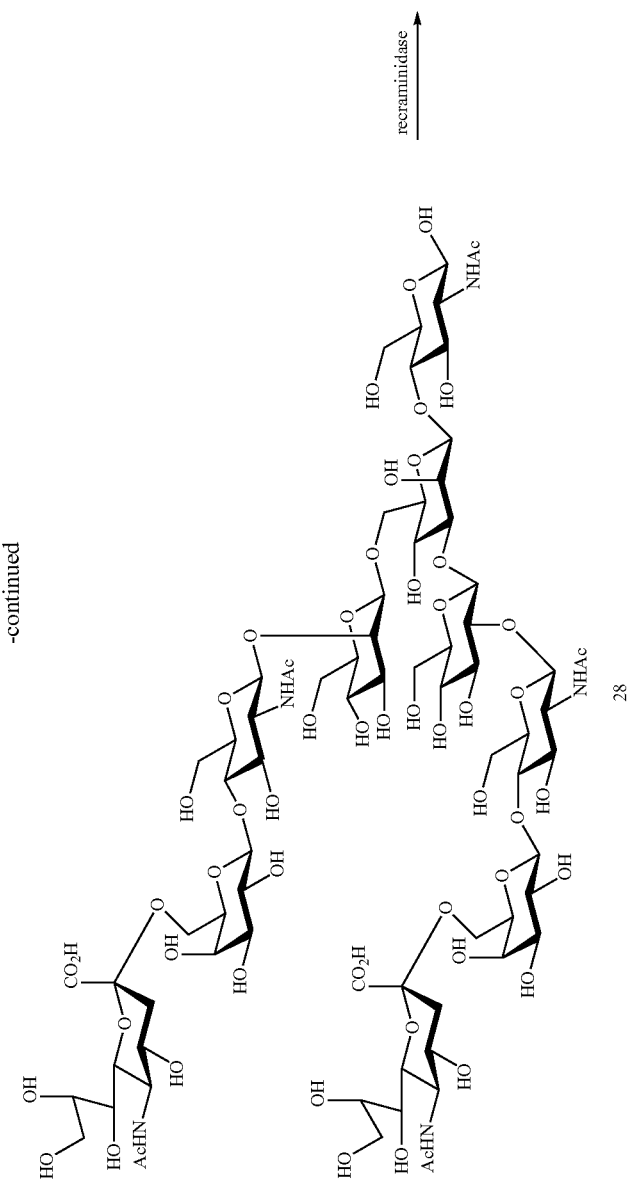
28
→ recraminidase

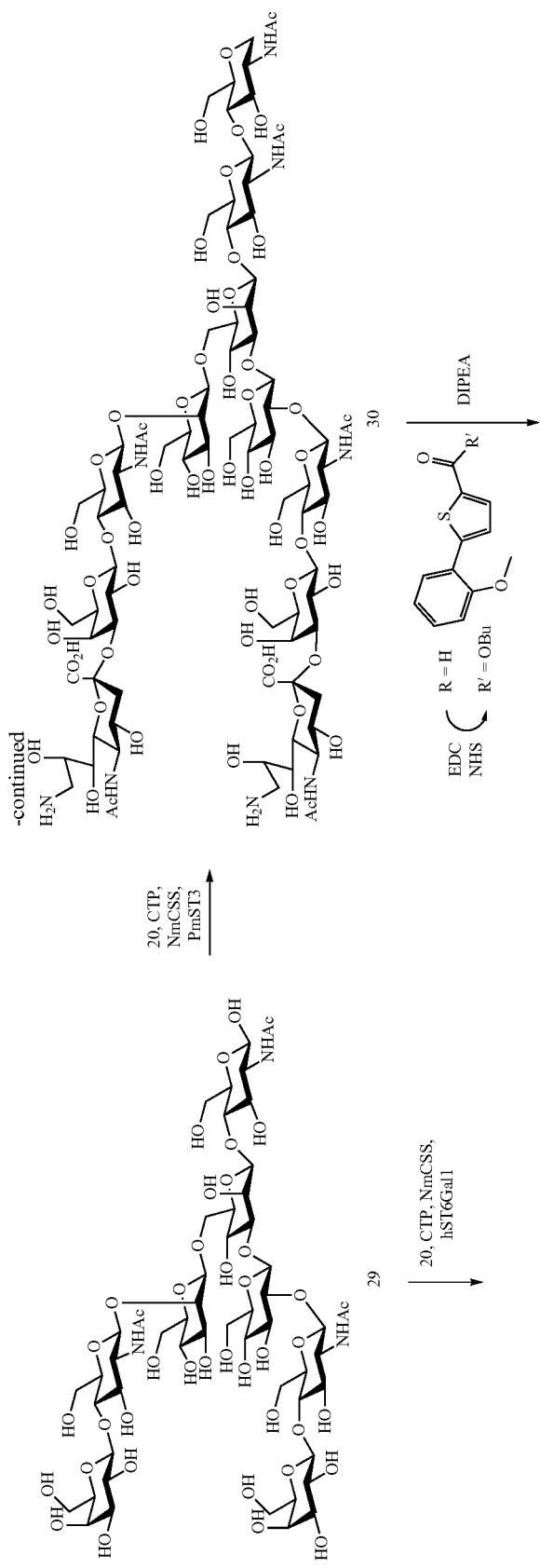

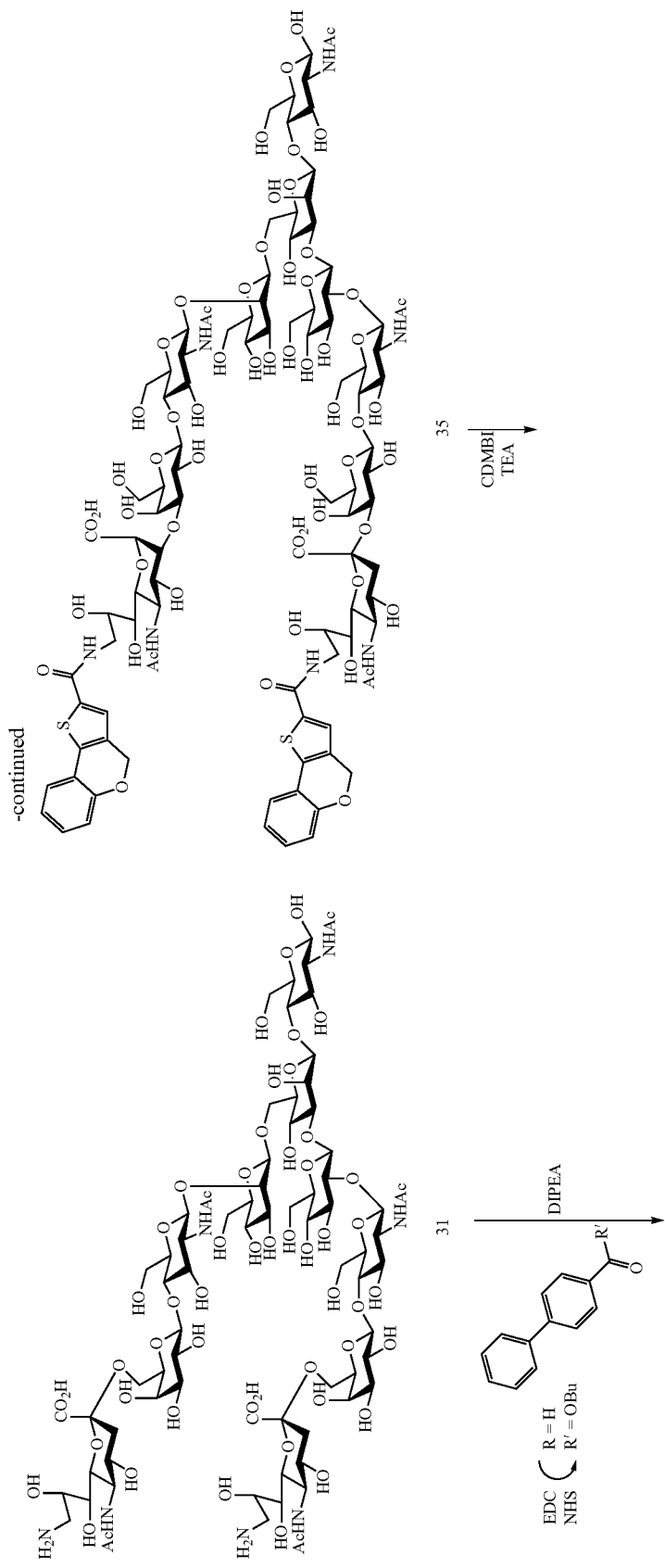

-continued
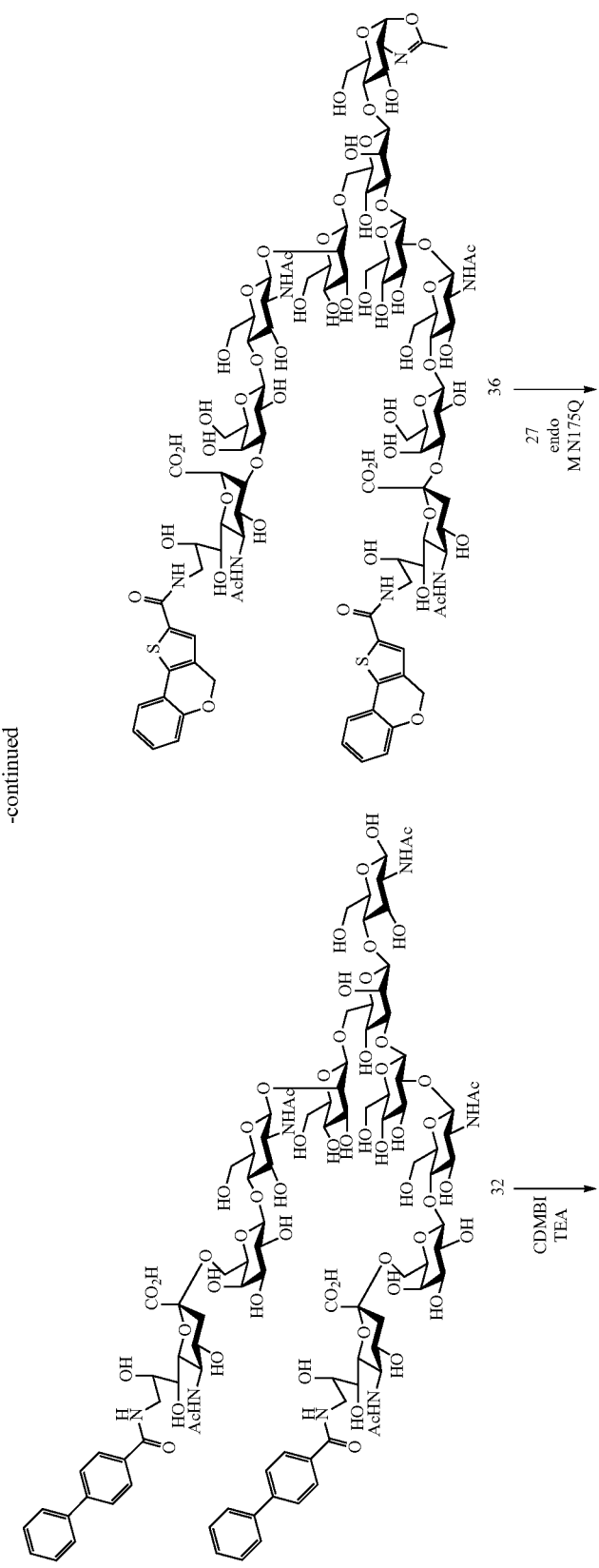

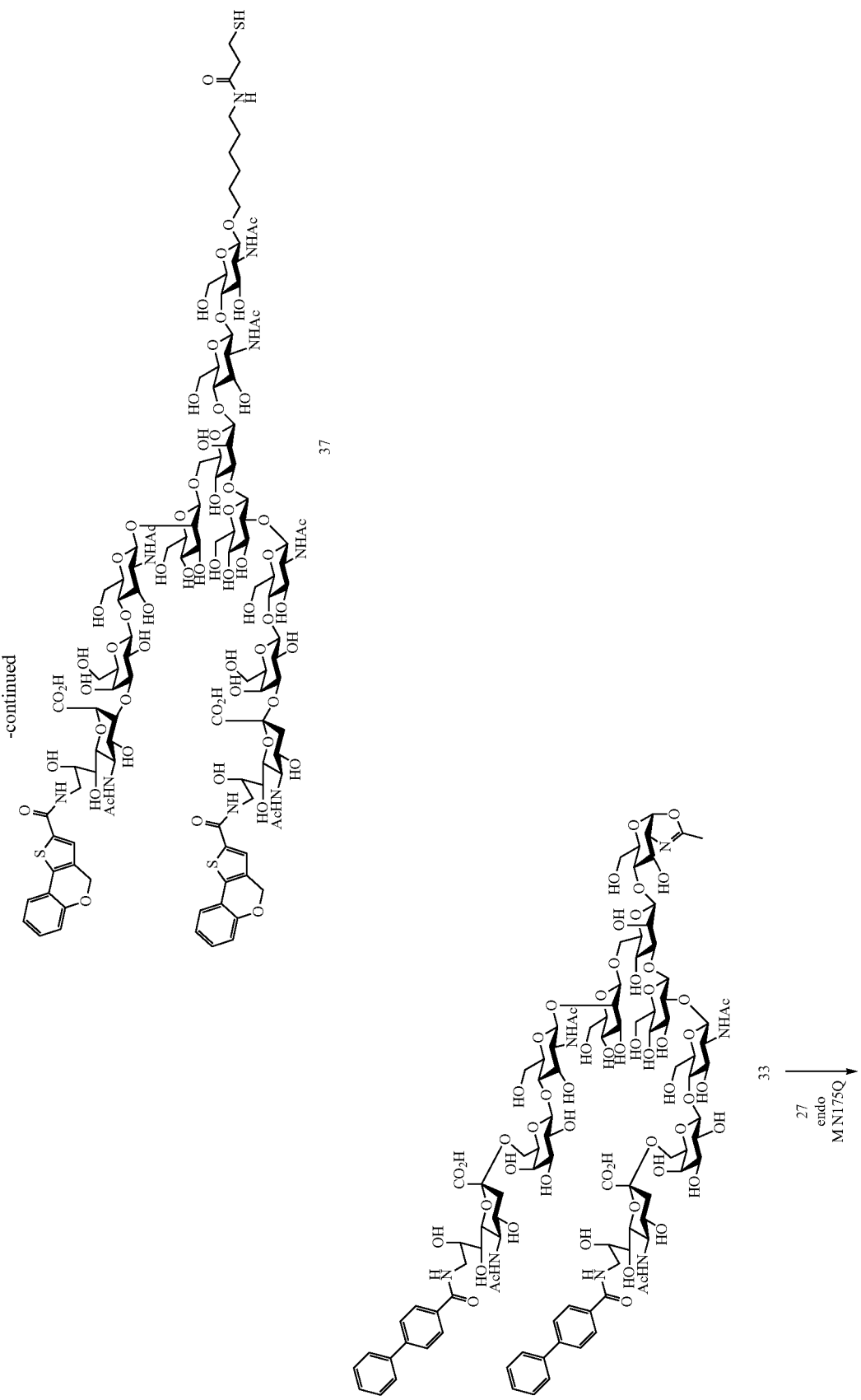

-continued
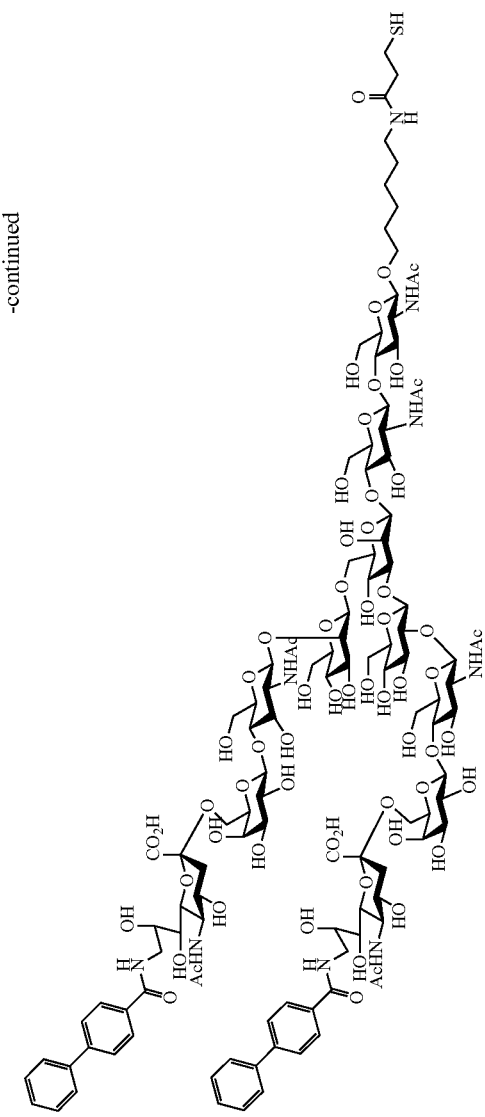
34

Scheme 6
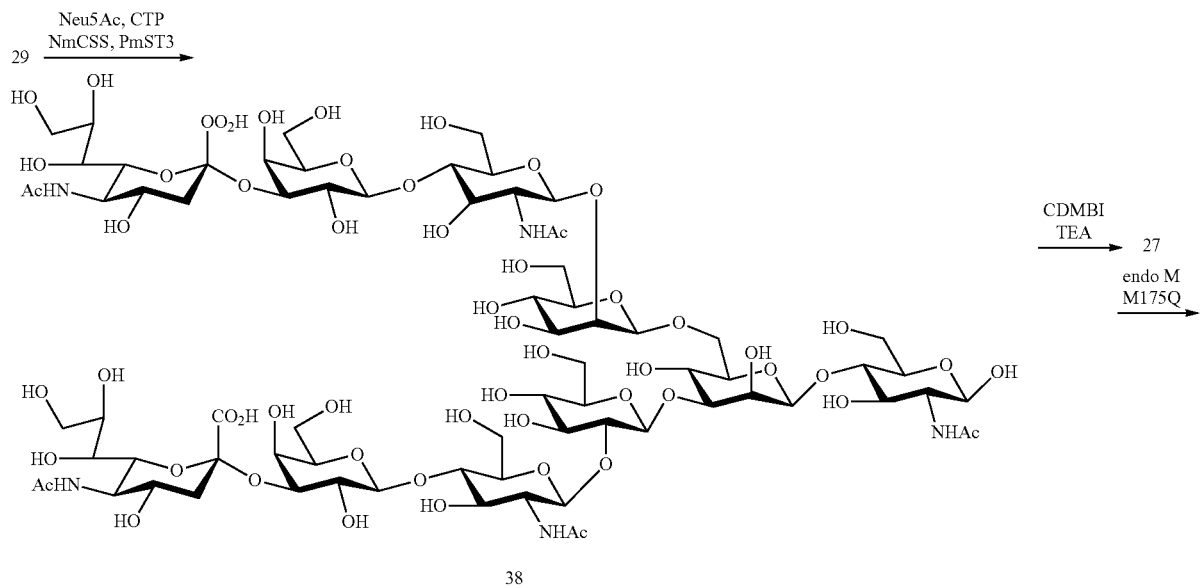
Scheme 7
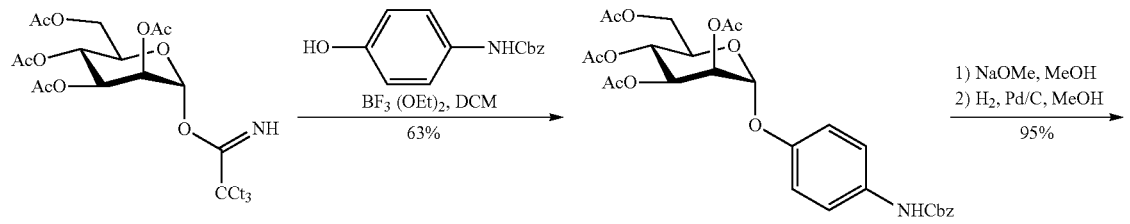

US 12,318,485 B2
67    68
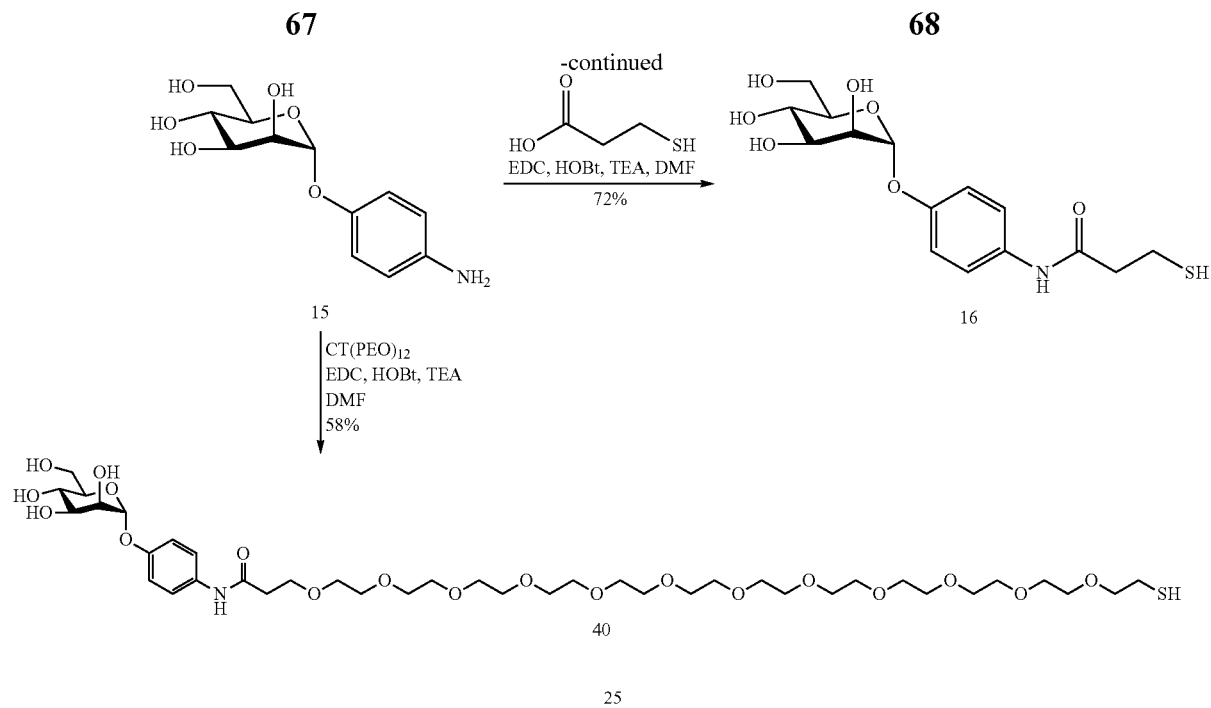
Scheme 8
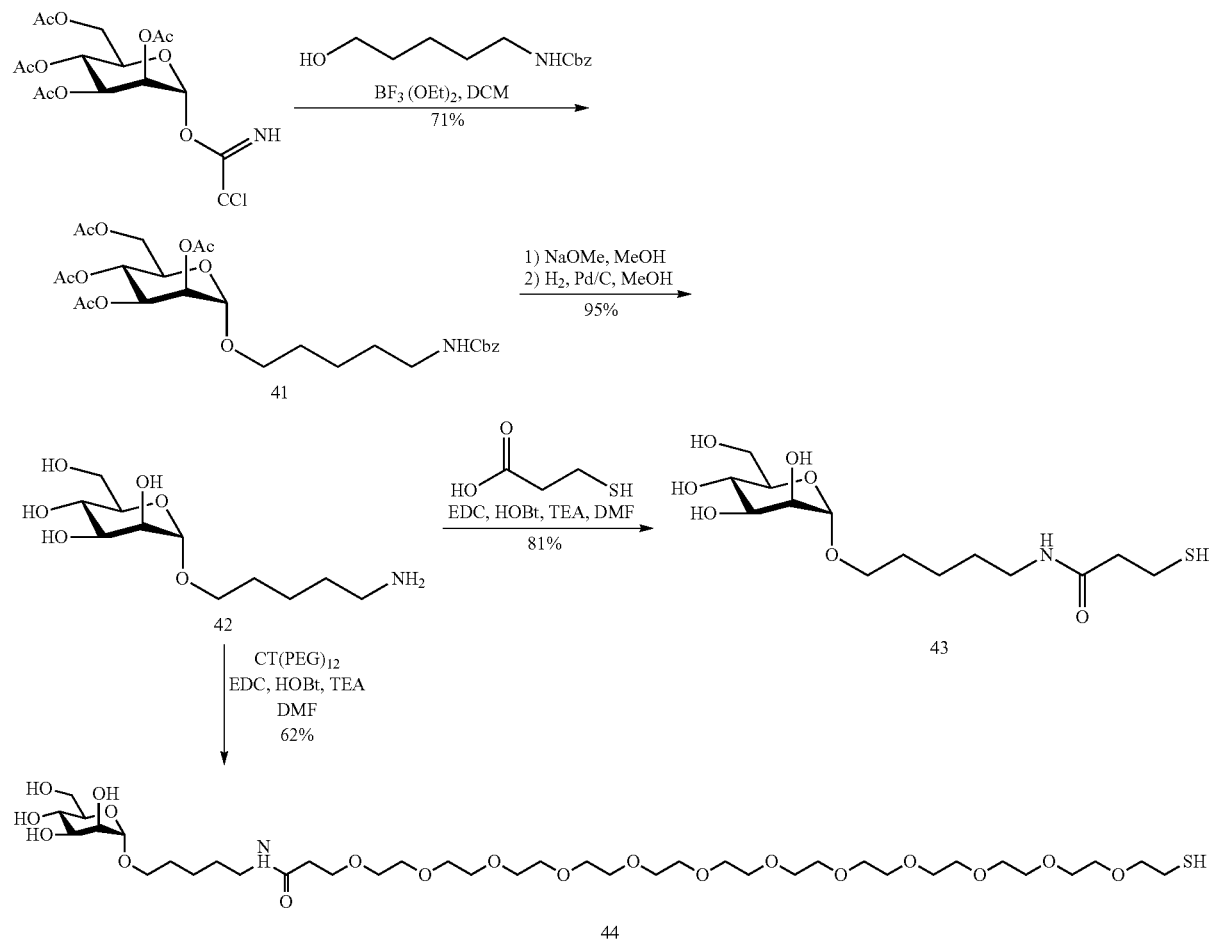

Scheme 9
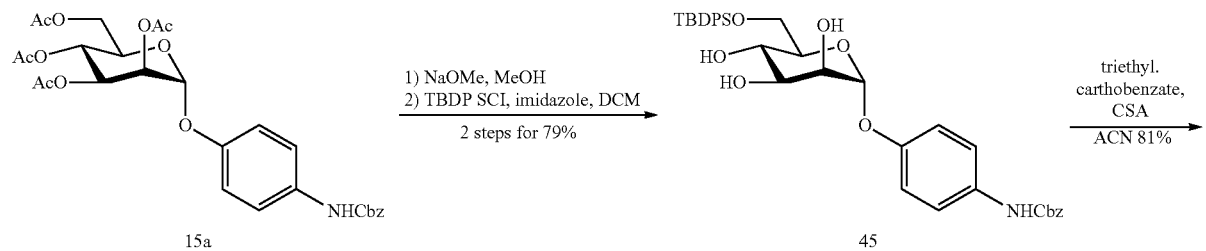
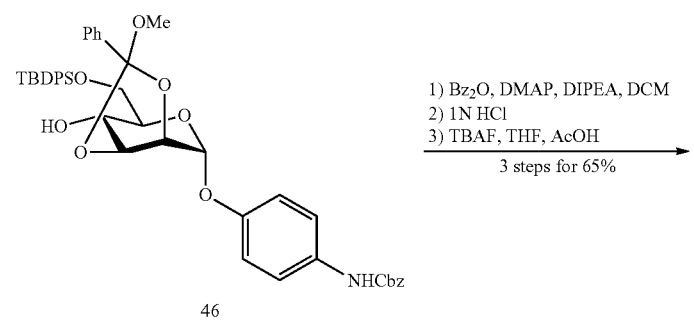
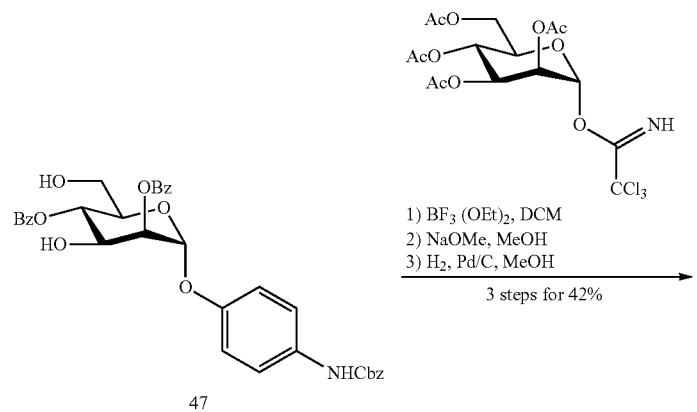
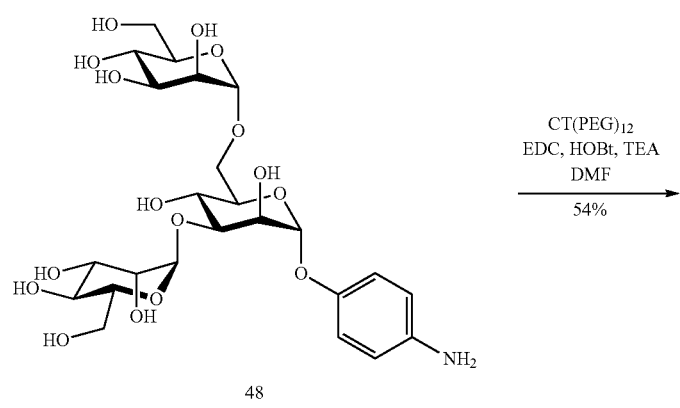

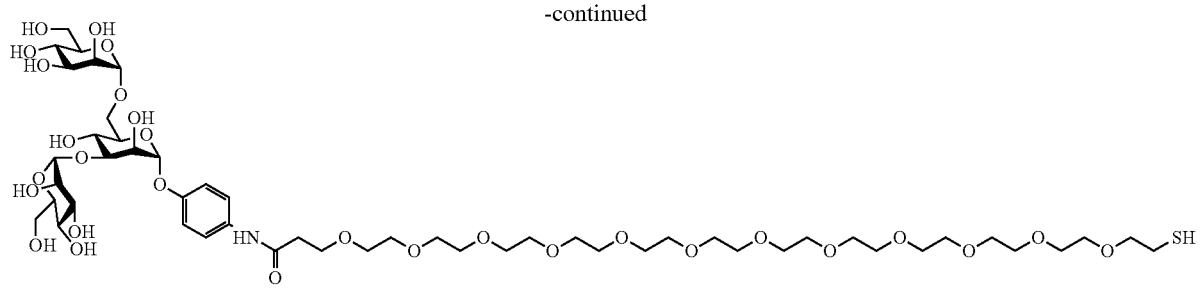
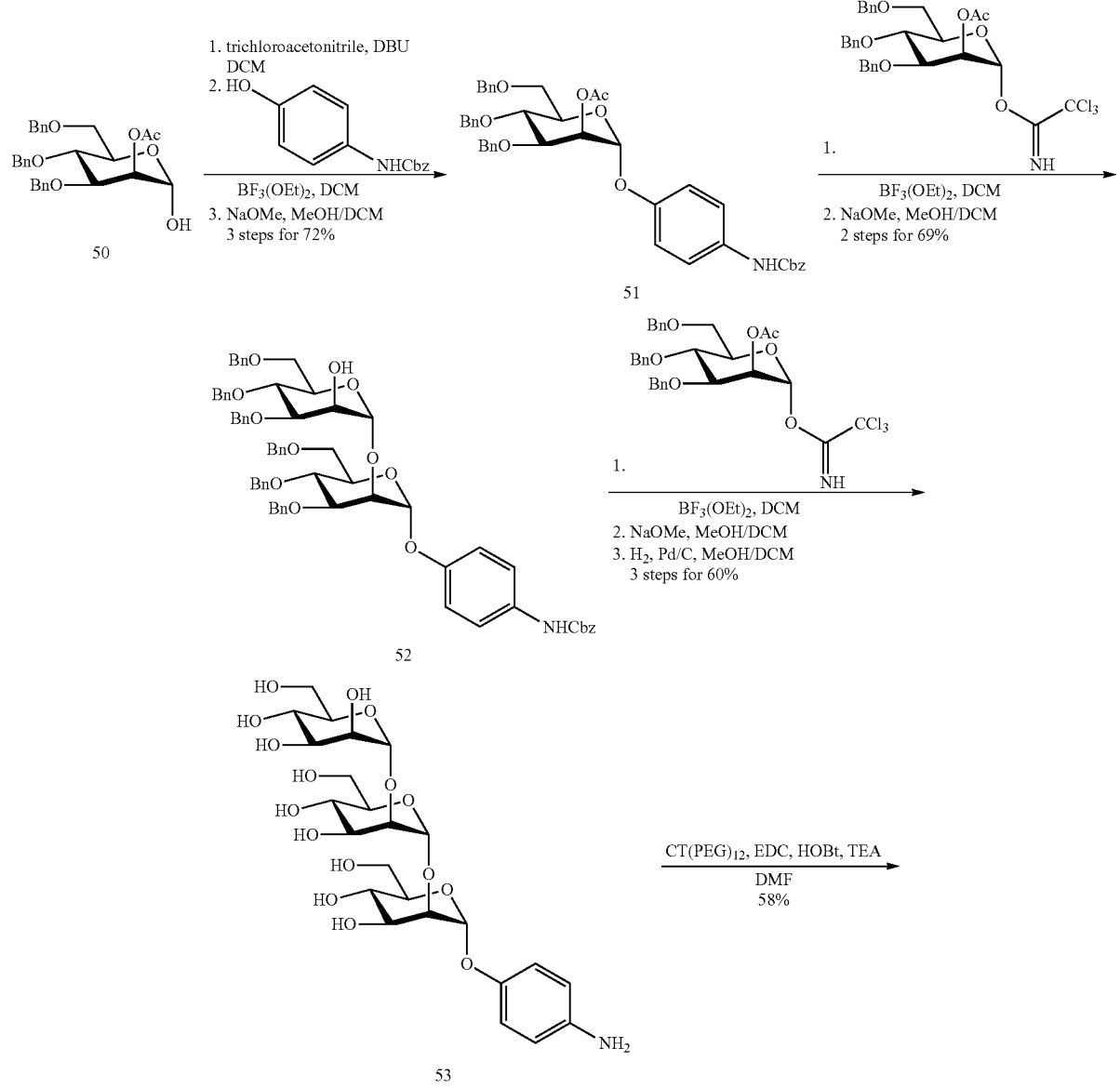
Scheme 10

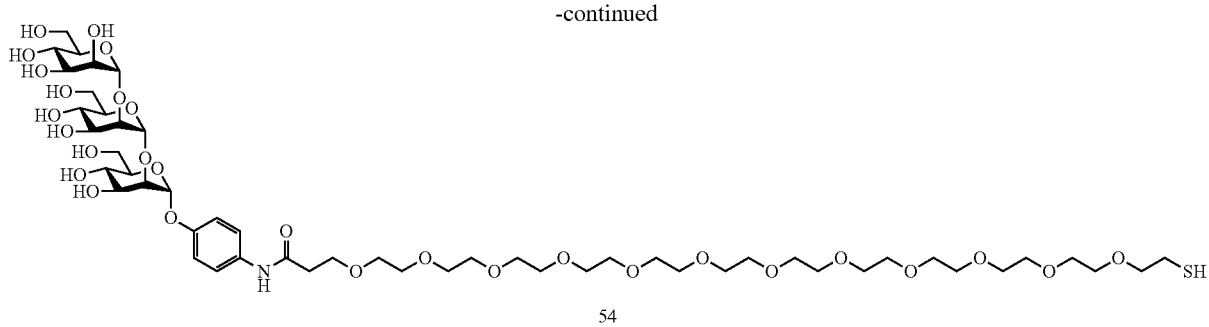

54

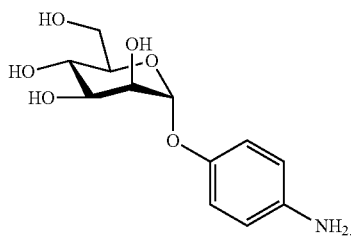

Compound 15[8]

Compound 15 was synthesized and characterized according to a published protocol. 1H NMR (600 MHz, MeOD): δ 6.93 (d, J=8.6 Hz, 2H), 6.71 (d, J=8.6 Hz, 2H), 5.3 (s, 1H), 4.00-3.99 (m, 1H), 3.89-3.88 (m, 1H), 3.81-3.79 (m, 1H), 3.79-3.70 (m, 2H), 3.69-3.67 (m, 1H).

Compound 16

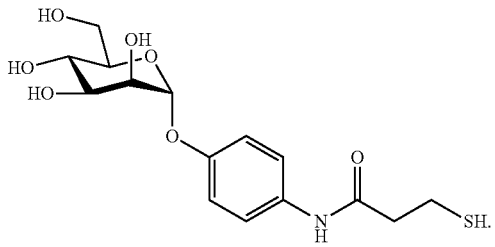

A solution of 15 (0.24 mmol) in DMF (2 mL) was added EDC (0.24 mmol), HOBt (0.24 mmol), trimethylamine (0.4 mmol), and 3-mercaptopropionic acid (0.2 mmol), and the resulting solution was stirred under nitrogen at rt for 2 h. The mixture was concentrated to dryness in vacuo, and the crude product was purified by column chromatography on silica gel (MeOH/DCM 1:2) to yield 16 (72%). $^1$H NMR (600 MHz, MeOD) δ 6.94 (d, J=8.6 Hz, 2H), 6.72 (d, J=8.6 Hz, 2H), 5.30 (s, 1H), 4.00 (dd, J=3.4, 1.8 Hz, 1H), 3.89 (dd, J=9.7, 3.4 Hz, 1H), 3.81-3.67 (m, 4H), 2.72 (t, J=6.8 Hz, 2H), 2.60 (t, J=6.8 Hz, 2H). $^{13}$C NMR (150 MHz, MeOD) δ 176.55, 151.13, 143.23, 119.25 (x2), 117.93 (x2), 101.49, 101.32, 75.10, 72.43, 72.18, 68.42, 62.66, 40.34, 20.70. HRMS (ESI) calcd for $C_{15}H_{22}NO_7S$ [M+H]$^+$: 360.1117, found 360.1101.

Compound 17-20

Compounds 17-20 were synthesized according to Peng, W.; Paulson, J. C., CD22 Ligands on a Natural N-Glycan Scaffold Efficiently Deliver Toxins to B-Lymphoma Cells. *J. Am. Chem. Soc.* 2017, 139, 12450-12458, which is herein incorporated by reference in its entirety.

Compound 21-25

Compounds 21-25 were synthesized according to Chien, W.-T., et al., Sequential one-pot enzymatic synthesis of oligo-N-acetyllactosamine and its multi-sialylated extensions. *Chem. Commun.* 2014, 50, 5786-5789.

Compound 26.

Compound 25 (0.43 mmol) in DCM (5 mL) was added EDC (0.52 mmol), HOBt (0.52 mmol), trimethylamine (0.86 mmol), and 3-mercaptopropionic acid (0.47 mmol), and the resulting solution was stirred under nitrogen at rt for 2 h. The mixture was concentrated to dryness in vacuo, and the crude product was purified by column chromatography on silica gel (MeOH/DCM 1:10) to yield 26 (184 mg, 80%). $^1$H NMR (600 MHz, CDCl$_3$) δ 5.96 (d, J=8.6 Hz, 1H), 5.28 (t, J=9.6 Hz, 1H), 5.05 (t, J=9.4 Hz, 1H), 4.64 (d, J=8.4 Hz, 1H), 4.24 (dd, J=12.3, 4.7 Hz, 1H), 4.11 (dd, J=12.3, 2.5 Hz, 1H), 3.86-3.80 (m, 2H), 3.68-3.66 (m, 1H), 3.47-3.43 (m, 1H), 3.34-3.29 (m, 1H), 3.22-3.16 (m, 1H), 2.81 (t, J=8.2 Hz, 2H), 2.51-2.45 (m, 2H), 2.06 (s, 3H), 2.01 (s, 3H), 2.00 (s, 3H), 1.93 (s, 3H), 1.57-1.51 (m, 4H), 1.48 (t, J=7.0 Hz, 2H) 1.37-1.29 (m, 4H). HRMS (ESI) calcd for $C_{23}H_{38}N_2O_{10}S$ [M+H]$^+$: 535.2325, found 535.2314. The synthesis was performed according to Maklakova, S. Y. et al., Cellular uptake of N-acetyl-d-galactosamine-, N-acetyl-d-glucosamine- and d-mannose-containing fluorescent glycoconjugates investigated by liver intravital microscopy. *Carbohydr. Res.* 2020, 489, 107928, which is herein incorporated by reference in its entirety.

Compound 27.

Compound 26 in MeOH was added NaOMe and the resulting solution was stirred under nitrogen at rt for 2 h. The mixture was neutralized by IR-120, and then filtered, concentrated to dryness in vacuo to yield 27 (92 mg, quant.)$^1$H NMR (600 MHz, MeOD) δ 4.38 (d, J=9.2 Hz, 1H), 3.90-3.86 (m, 2H), 3.68 (dd, J=12.9, 5.9 Hz, 1H), 3.65-3.62 (m, 1H), 3.48-3.43 (m, 2H), 3.28-3.24 (m, 1H), 3.20-3.14 (m, 2H), 2.94 (t, J=7.3 Hz, 1H), 2.73 (t, J=7.3 Hz, 1H), 2.59 (t, J=7.3 Hz, 1H), 2.47 (t, J=7.3 Hz, 1H), 1.97 (s, 3H), 1.56-1.48 (m, 4H), 1.39-1.35 (m, 4H). $^{13}$C NMR (150 MHz, MeOD): δ 173.70, 169.75, 102.74, 77.92, 76.07, 70.50, 62.76, 57.35, 41.02, 40.32, 36.45, 35.19, 30.49, 27.66, 26.73, 23.03. HRMS (ESI) calcd for $C_{17}H_{32}N_2O_{17}S$ [M+H]$^+$: 409.2008, found 409.2017.

Preparation of 9$^{4m}$Neu5Ac-α2,3-SCT 30, 9$^{4m}$Neu5Ac-α2,6-SCT 31, and Neu5Ac-α2,3-SCT 38

30 mg sialylglycopeptide (SGP) was digested by Endo-S WT (300 g) in Tris-HCl buffer at 37° C. for 48 h, and purified by Sephadex G-25 gel filtration chromatography, and the product was analyzed by ESI-MS to give SCT compound 28, according to Lin, C.-W., et al., Homogeneous antibody and CAR-T cells with improved effector functions targeting SSEA-4 glycan on pancreatic cancer. *Proceedings of the National Academy of Sciences* 2021, 118, e2114774118, which is herein incorporated by reference in its entirety. Neuraminidase (5 U/ml, 12 μL) in Tris-HCl buffer was added to the mixture at 37° C. for 12 h and purified by Sephadex G-25 gel filtration chromatography to give desialylated N-glycan 29. After that, the reaction was carried out in 0.5 mL of HEPES buffer (50 mM, pH 8.5) containing 100 mM of 9'Neu5Ac (14.5 mg, 47 μmol), 110 mM of CTP (27.2 mg, 52 μmol), and 20 mM of MgCl$_2$. The pH of the reaction mixture was adjusted to 8.5 by adding 2N NaOH. Then, 0.5 mg/mL of NmCSS was added to the above solution. The resulting mixture was incubated at 37° C. for 8 h, and the formation of CMP-9$^{4m}$Neu5Ac was monitored by TLC analysis.

For 9$^{4m}$Neu5Ac-α2,6-SCT, hST6Gal-I (0.5 mg/mL) was added to the 9$^{4m}$Neu5Ac reaction mixture with N-glycan and incubated at 37° C., according to Peng, W., et al., Recent H3N2 Viruses Have Evolved Specificity for Extended, Branched Human-type Receptors, Conferring Potential for Increased Avidity. *Cell Host Microbe* 2017, 21, 23-34, which is herein incorporated by reference in its entirety. For 9$^{4m}$Neu5Ac-α2,3-SCT, PmST3 (0.3 mg/mL) was added to the 9$^{4m}$Neu5Ac reaction mixture with N-glycan and incubated at 37° C. For Neu5Ac-α2,3-SCT, PmST3 (0.3 mg/mL) was added to the Neu5Ac reaction mixture with N-glycan and incubated at 37° C. The reactions above were monitored by mass spectrometry analysis and TLC. After the acceptor was consumed, the reaction was centrifuged, and the supernatant was subjected to a centrifuge filter with a molecular mass cutoff of 10 kDa (Amicon Ultra, Millipore) to remove proteins. The filtrate was purified with P-2 gel filtration chromatography to give 9$^{4m}$Neu5Ac-α2,3-SCT 30, 9$^{4m}$Neu5Ac-α2,6-SCT 31, and Neu5Ac-α2,3-SCT 38.

Preparation of 9$^{BPC}$Neu5Ac-α2,6-SCT-SH 34, 9$^{TCC}$Neu5Ac-α2,3-SCT-SH 37 and Neu5Ac-α2,3-SCT-SH 39

9$^{4m}$Neu5Ac-α2,6-SCT and DIEA (5.0 eq) were dissolved in H$_2$O, followed by the addition of biphenyl carboxylic acid-N-hydroxysuccinimide ester (BPC-NHS) (3 eq) in THF. The reaction was stirred at 0° C. until the starting material was consumed. Then, the reaction was purified by Sep-Pak C18 column (2 g, Waters Corp.) and eluted with H$_2$O-MeOH to give compound 32 in 91% yield. 9$^{4m}$Neu5Ac-α2,3-SCT was prepared similarly as described above by stirring with 4H-thieno[3,2-c]chromene-2-carbamoyl-NHS (TCC-NHS) in THF and H$_2$O to give compound 35. After purification, the product was afforded a 91% yield.

The mixture of 9$^{BPC}$Neu5Ac-α2,6-SCT 32 or 9$^{TCC}$Neu5Ac-α2,3-SCT 35 in water were added CDMBI and TEA and incubated at 4° C. for 1 hour to generate corresponding oxazoline N-glycan 33 and 36, respectively. After that, they were purified by Sephadex G-25 gel filtration chromatography and characterized by ESI-MS. GlcNAc-SH 27 (0.25 mg) and Endo-M (N175Q) (1.6 U/mL) were added to a solution of 50 mM phosphate buffer (pH 7) with 9$^{BPC}$Neu5Ac-α2,6-SCT-oxazoline and incubated at 30° C. for 30 min. The transglycosylation products were isolated by P-2 gel filtration chromatography to give compound 34 and characterized by ESI-MS. 9$^{TCC}$Neu5Ac-α2,3-SCT-SH 37 and Neu5Ac-α2,3-SCT-SH 39 were prepared the same as described above.

Compound 34. 9$^{BPC}$Neu5Ac-α 2,6-SCT-SH $^1$H NMR (600 MHz, DMSO-d$_6$): δ=8.33 (s, 3H, NH), 8.00 (d, J=8.6 Hz, 4H), 7.72 (dd, J=8.0, 14.2 Hz, 9H), 7.49 (t, J=8.3 Hz, 4H), 7.40 (t, J=8.3 Hz, 2H), 4.98-4.95 (m, 2H), 4.76 (s, 1H), 4.54 (s, 1H), 4.44-4.39 (m, 2H), 4.25-4.22 (m, 3H), 3.99 (s, 1H), 3.87 (s, 1H), 3.83-3.73 (m, 5H), 3.41-3.25 (m, 58H), 3.21-3.16 (m, 3H), 3.11-2.99 (m, 4H), 2.87 (t, J=6.9 Hz, 2H), 2.61 (d, J=8.4 Hz, 2H), 2.44 (t, J=7.4 Hz, 2H), 1.91-1.77 (m, 18H), 1.44 (t, J=6.9 Hz, 2H), 1.39-1.28 (m, 4H), 1.28-1.19 (m, 4H), 1.12 (t, J=6.9 Hz, 1H). HRMS (ESI) calcd for C$_{19}$H$_{171}$N$_9$O$_{63}$S$^{2-}$ [M−2H]$^{2-}$: 1383.0093, found 1383.0077.

Compound 37. 9$^{TCC}$Neu5Ac-α2,3-SCT-SH.

$^1$H NMR (600 MHz, DMSO-d$_6$): δ=8.22 (s, 3H, NH), 8.10-8.09 (m, 1H, NH), 7.96-7.93 (m, 1H, NH), 7.81-7.79 (m, 1H, NH), 7.74-7.72 (m, 1H, NH), 7.35 (d, J=7.8 Hz, 2H), 7.29 (s, 2H), 7.20 (t, J=7.8 Hz, 2H), 6.97 (t, J=7.8 Hz, 2H), 6.92 (d, J=7.9 Hz, 2H), 5.29 (s, 4H), 5.01-4.95 (m, 2H), 4.77 (s, 1H), 4.54 (s, 1H), 4.44-4.36 (m, 2H), 4.27-4.19 (m, 3H), 3.99 (s, 1H), 3.88 (s, 1H), 3.85-3.71 (m, 3H), 3.50-3.22 (m, 52H), 3.19 (d, J=9.5 Hz, 2H), 3.10-3.00 (m, 4H), 2.87 (t, J=6.9 Hz, 2H), 2.64-2.58 (m, 2H), 2.44 (t, J=7.4 Hz, 2H), 1.93-1.78 (m, 18H), 1.45-1.39 (m, 2H), 1.39-1.29 (m, 4H), 1.28-1.20 (m, 4H), 1.16 (t, J=6.9 Hz, 1H). HRMS (ESI) calcd for C$_{117}$H$_{169}$N$_9$O$_{65}$S$_3^{2-}$ [M−2H]$^{2-}$: 1416.9606, found 1416.9623.

Compound 39. Neu5Ac-α2,3-SCT-SH $^1$H NMR (600 MHz, DMSO-d$_6$): δ=8.33 (s, 3H, NH), 8.10 (s, 1H, NH), 7.96-7.94 (m, 1H, NH), 7.81-7.80 (m, 1H, NH), 7.74-7.73 (m, 1H, NH), 4.98-4.95 (m, 2H), 4.76-4.75 (m, 1H), 4.54 (s, 1H), 4.46-4.38 (m, 2H), 4.25-4.22 (m, 3H), 3.99 (s, 1H), 3.87 (s, 1H), 3.80-3.71 (m, 4H), 3.41-3.25 (m, 59H), 3.23-3.18 (m, 3H), 3.08-3.01 (m, 3H), 2.87 (t, J=6.9 Hz, 2H), 2.63-2.60 (m, 2H), 2.44 (t, J=7.4 Hz, 2H), 1.87-1.79 (m, 18H), 1.44 (t, J=6.9 Hz, 2H), 1.39-1.28 (m, 4H), 1.28-1.19 (m, 4H), 1.07 (t, J=6.9 Hz, 1H). HRMS (ESI) calcd for C$_{93}$H$_{153}$N$_7$O$_{63}$S$^{2-}$ [M−2H]$^{2-}$: 1203.9357, found 1203.9377.

Compound 40

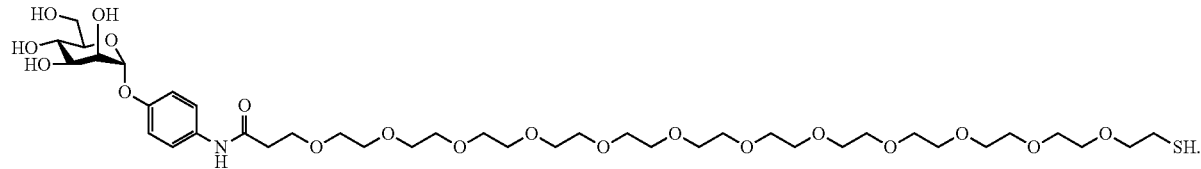

Compound 15 (0.12 mmol) in DMF (1 mL) was added EDC (0.12 mmol), HOBt (0.12 mmol), DMAP (0.12 mmol), trimethylamine (0.2 mmol), and CT(PEG)$_{12}$ (0.1 mmol), and the resulting solution was stirred under nitrogen at rt for 12 h. The mixture was concentrated to dryness in vacuo, and the crude product was purified by column chromatography on silica gel to yield 40 (59%). 1H NMR (600 MHz, MeOD): δ 6.93 (d, J=8.6 Hz, 2H), 6.71 (d, J=8.6 Hz, 2H), 5.3 (s, 1H), 4.00-3.99 (m, 1H), 3.89-3.88 (m, 1H), 3.81-3.70 (m, 5H), 3.70-3.59 (m, 48H), 2.68 (t, J=6.8 Hz, 2H), 2.50-2.47 (m, 2H). $^{13}$C NMR (150 MHz, MeOD): δ 170.17, 151.03, 143.50, 119.26 (x2), 117.82 (x2), 101.36, 75.10, 74.08, 72.45, 72.19, 71.45, 71.41, 71.37, 71.30, 71.24, 71.11, 70.93 (x18), 68.43, 62.68, 24.67. HRMS (ESI) calcd for $C_{39}H_{70}NO_{19}S$ $[M+H]^+$: 888.4263, found 888.4241.

Compound 41-42.

Compounds 41 and 42 were synthesized according to Lee, H.-K. et al., Reactivity-Based One-Pot Synthesis of Oligomannoses: Defining Antigens Recognized by 2G12, a Broadly Neutralizing Anti-HIV-1 *Antibody. Angew. Chem. Int. Ed.* 2004, 43, 1000-1003, which is herein incorporated by reference in its entirety.

Compound 43

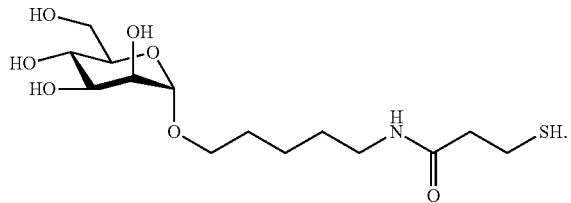

A solution of 42 (0.24 mmol) in DMF (2 mL) was added EDC (0.24 mmol), HOBt (0.24 mmol), trimethylamine (0.4 mmol), and 3-mercaptopropionic acid (0.2 mmol), and the resulting solution was stirred under nitrogen at rt for 2 h. The mixture was concentrated to dryness in vacuo, and the crude product was purified by column chromatography on silica gel (MeOH/DCM 1:3) to yield 16 (81%). $^1$H NMR (600 MHz, MeOD) δ 4.91 (s, 1H), 3.84 (dd, J=3.4, 1.8 Hz, 1H), 3.82-3.76 (m, 2H), 3.75-3.67 (m, 2H), 3.62 (m, 1H), 3.56-3.41 (m, 2H), 2.94 (t, J=7.0 Hz, 2H), 2.70 (t, J=7.2 Hz, 2H), 2.48 (t, J=7.2 Hz, 2H). HRMS (ESI) calcd for $C_{14}H_{28}NO_7S$ $[M+H]^+$: 354.1586, found 354.1602.

Compound 42 (0.12 mmol) in DMF (1 mL) was added EDC (0.12 mmol), HOBt (0.12 mmol), trimethylamine (0.2 mmol), and CT(PEG)$_{12}$ (0.1 mmol), and the resulting solution was stirred under nitrogen at rt for 12 h. The mixture was concentrated to dryness in vacuo, and the crude product was purified by column chromatography on silica gel to yield 44 (62%). $^1$H NMR (600 MHz, D$_2$O): δ 4.77 (d, J=8.6 Hz, 2H), 3.85-3.82 (m, 1H), 3.81-3.77 (m, 1H), 3.69-3.67 (m, 1H), 3.66-3.64 (m, 2H), 3.63-3.57 (m, 41H), 3.55-3.45 (m, 4H), 2.88 (t, J=6.8 Hz, 2H), 2.57 (t, J=7.2 Hz, 2H), 2.37 (t, J=7.2 Hz, 2H), 1.66-1.51 (m, 4H), 1.40-1.31 (m, 2H). $^{13}$C NMR (150 MHz, D$_2$O): δ 171.01, 99.62, 72.72, 70.57, 69.99, 69.24 (x22), 69.04, 67.90, 67.39, 66.73, 60.92, 39.36, 37.57, 27.96, 26.70, 22.91, 22.43. HRMS (ESI) calcd for $C_{38}H_{76}NO_{19}S$ $[M+H]^+$: 882.4732, found 882.4750.

Compound 45

Compound 15b (5 mmol) in MeOH was added to NaOMe (0.2 eq), and the resulting solution was stirred under nitrogen at rt for 2 h. The mixture was neutralized by IR-120, filtered, and concentrated to dryness in vacuo. It was then dissolved in anhydrous DCM (40 mL) and treated with imidazole (7.5 mmol) at 0° C., followed by the addition of TBDPSCl (5.5 mmol). The mixture was stirred at room temperature for 2.5 h under a nitrogen atmosphere. The reaction was quenched by the addition of MeOH. After stirring at room temperature for 10 min, the solvent was removed under reduced pressure to give a dry residue that was purified by column chromatography with MeOH/DCM (1/10) to give compound 45 (75%). $^1$H NMR (600 MHz, CDCl$_3$) δ 7.61 (m, 4H), 7.41-7.29 (m, 11H), 7.23-7.18 (m, 2H), 6.92 (d, J=9.3 Hz, 2H), 5.41 (s, 1H), 5.16 (s, 2H), 4.09 (s, 1H), 4.02-4.00 (dd, J=9.3, 3.4 Hz, 1H), 3.91 (t, J=9.3 Hz, 1H), 3.85 (d, J=5.1 Hz, 2H), 3.72-3.69 (m, 1H), 1.01, (s, 9H). $^{13}$C NMR (150 MHz, CDCl$_3$): 162.61, 135.64 (x4), 135.54 (x4), 132.73, 129.95 (x4), 128.64 (x4), 128.38, 128.33, 127.84 (x2), 127.81 (x2), 98.09, 71.41, 71.22, 70.22, 70.13, 64.89, 36.53, 31.48, 26.83 (x3), 19.19. HRMS (ESI) calcd for $C_{36}H_{42}NO_8Si$ $[M+H]^+$: 644.2680, found 644.2699.

Compound 44

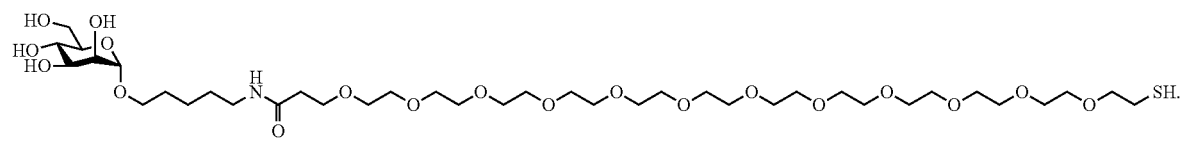

Compound 46

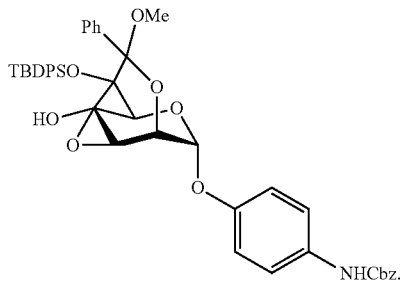

To a solution of compound 45 (3 mmol) and a catalytic amount of CSA (0.3 mmol) in $CH_3CN$ (60 mL) was added trimethyl orthobenzoate (9 mmol) at room temperature under atmospheric pressure of nitrogen. After stirring for 30 min, $Et_3N$ was added to quench the reaction, and the resulting mixture was dried under reduced pressure. The residue was purified by column chromatography with EA/Hex (1/2) to give compound 46 (81%). $^1H$ NMR (600 MHz, $CDCl_3$) δ 7.65-7.59 (m, 2H), 7.57-7.52 (m, 4H), 7.41-7.27 (m, 14H), 7.26-7.20 (m, 2H), 6.93 (d, J=9.2 Hz, 2H), 5.77 (s, 1H), 5.17 (s, 2H), 4.70 (d, J=6.1 Hz, 1H), 4.58 (dd, J=9.3, 3.4 Hz, 1H), 3.79-3.76 (m, 2H), 3.74-3.70 (m, 1H), 3.69-3.66 (m, 1H), 3.22 (s, 3H), 2.53 (d, J=3.9 Hz, 1H), 0.93, (s, 9H). $^{13}C$ NMR (150 MHz, $CDCl_3$): 171.23, 153.49, 152.24, 137.09, 136.09, 135.68 (x4), 135.48 (x4), 132.98, 132.72, 129.86, 129.84 (x2), 129.18, 128.65 (x2), 128.39, 128.37, 128.34, 127.78 (x2), 127.71 (x2), 126.23, 121.11, 117.18, 95.69, 79.52, 69.57, 69.45, 67.03, 63.75, 60.44, 51.16, 26.76 (x3), 19.15, 14.22. HRMS (ESI) calcd for $C_{44}H_{48}NO_9Si$ $[M+H]^+$:762.3098, found 762.3072.

Compound 47

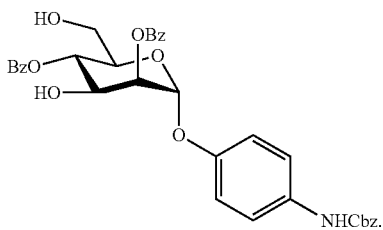

Compound 46 (2 mmol) was dissolved in DCM (20 mL) and sequentially mixed with DIPEA (6 mmol), benzoic anhydride (4 mmol), and DMAP (0.2 mmol). After stirring for 30 min, the solvent was evaporated under reduced pressure to give a dry residue and then poured into EA (20 mL) and 2 N HCl (20 mL) with vigorous stirring for 30 min. The solvent was removed by evaporation, followed by extraction with EA. The collected organic layer was washed with ice-cold saturated $NaHCO_3$(aq), water, and brine and dried over $MgSO_4$. The filtrate was evaporated under reduced pressure and redissolved in THF (20 mL). AcOH (4 mmol) and 1 M TBAF (2.4 mmol in THF) were added at 0° C. The resulting mixture was gradually warmed to room temperature, stirred for another 2 h, and then diluted with EA. The organic layer was washed with saturated $NaHCO_3$(aq), water, and brine, dried with anhydrous $MgSO_4$, and concentrated under reduced pressure. The dry residue was purified by column chromatography with EA/Hex (1/2) to give compound 47 (65%). $^1H$ NMR (600 MHz, $CDCl_3$) δ 8.10-8.05 (m, 4H), 7.61-7.56 (m, 2H), 7.48-7.41 (m, 4H), 7.39-7.27 (m, 7H), 7.03 (d, J=9.2 Hz, 2H), 5.69 (s, 1H), 5.62-5.55 (m, 2H), 5.16, (s, 2H), 4.62 (dd, J=9.3, 3.4 Hz, 1H), 4.06-4.01 (m, 1H), 3.76-3.67 (m, 2H). $^{13}C$ NMR (150 MHz, $CDCl_3$): 167.42, 166.05, 153.55, 152.01, 136.03, 133.84, 133.76, 130.00 (x4), 129.09, 128.96, 128.69 (x4), 128.65 (x4), 128.62 (x4), 128.34, 117.11 (x2), 96.18, 72.61, 71.30, 70.01, 68.53, 61.16. HRMS (ESI) calcd for $C_{34}H_{32}NO_{10}$ $[M+H]^+$: 614.2026, found 614.2038.

Compound 48

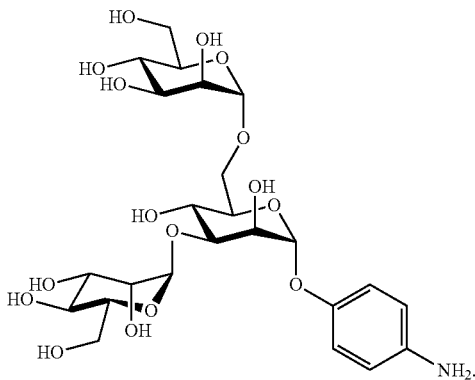

To a stirred solution of 47 (0.2 mmol) and 4 Å molecular sieve (0.2 g) in anhydrous DCM (2 mL) was cooled to −40° C. and then $BF_3(OEt)_2$ (0.02 mmol) was added dropwise to the solution. A solution of 15a in anhydrous DCM was added dropwise to the above mixture and stirred for 1 h at −40° C. After that, the reaction was gradually warmed to room temperature and stirred for another 1 h. The solution was quenched by adding triethylamine, then filtered and added sat. $NaHCO_3$ aq. and extracted with DCM. The organic layer was dried with $MgSO_4$ and evaporated to dryness. The residue was purified by flash column chromatography on silica gel to give a trisaccharide product. The product was then dissolved in MeOH, NaOMe (0.2 eq) was added, and the resulting solution was stirred at rt for 2 h. The mixture was neutralized by IR-120, filtered, and concentrated to dryness in vacuo. The deacetylated mixture was purified by Bio-Gel P-2 Gel (Biorad) with $H_2O$ as eluent to obtain a pure trisaccharide. The compound was lyophilized and then dissolved in MeOH (2 mL), and 10% Pd—C(30 mg) was added and stirred vigorously under an $H_2$ atmosphere overnight. The solution was filtered by celite and concentrated to dryness to give compound 48 (42%). $^1H$ NMR (600 MHz, $D_2O$) δ 7.03 (d, J=9.2 Hz, 2H), 6.88 (d, J=9.2 Hz, 2H), 5.48 (s, 1H), 5.19 (s, 1H), 4.76 (s, 1H), 4.32 (s, 1H), 4.14 (dd, J=9.3, 3.0 Hz, 1H), 4.11 (s, 1H), 3.95-3.63 (m, 15H). $^{13}C$ NMR (150 MHz, $D_2O$): 151.38, 143.39, 121.23, 120.70, 105.19, 101.60, 101.39, 80.93, 76.13, 75.38, 74.04, 73.27, 73.12, 72.79, 72.66, 72.22, 69.50, 69.41, 68.70, 67.90, 63.71, 63.65. HRMS (ESI) calcd for $C_{24}H_{37}NO_{16}Na[M+Na]^+$:618.2010, found 618.2029.

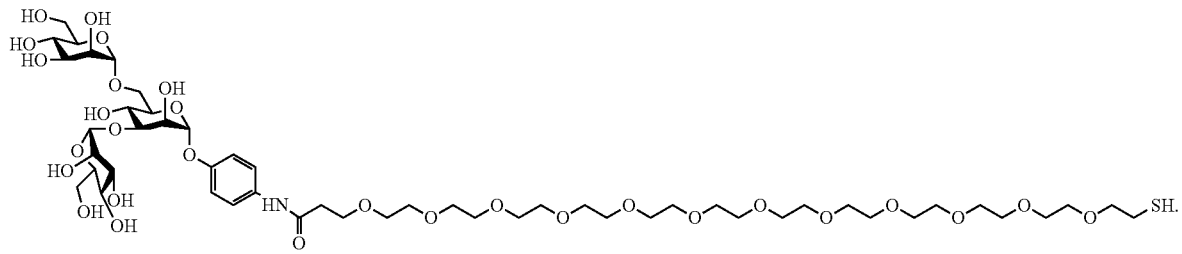

Compound 49

Compound 48 (0.12 mmol) in DMF (1 mL) was added EDC (0.12 mmol), HOBt (0.12 mmol), DMAP (0.12 mmol), trimethylamine (0.2 mmol), and CT(PEG)$_{12}$ (0.1 mmol), and the resulting solution was stirred under nitrogen at rt for 12 h. The mixture was concentrated to dryness in vacuo, and the crude product was purified Bio-Gel P-2 Gel with H$_2$O as eluent to yield 49 (54%). $^1$H NMR (600 MHz, D$_2$O): 7.20 (d, J=9.2 Hz, 2H), 7.13 (d, J=9.2 Hz, 2H), 5.53 (s, 1H), 5.09 (s, 1H), 4.65 (s, 1H), 4.25 (s, 1H), 4.06 (dd, J=9.3, 3.0 Hz, 1H), 4.01 (m, 1H), 3.83-3.67 (m, 11H), 3.61-3.56 (m, 52H), 2.64 (t, J=6.4 Hz, 2H), 2.48 (t, J=6.4 Hz, 2H). $^{13}$C NMR (150 MHz, D$_2$O): 178.06, 153.84, 149.84, 123.02, 118.11, 120.42, 98.8, 97.78, 78.05, 73.39, 72.61, 72.17, 71.47, 70.52, 70.35, 70.01, 69.85, 69.55, 69.38, 69.31, 69.17, 66.97, 66.74, 66.60, 65.82, 65.10, 60.96, 60.86, 35.82, 23.03. HRMS (ESI) calcd for C$_{51}$H$_{89}$NO$_{29}$SNa[M+Na]$^+$: 1234.5139, found 1234.5114.

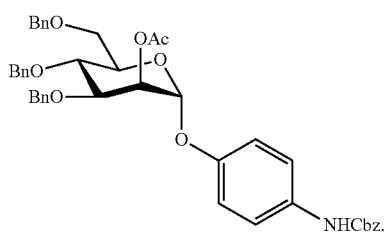

Compound 51

To a stirred solution of 50 (1 mmol) in anhydrous DCM (10 mL), trichloroacetonitrile and DBU were added, and the solution was stirred for 2 h at rt. The solvent was removed, and the residue was purified by flash column chromatography on silica gel to give an imidate product. A stirred solution of benzyl (4-hydroxyphenyl)carbamate (1.2 mmol) and 4 A molecular sieve (1 g) in anhydrous DCM (10 mL) was cooled to −40° C., and then BF$_3$(OEt)$_2$ (0.1 mmol) was added dropwise to the solution. A solution of imidate donor (1 mmol) in anhydrous DCM was added dropwise to the above mixture and stirred for 1 h at −40° C. After that, the reaction was gradually warmed to room temperature and stirred for another 1 h. The solution was quenched by adding triethylamine, then filtered and added sat. NaHCO$_3$ aq. and extracted with DCM. The organic layer was dried with MgSO$_4$ and evaporated to dryness. The residue was purified by flash column chromatography on silica gel to give compound 51 (72%). $^1$H NMR (600 MHz, CDCl$_3$) δ 7.40-7.28 (m, 18H), 7.19 (d, J=7.9 Hz, 2H), 7.10 (d, J=8.1 Hz, 2H), 7.00 (d, J=8.1 Hz, 2H), 5.57-5.55 (m, 2H), 5.12 (s, 2H), 4.91 (d, J=10.5 Hz, 1H), 4.80 (d, J=10.5 Hz, 1H), 4.69 (d, J=10.5 Hz, 1H), 4.65 (d, J=10.5 Hz, 1H), 4.53 (d, J=10.5 Hz, 1H), 4.46 (d, J=10.5 Hz, 1H), 4.22 (dd, J=9.4, 3.6 Hz, 1H), 4.07-4.04 (t, J=9.7 Hz, 1H), 3.93 (d, J=9.5 Hz, 1H), 3.83 (dd, J=10.9, 3.9 Hz, 1H), 3.68 (d, J=10.8 Hz, 1H), 2.21 (s, 3H). $^{13}$C NMR (150 MHz, CDCl$_3$): 170.44, 156.25, 154.62, 138.27, 138.04, 137.82, 136.51, 132.71, 129.79, 128.50, 128.43, 128.31, 128.27, 128.10, 128.08, 127.83, 127.80, 127.64, 127.60, 116.63, 96.13, 77.95, 76.66, 75.22, 74.00, 73.34, 71.99, 71.92, 68.55, 68.5, 66.63, 21.09. HRMS (ESI) calcd for C$_{43}$H$_{43}$NO$_{10}$ [M+H]$^+$:718.3016, found 718.3041.

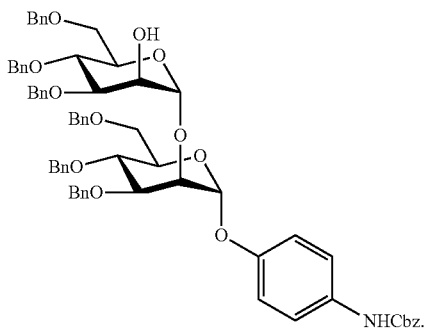

Compound 52

To a stirred solution of 51 (0.6 mmol) in MeOH was added NaOMe (0.1 eq), and the resulting solution was stirred at rt for 1 h. The mixture was neutralized by IR-120, filtered, and concentrated to dryness in vacuo. The deacetylated product was then dissolved in anhydrous DCM (5 mL) with 4 A molecular sieve (0.5 g) added. The solution was cooled to −40° C., and then BF$_3$(OEt)$_2$ (0.05 mmol) was added dropwise to it. A solution of imidate donor (0.5 mmol) in anhydrous DCM was added dropwise to the above mixture and stirred for 1 h at −40° C. After that, the reaction was gradually warmed to room temperature and stirred for another 1 h. The solution was quenched by adding triethylamine, then filtered and added sat. NaHCO$_3$ aq. and extracted with DCM. The organic layer was dried with MgSO$_4$ and evaporated to dryness. The product was then dissolved in MeOH, NaOMe (0.1 eq) was added, and the resulting solution was stirred at rt for 2 h. The mixture was neutralized by IR-120, filtered, and concentrated to dryness in vacuo. The residue was purified by flash column chromatography on silica gel to give compound 52 (69%). $^1$H NMR (600 MHz, CDCl$_3$) δ 7.36-7.25 (m, 25H), 7.22-7.13 (m, 10H), 6.99-6.93 (m, 4H), 5.66 (s, 1H), 5.17 (s, 1H), 5.06 (s, 2H), 4.86 (d, J=10.5 Hz, 1H), 4.79 (d, J=10.5 Hz, 1H), 4.73, (s, 2H), 4.65 (d, J=10.5 Hz, 1H), 4.58-4.57 (m, 2H), 4.55-4.52 (m, 2H), 4.47-4.43 (m, 3H), 4.19-4.14 (m, 2H), 3.99-3.96 (m, 2H), 3.88 (dd, J=9.1, 3.1 Hz, 1H), 3.84-3.76 (m, 3H), 3.67-3.63 (m, 3H). $^{13}$C NMR (150 MHz, CDCl$_3$):

156.22, 154.70, 138.47, 138.35, 138.18, 138.14, 138.05, 137.90, 136.51, 132.30, 129.74, 129.63, 128.46, 128.44, 128.31, 128.28, 128.26, 128.19, 128.06, 127.93, 127.85, 127.83, 127.74, 127.68, 127.60, 127.54, 127.46, 127.38, 127.32, 116.63, 101.12, 96.95, 79.97, 79.42, 77.21, 77.00, 76.78, 75.12, 75.02, 74.66, 74.45, 74.33, 73.23, 73.16, 72.44, 72.41, 72.16, 71.69, 68.99, 68.45, 66.57. HRMS (ESI) calcd for $C_{68}H_{70}NO_{13}$ [M+H]$^+$: 1108.4847, found 1108.4819 celite and concentrated to dryness to give compound 53 (60%). $^1$H NMR (600 MHz, D$_2$O) δ 7.03 (d, J=9.0 Hz, 2H), 6.83 (d, J=9.0 Hz, 2H), 5.09 (s, 1H), 4.81 (s, 1H), 3.94-3.55 (m, 16H), 3.48 (t, J=9.6 Hz, 1H), 3.29-3.27 (m, 1H). $^{13}$C NMR (150 MHz, D$_2$O): 151.36, 143.37, 121.20, 120.67, 101.59, 101.23, 96.33, 78.46, 75.34, 74.69, 73.51, 73.11, 72.97, 72.52, 71.53, 69.28, 69.14, 68.90, 65.51, 63.26, 62.91. HRMS (ESI) calcd for $C_{24}H_{38}NO_{16}$ [M+H]$^+$: 596.2191, found 596.2044.

Compound 54

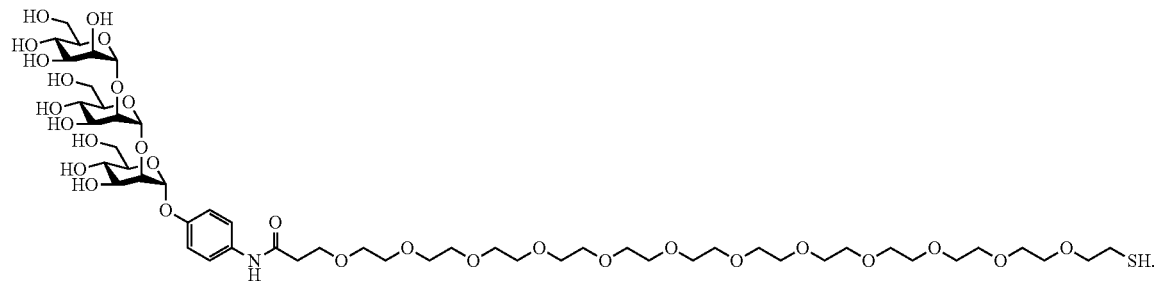

Compound 53

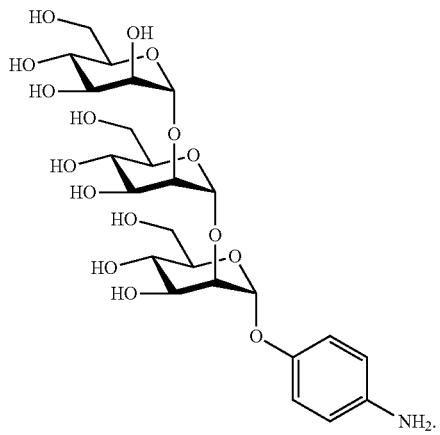

A stirred solution of 52 (0.3 mmol) in anhydrous DCM (2.5 mL) with 4 A molecular sieve (0.25 g) was added. The solution was cooled to −40° C., and then BF$_3$(OEt)$_2$ (0.03 mmol) was added dropwise to it. A solution of imidate donor (0.3 mmol) in anhydrous DCM was added dropwise to the above mixture and stirred for 1 h at −40° C. After that, the reaction was gradually warmed to room temperature and stirred for another 1 h. The solution was quenched by adding triethylamine, then filtered and added sat. NaHCO$_3$ aq. and extracted with DCM. The organic layer was dried with MgSO$_4$ and evaporated to dryness. The residue was purified by flash column chromatography on silica gel to give the trisaccharide product. The product was then dissolved in MeOH, NaOMe (0.1 eq) was added, and the resulting solution was stirred at rt for 2 h. The mixture was neutralized by IR-120, filtered, and concentrated to dryness in vacuo. The compound was then dissolved in MeOH (2 mL), and 10% Pd—C(30 mg) was added and stirred vigorously under an H$_2$ atmosphere overnight. The solution was filtered by Compound 53 (0.02 mmol) in DMF (0.2 mL) was added EDC (0.02 mmol), HOBt (0.02 mmol), DMAP(0.02 mmol), trimethylamine (0.04 mmol), and CT(PEG)$_{12}$ (0.02 mmol), and the resulting solution was stirred under nitrogen at rt for 12 h. The mixture was concentrated to dryness in vacuo, and the crude product was purified Bio-Gel P-2 Gel with H$_2$O as eluent to yield 54 (58%). $^1$H NMR (600 MHz, D$_2$O): 7.03 (d, J=9.2 Hz, 2H), 6.82 (d, J=9.2 Hz, 2H), 5.09 (s, 1H), 4.81 (s, 1H), 3.84-3.46 (m, 65H), 3.30-3.26 (m, 1H), 2.65 (t, J=6.5 Hz, 2H), 2.52 (s, 2H). $^{13}$C NMR (150 MHz, D$_2$O): 173.22, 151.36, 143.37, 121.37, 120.59, 101.20, 101.67, 97.04, 79.17, 76.06, 75.40, 75.22, 74.23, 73.69, 73.23, 72.60, 72.45, 72.22, 71.68, 71.21, 69.85, 69.61, 63.97, 38.52, 26.08. HRMS (ESI) calcd for $C_{51}H_{90}NO_{29}S$[M+H]$^+$: 1212.5319, found 1212.5146.

Preparation of the Polymersomes.

Figure 1B:
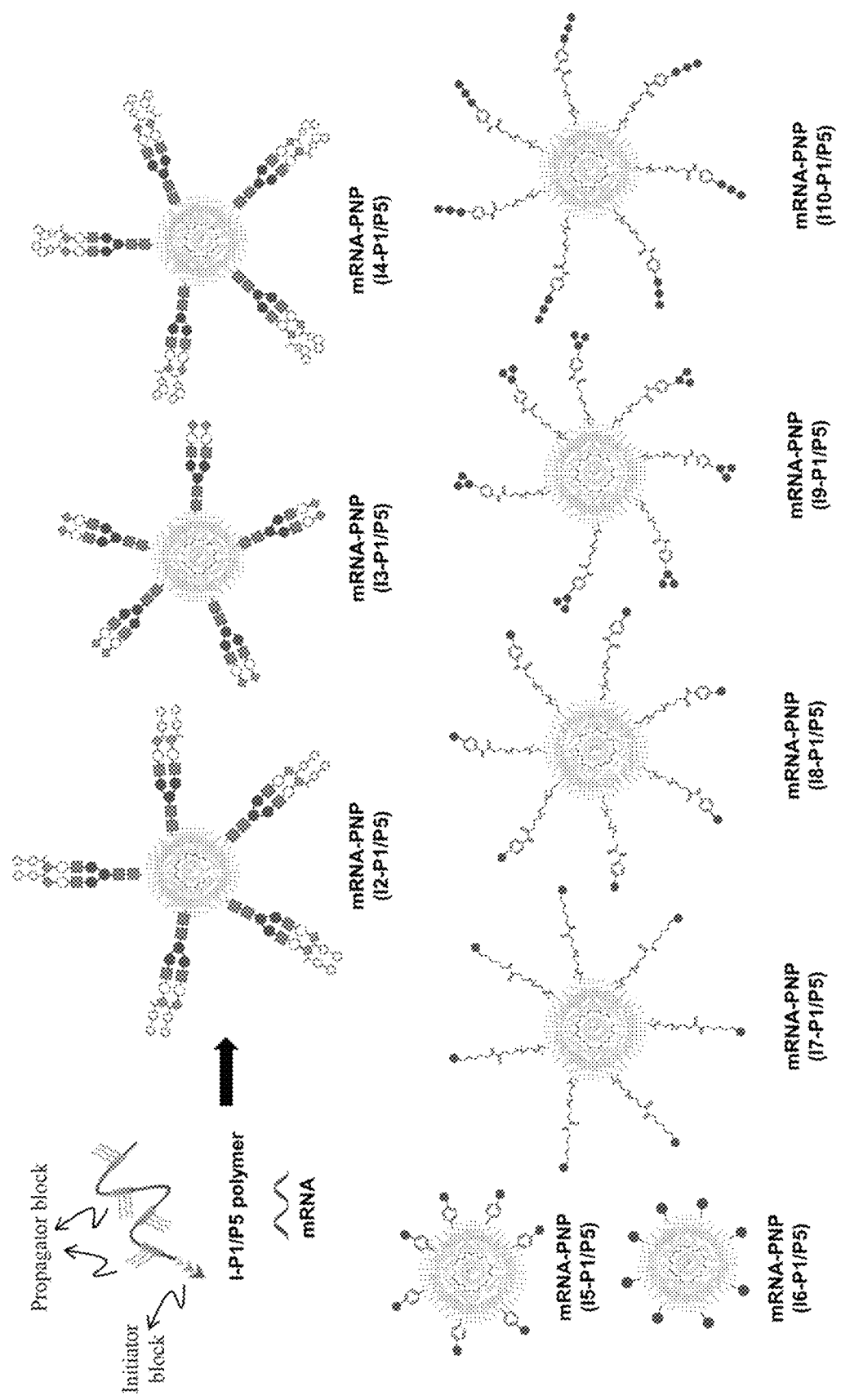
FIG. 1B illustrates the structures of some exemplary polymersomes comprising copolymers according to some embodiments of the present disclosures.

In this example, polymersomes of the present disclosure encapsulating mRNA to form mRNA-polymer nanoparticles (PNPs) for delivery were prepared. The term "PNP" is used interchangeably with "polymersome" to describe the polymersomes of the present disclosure. Exemplary PNPs included I2-P1/P5 mRNA-PNP, I3-P1/P5 mRNA-PNP, I4-P1/P5 mRNA-PNP, I5-P1/P5 mRNA-PNP, I6-P1/P5 mRNA-PNP, I7-P1/P5 mRNA-PNP, I8-P1/P5 mRNA-PNP, I9-P1/P5 mRNA PNP, and I10-P1/P5 mRNA PNP, which are illustrated in FIG. 1B.

WT Spike DNA Construction.

pMRNA$^{XP}$ mRNA Synthesis Vector was obtained from System Biosciences. WT (Wuhan/WHO1/2019 strain) spike DNA sequence with K986P and K987P mutations (2P) was codon-optimized for Homo sapiens.[1] pMRNA$^{XP}$ vector was digested with EcoRI and BamHI at 37° C. for 1 hour. The DNA sequence of the spike protein was amplified by the KOD One™ PCR master mix (TOYOBO Bio-Technology). The linearized pMRNAXP vector and the PCR fragment of spike protein DNA were cleaned up by Wizard SV Gel and PCR Clean-Up System (Promega). The PCR fragment of spike protein DNA was cloned into a linearized pMRNAXP vector using In-Fusion HD Cloning Kit (Clontech Laboratories, Inc.). The cloning mixture was transformed to One Shot™ TOP10 Chemically Competent E. coli (Invitrogen™) and incubated at 37° C. overnight. Quick Taq HS DyeMix (TOYOBO Bio-Technology) was used to screen for successful construction. Insert-specific primer and backbone-specific primer were designed for colony PCR. A single clone was selected by pipet tip to conduct PCR. The PCR products were analyzed using agarose gel electrophoresis. The possible candidates were selected and analyzed by DNA sequencing.

Synthesis of Polymers.

The polymerization process was done according to published procedures, as described in Jiaqi Fu et al., Journal of the American Chemical Society 2015 137 (37), 12153-12160, which is herein incorporated by reference in its entirety. Modifications were made where applicable. Briefly, stock solutions of the monomers (i.e., propagator. 2 M in DMF), initiators (50 mM in DMF, freshly prepared), terminator (iodoacetamide, 0.5 M in $H_2O$, freshly prepared), and triethanolamine (TEOA) buffer (1 M, pH=7.0) were prepared. The initiator was added to 80 L of mixture buffer (DMF/TEOA=1/1) and 10 L of the monomer stock solution (a v/v ratio of 1:1 was used for hetero-polymers P1/P3, P2/P3, P1/P4, P2/P4, P1/P5, and P2/P5). See FIG. 1A. After 30 min of agitation at room temperature, the polymerization reaction was quenched by adding 1.9 mL of the terminator stock solution. The resulting polymer was dialyzed against $H_2O$ on the same day. The solution was lyophilized and the polymers were kept at −20° C. For the in vitro and in vivo experiments, the initiator was mixed with 5% IP, followed by the same protocol mentioned above.

For the formulation of mRNA-PNP, the mRNA was encapsulated in a corresponding polymer using a self-assembly process; that is, the polymer in the ethanol phase (10 mg/mL) was mixed with an aqueous solution of mRNA (1 mg/mL) at pH 4.0 in a 3 to 1 N/P ratio. See FIG. 1B. The mRNA-PNP was dialyzed against PBS buffer (pH 7.4) using Micro Float-A-Lyzer (10 kDa MWCO, spectrum lab) overnight at 4° C. and stored at −40° C. until further use.

Characterization of the Polymersomes.

To examine the morphology of the mRNA-polymer complex, we first mixed the P1 polymer with mRNA, and it was found to form a nearly spherical nanoparticle. The complex of P1/P5 co-polymer with mRNA was liposome-like. The polymers are likely to form a layer with a positive charge, which can encapsulate the mRNA and facilitate subsequent cellular uptake through the engagement of the zwitterion.

The molecular weight and polymerization index were characterized by gel permeation chromatography (GPC). The polymers displayed an unimodal but rather broad molecular weight distribution in the GPC chromatogram and were eluted at a relatively low elution time, indicating their polymeric state. The peak molecular weight was 10.2 kDa (PDI=1.33) for mRNA-PNP (P1/P5).

Example 2: Encapsulation and Transfection Efficiency of the Polymersomes

To identify the optimal polymer for efficient intracellular delivery of GFP-mRNA as a model, homo-polymers and hetero-copolymers were synthesized by co-polymerization of different propagators, and their encapsulation ability and transfection efficiency in HEK293T cells were evaluated.

Quantification of Encapsulated mRNA.

Encapsulation efficiency was determined by Quant-iT™ RiboGreen™ RNA Reagent and Kit (Thermo Scientific™). The prepared mRNA polymersome (mRNA-PNP) was treated with 10 mM GSH overnight. Then, the solution was diluted 250-fold with 1×TE buffer and further diluted 2-fold with TE buffer or TE buffer containing 2% Triton X-100. mRNAs were prepared as 100, 50, 25, 12.5, and 0 ng/ml in TE or TE buffer containing 1% Triton X-100 to establish the standard curve. After incubation at 37° C. for 10 minutes, Quant-iT™ RiboGreen™ RNA Reagent was added to the well. The fluorescence intensity was measured by CLARIOstar® Plus (BMG Labtech).

Result.

Figure 2A:
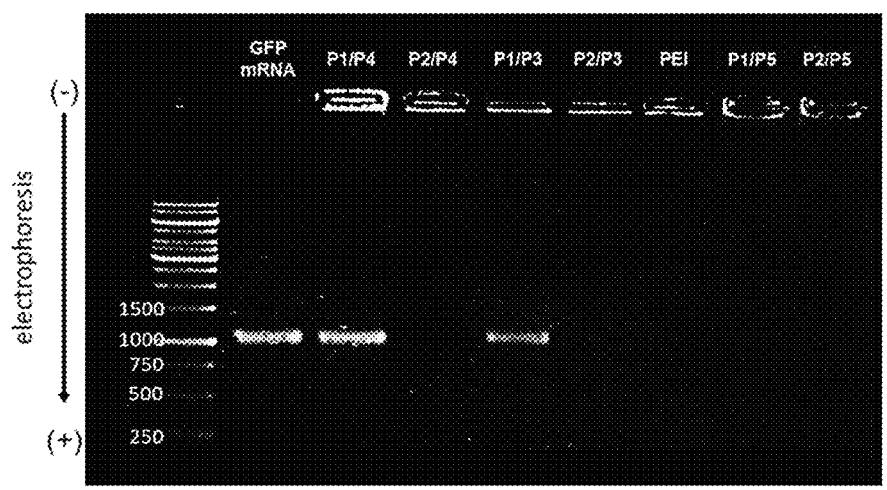
FIG. 2A shows the results of an agarose gel electrophoresis assay, which shows the encapsulation efficiency of several exemplary copolymers according to some embodiments of the present disclosures. The payload in this efficacy-demonstrating assay was a GFP mRNA of about 920 bp. The copolymers, with or without the GFP mRNA, had a size larger than 10 kDa.

All the copolymers containing the guanidine group were able to encapsulate GFP-mRNA. Particularly, the I1-P2/P3, I1-P2/P4, and I1-P2/P5 copolymers with tri-valent guanidine moieties exhibited higher capability to encapsulate the mRNA and were comparable with the result with the traditional transfection agent polyethyleneimine (PEI). See FIG. 2A.

Formulation of WT Spike mRNA to Form mRNA-PNP.

To obtain the WT spike mRNA, the linear DNA that contained the T7 promoter, 50 untranslated regions, 30 untranslated regions, S-2P, and poly(A) tail signal sequence was amplified by using TOOLS Ultra High Fidelity DNA Polymerase (BIOTOOLS Co., Ltd.) with one L of the DNA template in a mMESSAGE mMACHINE™ Kit (Thermo Scientific) at 37° C. for 1 h according to the manufacturer's protocol. The mRNA was purified by RNA cleanup kit (BioLabs) according to the manufacturer's protocol and stored at −80° C. until further use. For the formulation of mRNA-PNP, the mRNA was encapsulated in a corresponding polymer using a self-assembly process; that is, the polymer in the ethanol phase (10 mg/mL) was mixed with an aqueous solution of mRNA (1 mg/mL) at pH 4.0 at different N/P ratios. The mRNA-PNP was dialyzed against PBS buffer (pH 7.4) using Micro Float-A-Lyzer (10 kDa MWCO, spectrum lab) overnight at 4° C. and stored at −40° C. until further use.

Result.

Figure 3A:
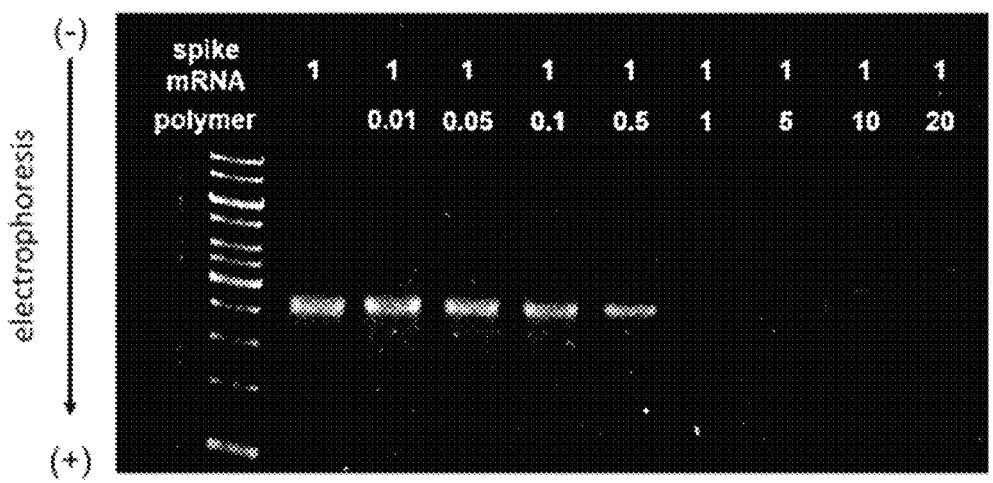
FIG. 3A shows the results of an agarose gel electrophoresis assay demonstrating the encapsulation efficiency of several copolymers according to some working embodiments of the present disclosures. The payload in this demonstration assay was a spike mRNA having a size of about 2550 bp. The exemplary copolymers, with or without the spike mRNA, had a size larger than 10 kDa. The N/P ratio (positively-chargeable polymer amine groups (N=nitrogen) to negatively-charged nucleic acid phosphate (P) groups) of each experimental group is shown by the numbers indicated at each lane. The N/P ratios tested in this experiment were 0.01, 0.05, 0.1, 0.5, 1, 5, 10, and 20.
Figure 3B:
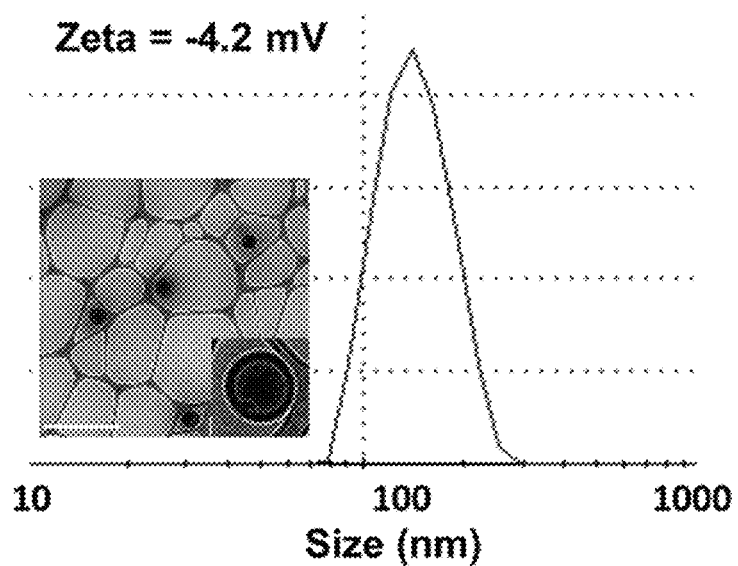
FIG. 3B provides a graphic representation showing the particle size and zeta (ζ) potential of mRNA-PNP (P1/P5) with CryoEM image and insets.

The result showed that the P1/P5 co-polymer exhibited an excellent ability to capture spike mRNA at the N/P ratio of 1, 5, 10, or 20 (FIG. 3A), and the average particle size of the resulting mRNA-P1/P5 co-polymer complex was ca. 127 nm, as revealed by CryoEM, TEM and dynamic light scattering (DLS) analysis (FIG. 3B). The zeta potential measured was about −4.2 mV. An N/P ratio of 3 was chosen for the following experiments to ensure full encapsulation. The release and translation of mRNA may be attributed to GSH-mediated polymer degradation, as it takes place in the presence of 10 mM GSH in a time-dependent manner (data not shown).

HEK293T Cell Transfection.

Transfection of Polymersomes Encapsulating GFP-mRNA.

Next, we evaluated the transfection efficiency of GFP-mRNA in HEK293T cells by using different copolymers. HEK293T cells were plated at $5 \times 10^5$ cells per well in a 6-well plate in 2.5 mL DMEM media. 1 μg of the GFP mRNA or 3 μg of WT spike mRNA was formulated with the corresponding polymer by the abovementioned procedure and then added to the cells. 18 hours post-transfection, GFP and spike expression were monitored by fluorescence microscopy and western blotting, respectively. For the WB, cells containing spike protein were lysed with 200 L RIPA lysis buffer, including a protease inhibitor, and incubated for 10 minutes. Cells were then vortexed, centrifuged, and analyzed by western blot with polyclonal anti-SARS-CoV-2 S protein antibodies (1:5000 with 1% BSA) followed by HRP conjugated anti-rabbit antibody (1:10000). The spike protein was detected by chemiluminescent HRP substrate and visualized by a trans-illuminator (FUJIFILM LAS3000).

Result.

Figure 2B:
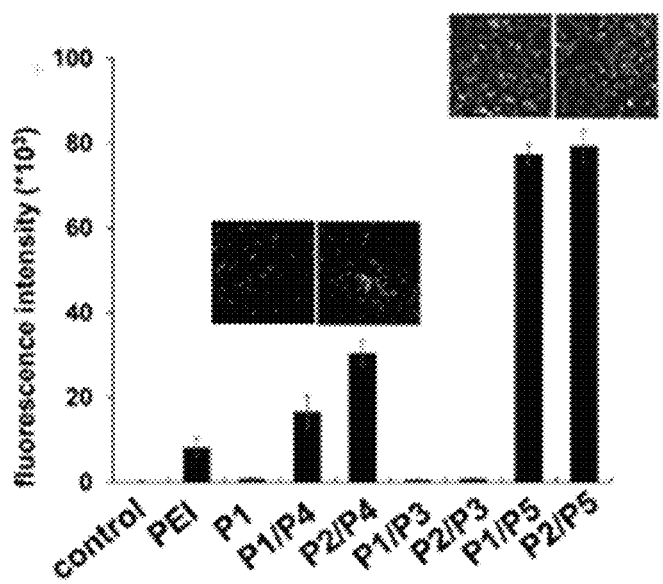
FIG. 2B provides a graphic representation showing the means fluorescence intensity of HEK293 cells after transfection with polymersomes encapsulating GFP-mRNA according to some working embodiments of the present disclosure.

The result indicated that copolymer P1 exhibited comparable capability to transfect HEK293T cells as the traditional transfection agent polyethyleneimine (PEI), while the hetero-polymer P1/P4, P2/P4, P1/P5, and P2/P5 showed superior transfection efficiency and were able to release the mRNA for translation to GFP. Particularly, the polymer containing the zwitterionic group, P1/P5 and P2/P5 (FIG. 2B), was highly effective, probably due to membrane fusion as described above. All the tested polymersomes exhibited less impact on the cell viability than the traditional transfection agent PEI, and none exhibited apparent cytotoxicity (data not shown).

Transfection of Polymersomes Encapsulating WT Spike mRNA.

Figure 3C:
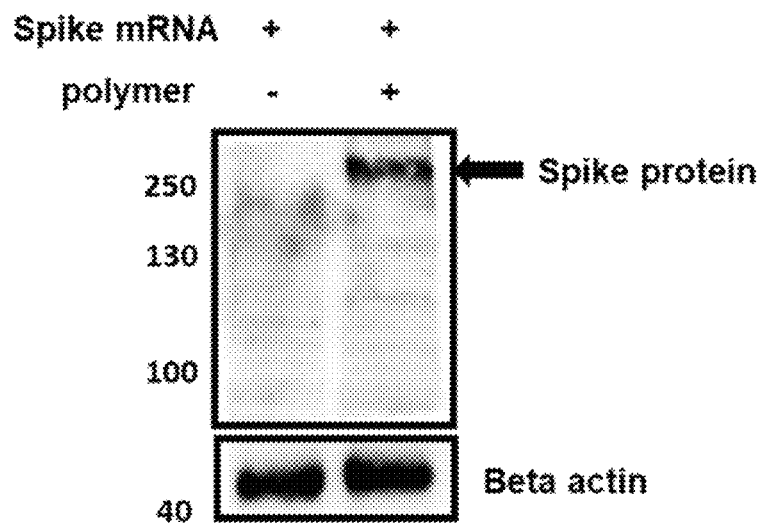
FIG. 3C shows a chemiluminescent image demonstrating the spike protein expression mediated by spike mRNA-PNP (I1-P1/P5) in HEK293T cells. The first lane shows the protein expression from cells transfected with the spike mRNA, and the second lane shows the protein expression from cells transfected with the spike mRNA-PNP (I1-P1/P5). Beta-actin was used as a benchmark expression in this experiment.

We then transfected the spike mRNA-P1/P5 complex (3 μg) in HEK293T cells and performed western blotting. After 48 h post-transfection, cells were analyzed for spike-protein translation by western blotting with spike-specific antibodies. A significant band at ~250 kDa corresponding to SARS-CoV-2 spike protein was observed (the second lane) compared to the spike mRNA as negative control (the first lane) (FIG. 3C). This study confirmed that P1/P5 co-polymer is an effective nanocarrier for mRNA transfection in vitro.

Location of mRNA-PNP in Cells.

Figure 4:
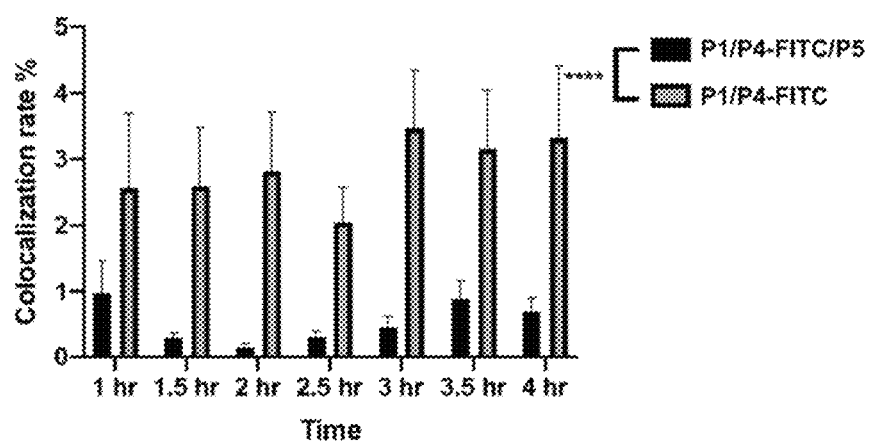
FIG. 4 provides a graphic representation of the colocalization of lysosome and mRNA-PNP in cells, investigated using confocal fluorescence imaging over four hours. Images were collected at Hours 1, 1.5, 2, 2.5, 3, 3.5, and 4, respectively. The mRNA-PNP was labeled with FITC for detection.

To visualize the location of mRNA-PNP in cells, a FITC-labelled polymer was synthesized from P1/P4/P5, in which FITC was conjugated to the polymer through the amine group on P4. As shown in FIG. 4, the colocalization of the lysosome with mRNA-PNP (I1-P1/P4/P5) was lower than that of the mRNA-PNP (I1-P1/P4), indicating that the alkylated zwitterion residue may significantly improve membrane fusion and lysosomal escape.

Example 3: Targeted (Selectively) Delivery

To selectively deliver the mRNA vaccine to antigen-presenting cells (APCs), especially dendritic cells, we designed the initiators with different glycan heads recognized by the lectin receptors such as Siglec-1, Siglec-2, Siglec-5/E, and DC-SIGN, which are expressed predominantly on DCs and macrophages. To assess mRNA-PNP uptake via Siglecs, we compared the binding and internalization of mRNA-PNP into T cells, B cells, and bone marrow-derived dendritic cells (BMDCs).

Methods

Splenic cell preparation and BMDCs culture. To prepare splenic cells, the mouse spleen was homogenized with the frosted end of a glass slide and treated with RBC lysis buffer (Sigma) to deplete red blood cells (RBCs), followed by passing through the cell strainer (BD Biosciences). Bone-marrow-derived dendritic cells (BMDCs) were prepared as described.[3] Briefly, bone marrow was isolated from mouse femurs and tibiae and treated with RBC lysis buffer (Sigma-Aldrich) to deplete RBCs. Cells were then cultured in RPMI-1640 containing 10% heat-inactivated FBS (Thermo Fisher Scientific), 1% Penicillin/Streptomycin (Thermo Fisher Scientific), 50 μM 2-mercaptoethanol (Thermo Fisher Scientific), and 20 ng/ml recombinant mouse GM-CSF (eBioscience) at a density of 2×105 cells/ml. The cells were supplemented with an equal volume of the complete culture medium described above on day 3 and refreshed with one-half the volume of the medium on day 6. On day 8, the suspended cells were harvested.

Treatment of PNP to Splenic Cells and BMDCs.

Splenic cells or BMDCs were incubated with 1:2000 mRNA-PNP (diluted by 10 mg/mL) in RPMI-1640 at 37° C. for 24 hours. Cells were blocked with an Fc receptor binding inhibitor (clone: 93, eBioscience) for 20 minutes. Splenocytes were stained with antibodies against CD3 (clone: 17A2, BV421-conjugated, Biolegend), CD19 (clone: 1D3, PECy7-conjugated, BD Biosciences). BMDCs were stained with antibodies against CD11c (clone N418 APC-conjugated, Biolegend). Labeled cells were analyzed using FACSC and How Cytometer (BD Biosciences).

C2C12 Cell Culture.

The mouse muscle myoblast cell line C2C12 was purchased from Taiwan's Bioresource Collection and Research Center. C2C12 cells were cultured in DMEM with high-glucose (ATCC) supplemented with 10% FBS and 1× antibiotic-antimycotic. Cells were incubated at 37° C. with 5% $CO_2$ and humidified atmosphere control. The culture medium was changed every 2 to 3 days.

Treatment of Polymersomes to C2C12.

Cultured C2C12 myoblasts were detached from a culture dish using 0.25% Trypsin-EDTA (Gibco) and neutralized with a growth medium containing 10% FBS. mRNA-PNP (I1-P1/P4-FITC-P5) or mRNA-PNP (I9-P1/P4-FITC/P5) were added to 200 μL C2C12 cells (2×10$^5$ cells) in growth medium to reach a final dilution of 1:1000, 1:2000, 1:4000, or 1:8000 to the original stocks (10 mg/mL). Three time points were measured: 5 min, 1 hr, and 24 hr.

Flow Cytometry.

After incubation with mRNA-PNP, BMDC cells were washed with ice-cold FACS buffer (1% FBS in 1×DPBS with 0.1% Sodium Azide) and incubated with purified anti-mouse CD16/32 antibody (BioLegend) in FACS buffer on ice for 20 min, followed by washing with FACS buffer. BMDCs were stained with APC anti-mouse CD11c antibody (BioLengend) at 4° C. for 30 min and washed with FACS buffer. Finally, BMDCs were stained with propidium iodide (Sigma-Aldrich). C2C12 cells were centrifuged and washed with FACS buffer. Cells were stained with propidium iodide. Flow cytometry was performed on the FACSCanto flow cytometer (BD Bioscience).

Glycan-PNP and DC-SIGN Binding Assay Via ELISA.

To assess the binding of DC-SIGN to mannoside-modified PNP, ELISA plates were coated with mRNA-PNP(I5-P1/P5), mRNA-PNP (I6-P1/P5), mRNA-PNP (I7-P1/P5), mRNA-PNP (I8-P1/P5), mRNA-PNP(I9-P1/P5), or mRNA-PNP(I10-P1/P5) (10 mg/mL) in PBS at 4° C. overnight, respectively. The plates were incubated with diluted DC-SIGN ECD (15 to 0.075 nM in HEPES buffer containing 20 mM HEPES, 150 mM NaCl, 10 mM $CaCl_2$, 0.1% BSA) at pH 7.4, 6.0, and 5.0 for 1 h at rt. The bound DC-SIGN ECD was detected using HRP-conjugated anti-DC-SIGN (B2) IgG antibody (Santa Cruz Biotechnology). After 1 h of incubation at rt, the plates were treated with tetramethlybenzidine (TMB) for 10 min. The optical density was measured at 450 nm after adding 0.5 M sulfuric acid to the plates using a microplate reader. The apparent Kd was calculated using a nonlinear regression curve fit for total binding using GraphPad Prism.

Glycan-PNP Binding Assay to DC-SIGN-Fc, MMR-Fc, MINCLE-Fc, Dectin-2-Fc, and Langerin-Fc Via ELISA.

To assess the binding of receptor proteins to mannoside-modified PNP, ELISA plates were coated with mRNA-PNP (I1-P1/P5), mRNA-PNP (I8-P1/P5), mRNA-PNP (I9-P1/P5), or mRNA-PNP (I10-P1/P5) (10 mg/mL) in PBS at 4° C. overnight, respectively. The plates were incubated with diluted DC-SIGN-Fe, MMR-Fc, MINCLE-Fe, Dectin-2-Fe, and Langerin-Fe (0.625 g/mL in buffer) at pH 7.4 for 1 h at rt. The bound proteins were detected using HRP-conjugated anti-Fc IgG antibody. After 1 h of incubation at rt, the plates were treated with tetramethlybenzidine (TMB) for 10 min. The mean optical density was measured at 450 nm after adding 0.5 M sulfuric acid to the plates using a microplate reader.

Results

Figure 5:
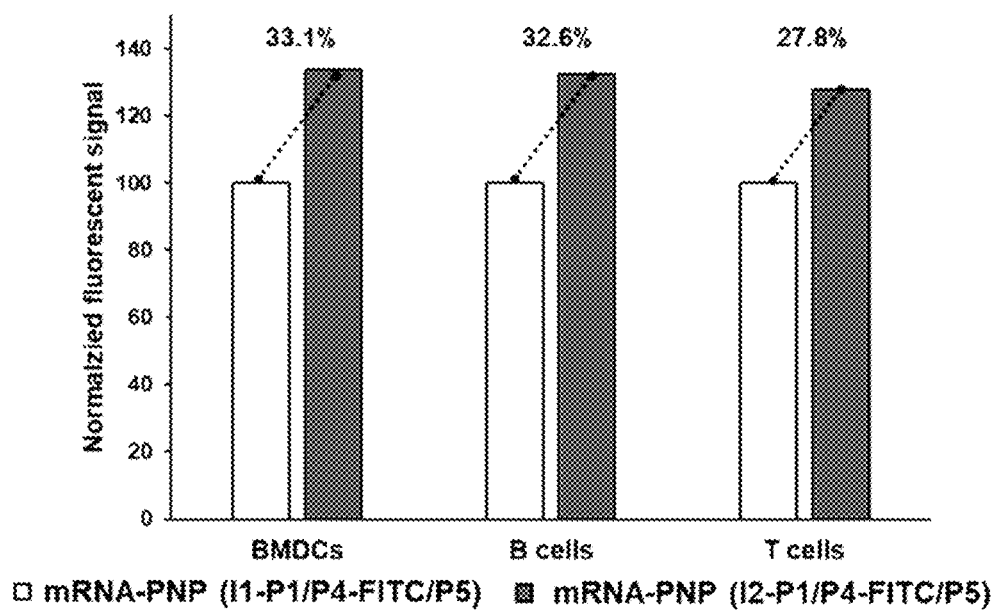
FIG. 5 provides a graphic representation showing the cellular uptake fluorescence signal of BMDC, B cells, and T cells treated with spike mRNA-PNP (I1-P1/P4-FITC/P5) or spike mRNA-PNP (I2-P1/P4-FITC/P5) targeting Siglec-2 after one h. The data was collected using flow cytometry analysis.
Figure 9:
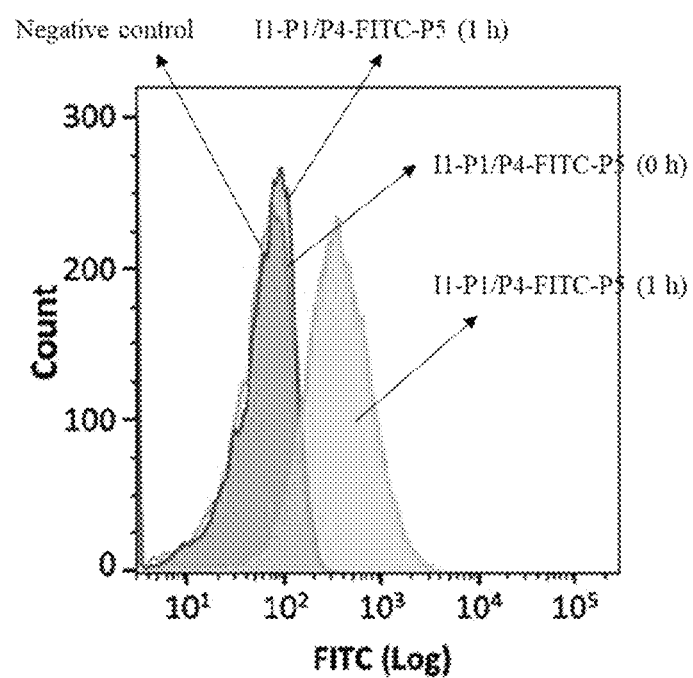
FIG. 9 is a graphic representation showing FACS data of C2C12 muscle cell uptake of the polymersomes of the present disclosure (at 0 hours and 1 hour after treatment) and the polymersomes without the targeting glycan (at 1 hour after treatment).

As evaluated by flow cytometry, FITC-conjugated mRNA-PNP was incubated with each cell line for 1 h. The 12 mRNA-PNP with 9BPCNeu5Ac conjugated N-glycan intended to target Siglec-2 showed a higher cellular uptake by all APCs compared to I1 mRNA-PNP without glycan modification (FIG. 5). Specifically, in this experiment, in comparison with I1 polymersomes, I2 polymersomes showed 33.1% increase, 32.6% increase, and 27.8% increase in BMDCs, B cells, and T cells uptake, respectively. Similar results were obtained by using I3 and I4 mRNA-PNP to target Siglec-5/E and Siglec-1, respectively, in which all glycan-decorated polymersomes exhibited a better uptake by all APCs than the glycan-free mRNA-PNP. Similarly, the I9-P1/P4-FITC/P5 mRNA-PNP exhibited higher (about 1 time higher, FIG. 9) uptake by C2C12 muscle cells compared with I1-P1/P4-FITC-P5 mRNA-PNP.

Figure 6:
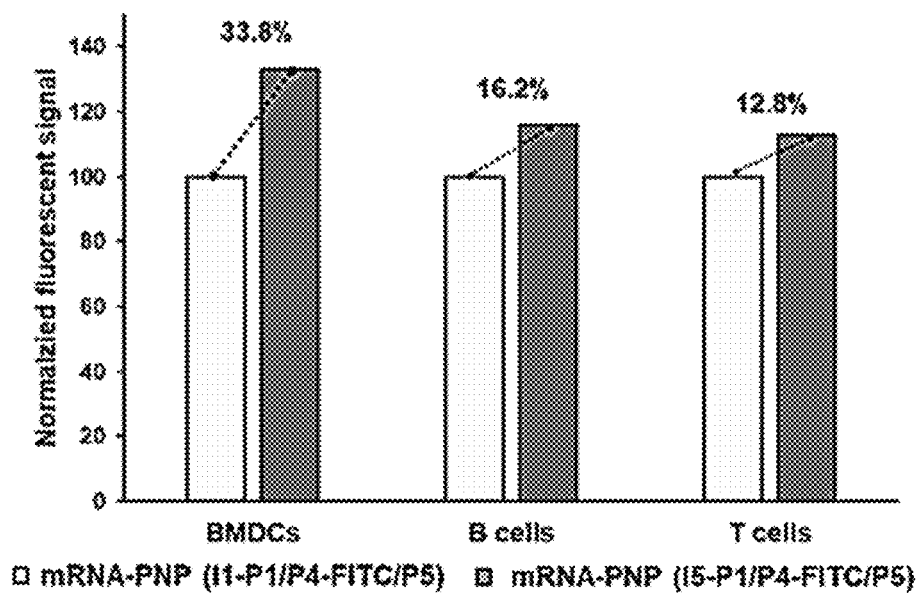
FIG. 6 provides a graphic representation showing the cellular uptake fluorescence signal of BMDC, B cells, and T cells treated with spike mRNA-PNP (I1-P1/P4-FITC/P5) or spike mRNA-PNP (I5-P1/P4-FITC/P5) targeting DC-SIGN after one h. The data was collected using flow cytometry analysis.

As shown in FIG. 6, the I5 polymersome with the aryl mannose head (I5-P1/P4-FITC/P5) exhibited ~34% higher (33.8% increase) cellular uptake by BMDCs compared to the I1 polymersome (I1-P1/P4-FITC/P5) without the glycan head. On the other hand, B cells and T cells with insignificant DC-SIGN expression showed only a slight increase (16.2% increase and 12.8% increase, respectively) in fluorescence signal when treated with polymersomes. This data proved that efficient internalization and selective uptake of mRNA-PNP (I5-P1/P4-FITC/P5) by dendritic cells can be achieved through DC-SIGN receptor targeting.

Evaluation of DC-SIGN binding to the mRNA-polymersomes generated from I5-P/P5, I6-P1/P5, I7-P/P5, I8-P/P5, I9-P1/P5, and I10-P1/P5 under different pH values showed that those polymersomes were able to bind to DC-SIGN with low $K_D$ (Table 1). The mRNA-polymersomes from I5-P1/P5, I8-P1/P5, I9-P1/P5, and I10-P1/P5 bind to the DC-SIGN extracellular domain (ECD) at pH 7.4 and 5.0 with nearly the same affinity. In comparison, the binding of the mRNA-polymersomes from I6-P1/P5 and I7-P1/P5 at lower pH was not detected, implying the coordination to calcium ions decreases at low pH values.

TABLE 1

| Glycan | va-lency | Aryl | linkage | Spacer | $K_{D, app}$ (nM)(pH 7.4) | $K_{D, app}$ (nM)(pH 5) |
|---|---|---|---|---|---|---|
| I5 | 1 | + | | − | 448.1 ± 11.3 | 570.1 ± 21.2 |
| I6 | 1 | − | | − | 6416 ± 282 | n.d. |
| I7 | 1 | − | | + | 2395 ± 49 | n.d. |
| I8 | 1 | + | | + | 278.8 ± 17.3 | 300.1 ± 25.9 |
| I9 | 3 | + | a3, a6 | + | 3.6 ± 1.1 | 3.8 ± 1.4 |
| I10 | 3 | + | a2, a2 | + | 20.9 ± 4.6 | 24.2 ± 4.8 |

Without wishing to be bound by theories, these binding results indicate that aryl trimannoside interacts with DC-SIGN in the acidic endosomal compartments. Such binding stability would enhance DC-SIGN-mediated signaling and its synergism with that of endosomal-resident Toll-like receptors such as TLR7. The strong binding of PNP with aryl-mannoside to DC-SIGN may be due to the dense display of the ligand, and the aryl group may engage in the CH-π and hydrophobic interactions. In addition, for receptor-targeting delivery, ligands are commonly linked with a carrier, and the distance between the carrier and ligand is regulated by the presence of a spacer. The mRNA-PNP carrying the longer length ligand (I8-P1/P5 with Man-Ar-PEG12 and I7-P1/P5 with Man-PEG12) showed slightly higher affinity toward DC-SIGN. Overall, the mRNA-PNP with aryl-trimannoside (I9-P1/P5) exhibited the highest affinity and lowest KD to DC-SIGN. The increased affinity may be due to a clustering effect and the spatial arrangement of the ligand in the polymer, and the aryl moiety may facilitate its hydrophobic interaction.

Figure 7:
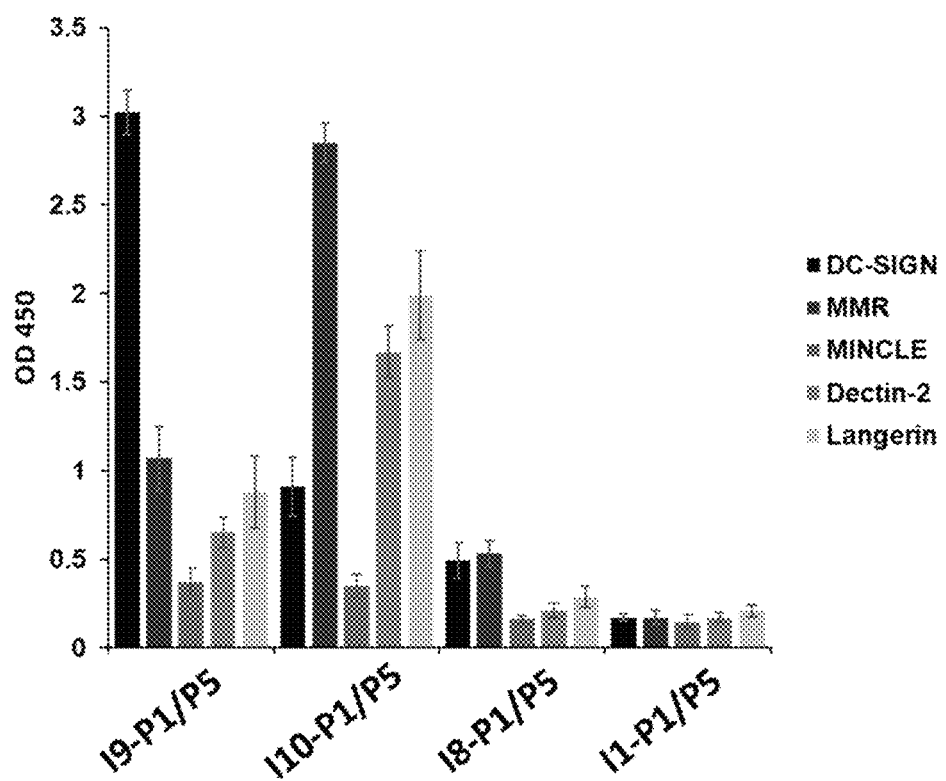
FIG. 7 provides a graphic representation showing a binding analysis of DC-SIGN, MMR, MINCLE, Dectin-2, and Langerin (0.625 g/mL) at pH 7.4 to the polymersomes according to some embodiments of the present disclosure.

Further binding affinity to DC-SIGN, macrophage mannose receptor (MMR), MINCLE, Dectin-2, and langerin was conducted to investigate whether the uptake of mannosylated mRNA-PNPs is dependent on DC-SIGN. As shown in FIG. 7, compared with I1, I8, I9, and I10 polymersomes all showed selective binding. Among them, the branched type of aryl-trimannoside I9 showed a better preference for DC-SIGN compared to the linear type of aryl-trimannoside I10. The fact that I9 presented a more selective binding toward DC-SIGN supported the fact that the efficient uptake of mRNA-I9-P1/P5 by DCs is more likely mediated by DC-SIGN.

Example 4: Immunization Using the Polymersomes of the Present Disclosure

We next evaluated the effect of WT spike mRNA-PNP with or without the aryl mannoside head on vaccination and immune responses.

Methods and Immunization Design.

Animals.

Balb/c mice (8 weeks) were purchased from the National Laboratory Animal Center, Taiwan. All the mice were maintained in a specific pathogen-free environment. Eight-week-old Balb/c mice were immunized i.m. twice at 2-week intervals. Each vaccination contains PBS (100 l). Sera collected from immunized mice were subjected to ELISA analysis 10 days after the last immunization. The experimental protocol was approved by Academia Sinica's Institutional Animal Care and Utilization Committee (approval no. 22-08-1901).

Animal Immunizations.

Figure 8A:
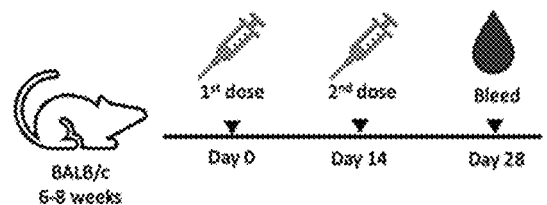
FIG. 8A shows a schematic illustrating the designs of the animal immunization experiments.

BALB/c mice aged 6 to 8 wk old (n=5) were immunized intramuscularly with 15 g of mRNA-PNP in phosphate-buffered saline (PBS). Animals were immunized at week 0 and boosted with a second vaccination at week 2 (FIG. 8A), and serum samples were collected from each mouse 1 week after the second immunization. As a positive control, a group treated with spike mRNA-LNP (including ALC-0315, DSPC, ALC-0159, and cholesterol commonly used in current mRNA vaccine formulation) was included.

Measurement of Serum IgG Titer.

ELISA was used to determine the IgG titer of the mouse serum. The wells of a 96-well ELISA plate (Greiner Bio-One) were coated with 100 ng SARS-CoV-2 spike protein (ACROBiosystems) in 100 mM sodium bicarbonate pH 8.8 at 4° C. overnight. The wells were blocked with 200 μl 5% skim milk in 1×PBS at 37° C. for 1 hour and washed with 200 μl PBST (1×PBS, 0.05% Tween 20, pH 7.4) three times. Mice serum samples with 2-fold serial dilution were added into wells for incubation at 37° C. for 2 hours and washed with 200 μl PBST six times. The wells were incubated with 100 μl HRP conjugated anti-mouse secondary antibody (1:10000, in PBS) at 37° C. for 1 hour and washed with 200 μl PBST six times. 100 l horseradish peroxidase substrate (1-Step™ Ultra TMB-ELISA Substrate Solution) (Thermo Scientific™) was added into wells, followed by 100 μl 1M $H_2SO_4$. After incubation for 30 minutes, absorbance (OD 450 nm) was measured using SpectraMax M5.

Pseudovirus Neutralization Assay.

Pseudovirus was constructed by the RNAi Core Facility at Academia Sinica using a procedure similar to that described previously. Briefly, the pseudotyped lentivirus carrying SARS-CoV-2 spike protein was generated by transiently transfecting HEK-293T cells with pCMV-ΔR8.91, pLAS2w.Fluc.Ppuro. HEK-293T cells were seeded one day before transfection, and indicated plasmids were delivered into cells using TransITR-LT1 transfection reagent (Mirus). The culture medium was refreshed at 16 hours and harvested at 48 hours and 72 hours post-transfection. Cell debris was removed by centrifugation at 4,000×g for 10 min, and the supernatant was passed through a 0.45-μm syringe filter (Pall Corporation). The pseudotyped lentivirus was aliquot and then stored at −80° C. To estimate the lentiviral titer by AlarmaBlue assay (Thermo Scientific), The transduction unit (TU) of SARS-CoV-2 pseudotyped lentivirus was estimated by using cell viability assay in responded to the limited dilution of lentivirus. In brief, HEK-293T cells stably expressing the human ACE2 gene were plated on a 96-well plate one day before lentivirus transduction. For the titering pseudotyped lentivirus, different amounts of lentivirus were added into the culture medium containing polybrene (final concentration 8 g/ml). Spin infection was carried out at 1,100×g in a 96-well plate for 30 minutes at 37° C. After incubating cells at 37° C. for 16 hr, the culture medium containing virus and polybrene was removed and replaced with fresh complete DMEM containing 2.5 g/ml puromycin. After treating puromycin for 48 hrs, the culture media was removed, and the cell viability was detected using 10% AlamarBlue reagents according to the manufacturer's instructions. The survival rate of uninfected cells (without puromycin treatment) was set as 100%. The virus titer (transduction units) was determined by plotting the survival cells versus the diluted viral dose. For neutralization assay, heat-inactivated sera or antibodies were serially diluted and incubated with 1,000 TU of SARS-CoV-2 pseudotyped lentivirus in DMEM for 1 h at 37° C. The mixture was then inoculated with 10,000 HEK-293T cells stably expressing the human ACE2 gene in a 96-well plate. The culture medium was replaced with fresh complete DMEM (supplemented with 10% FBS and 100 U/mL penicillin/streptomycin) at 16 h postinfection and continuously cultured for another 48 h. The expression level of the luciferase gene was determined by using the Bright-Glo Luciferase Assay System (Promega). The relative light unit (RLU) was detected by Tecan i-control (Infinite 500). The percentage of inhibition was calculated as the ratio of RLU reduction in the presence of diluted serum to the RLU value of no serum control using the formula ($RLU^{control}-RLU^{Serum}$)/RLU control.

Results

Figure 8B:
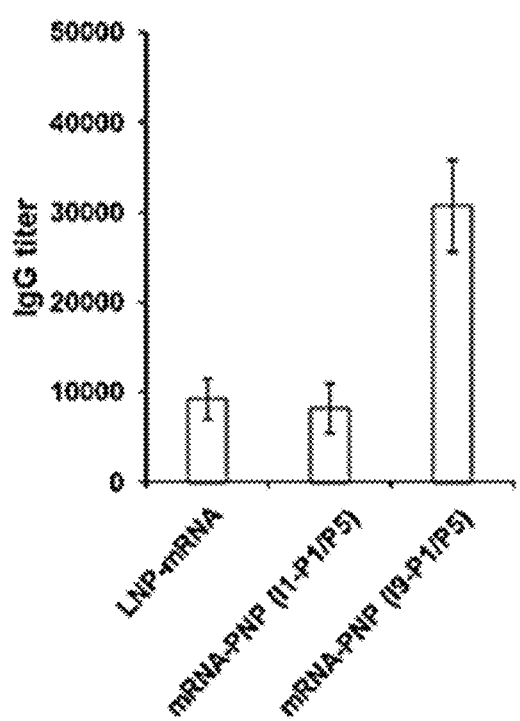
FIG. 8B provides a graphic representation showing the serum spike-specific IgG titer induced by immunization of I1-P1/P5 mRNA-PNP, 19-P1/P5 mRNA-PNP, and LNP-mRNA (control) measured at Day 28 after the immunization.
Figure 8C:
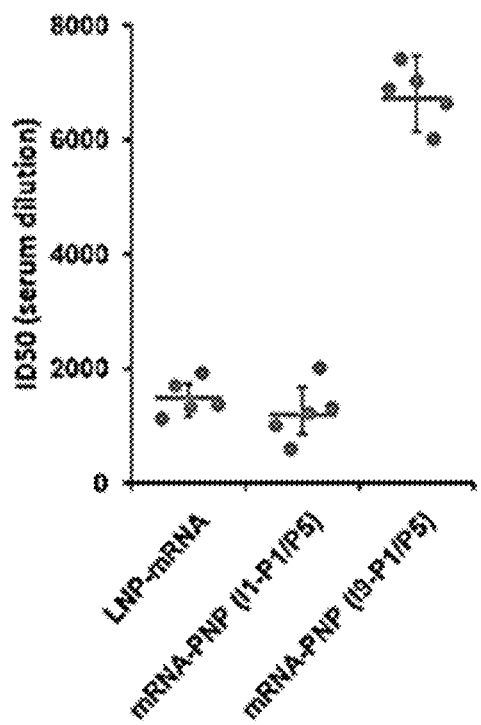
FIG. 8C provides a graphic representation showing the neutralization titer (ID50) by immunization of I1-P1/P5 mRNA-PNP, I9-P1/P5 mRNA-PNP, and LNP-mRNA (control) measured on Day 28 after the immunization. The neutralization titer was calculated as the reciprocal of the serum dilution that resulted in a 50% reduction in RLUs compared to virus control wells after subtracting background RLU. The ID50 values are labeled on the plots with the standard error of the mean.

The results showed that the I1-P1/P5 polymersomes treatment and the mRNA-LNP treatment both can generate ten thousand levels of anti-spike antibodies in the serum on day 28. In contrast, the I9-P1/P5 polymersomes treatment was able to generate about thirty thousand levels of the anti-spike antibodies, which was at least 3-fold higher (FIG. 8B). The serum was then tested for the ability to neutralize pseudovirus-mediated entry to the ACE2-expressing cells. The level of antisera from I1-P1/P5 polymersomes was similar to the mRNA-LNP group; both were below 2000. In comparison, a significantly higher level (over 6000) of neutralizing antibodies in the I9-P1/P5 polymersomes group was observed (FIG. 8C), and the spike-specific antibody titer and pseudovirus neutralization activity were well correlated.

Exemplary Embodiments

Embodiment 1. A copolymer for forming a polymersome, wherein the copolymer comprises: an initiator block, comprising a glycan head; a propagator block, comprising a functional moiety, which comprises a guanidine group, a zwitterion group, a diethylene triamine, or a combination thereof; and a linkage, covalently connecting the initiator block and the propagator block, wherein the linkage comprises a disulfide bond.

Embodiment 2. The copolymer of embodiment 1, wherein the glycan head comprises a terminal mannoside.

Embodiment 3. The copolymer of embodiment 1 or embodiment 2, wherein the glycan head comprises an O-aryl mannoside comprising an optionally substituted benzene ring.

Embodiment 4. The copolymer of any one of embodiments 1 to 3, wherein the glycan head comprises a mono-mannoside, a di-mannoside, or a tri-mannoside.

Embodiment 5. The copolymer of embodiment 4, wherein the tri-mannoside is a linear or branched tri-mannoside.

Embodiment 6. The copolymer of embodiment 5, wherein the branched tri-mannoside is a α-1,3-α-1,6-trimannoside.

Embodiment 7. The copolymer of any one of embodiments 1 to 6, wherein the initiator block further comprises an initiator spacer.

Embodiment 8. The copolymer of embodiment 7, wherein the initiator spacer comprises a saturated carbon moiety, a polyethylene glycol (PEG) moiety, or a combination thereof.

Embodiment 9. The copolymer of embodiment 8, wherein the saturated carbon moiety comprises at least 2, 3, 4, 5, 6, 7, 8, 9, 10, 11, 12, 13, 14, or 15 carbons (optionally, 2 to 6 carbons).

Embodiment 10. The copolymer of embodiment 8 or embodiment 9, wherein the PEG moiety comprises 2 to 72 ($OCH_2CH_2$) subunits.

Embodiment 11. The copolymer of embodiment 10, wherein the PEG moiety is of a linear, branched, or star configuration.

Embodiment 12. The copolymer of any one of embodiments 1 to 11, wherein the glycan head is configured to bind a dendritic cell.

Embodiment 13. The copolymer of embodiment 12, wherein the glycan head is configured to selectively bind DC-SIGN.

Embodiment 14. The copolymer of embodiment 13, wherein the glycan head is configured to bind DC-SIGN at a $K_D$ ranging from 5 to 8000 nM at pH 7.4.

Embodiment 15. The copolymer of embodiment 14, wherein the $K_D$ ranges from 5 to 500 nM at pH 7.4.

Embodiment 16. The copolymer of any one of embodiments 13 to 15, wherein the glycan head is configured to bind DC-SIGN at a $K_D$ ranging from 1 to 2000 nM at pH 5.

Embodiment 17. The copolymer of embodiment 16, wherein the $K_D$ ranges from 1 to 600 nM at pH 5.

Embodiment 18. The copolymer of embodiment 1, wherein the glycan head comprises a $9^{BPC}$Neu5Ac conjugated N-glycan, Neu5Ac conjugated N-glycan, $9^{TCC}$Neu5Ac conjugated N-glycan, or a combination thereof.

Embodiment 19. The copolymer of embodiment 18, wherein the initiator block is configured to bind Siglec-2, Siglec-5/E, Siglec-1, or a combination thereof.
Embodiment 20. The copolymer of any one of embodiments 1 to 19, wherein the initiator block is selected from a group consisting of:
IB2
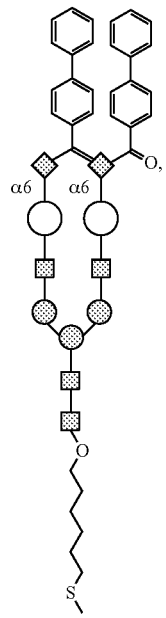
IB3
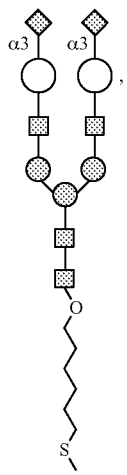
IB4
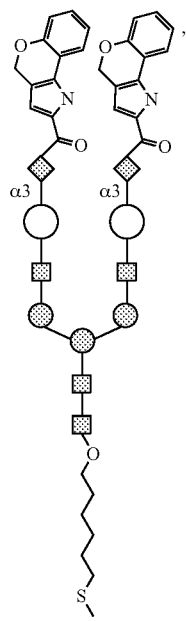
IB5
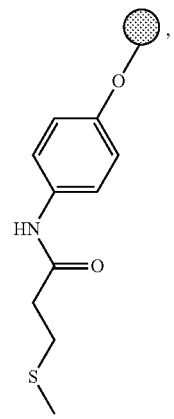
IB6
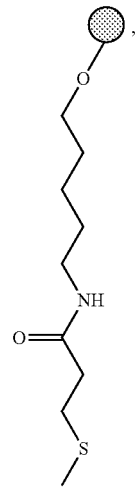

-continued

IB7
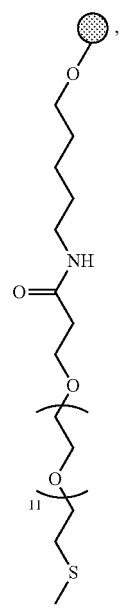

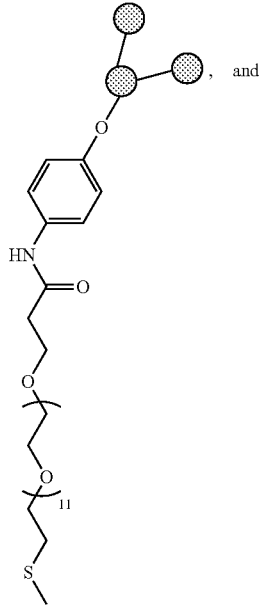

IB9

, and

IB8
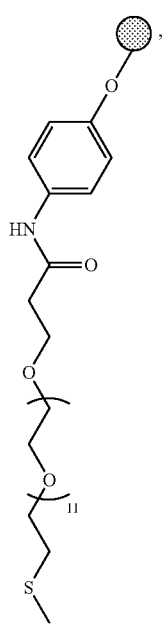

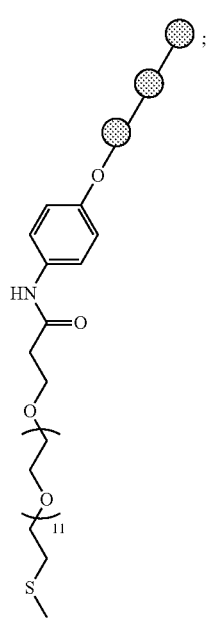

IB10
;

wherein the solid circle represents mannoside, the open circle represents Galactose, the solid square represents GlcNAc, and the diamond represents Neu5Ac.

Embodiment 21. The copolymer of any one of embodiments 1 to 20, wherein the propagator block comprises more than one guanidine group.

Embodiment 22. The copolymer of embodiment 21, wherein the propagator block comprises three guanidine groups.

Embodiment 23. The copolymer of any one of embodiments 1 to 22, wherein the propagator block comprises a propagator spacer, comprising a saturated carbon moiety, a polyethylene glycol (PEG) moiety, or a combination thereof.

Embodiment 24. The copolymer of embodiment 23, wherein the saturated carbon moiety comprises at least 2, 3, 4, 5, 6, 7, 8, 9, 10, 11, 12, 13, 14, or 15 carbons (optionally, 2 to 6 carbons).

Embodiment 25. The copolymer of embodiment 23 or embodiment 24, wherein the PEG moiety comprises 2 to 72 (OCH$_2$CH$_2$) subunits.

Embodiment 26. The copolymer of embodiment 25, wherein the PEG moiety is of a linear, branched, or star configuration.

Embodiment 27. The copolymer of any one of embodiments 1 to 26, comprising a plurality of the propagator blocks and a plurality of the linkages, and each propagator block of the plurality of the propagator blocks connects to at least another propagator block of the propagator blocks or the initiator block via one of the plurality of the linkages.

Embodiment 28. The copolymer of any one of embodiments 1 to 27, wherein the propagator block is a first propagator block, the linkage is a first linkage, and the copolymer further comprises a second propagator block, connecting to the first propagator block via a second linkage; wherein the first propagator block and the second propagator block independently comprise a guanidine group, a zwitterion group, a diethylene triamine, or a combination thereof; and wherein the second linkage comprises a disulfide bond.

Embodiment 29. The copolymer of embodiment 28, wherein the first propagator block comprises the guanidine group, and the second propagator block comprises the zwitterion group.

Embodiment 30. The copolymer of embodiment 28, wherein the first propagator block comprises the guanidine group, and the second propagator block comprises the diethylene triamine.

Embodiment 31. The copolymer of any one of embodiments 28 to 30, wherein the copolymer further comprises a third propagator block, wherein the third propagator block is linked to the first propagator block or the second propagator block via a third linkage comprising a disulfide bond.

Embodiment 32. The copolymer of any one of embodiments 1 to 31, wherein the propagator block is selected from a group consisting of:

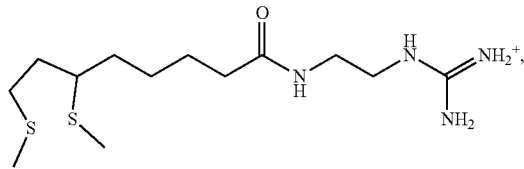

PB1

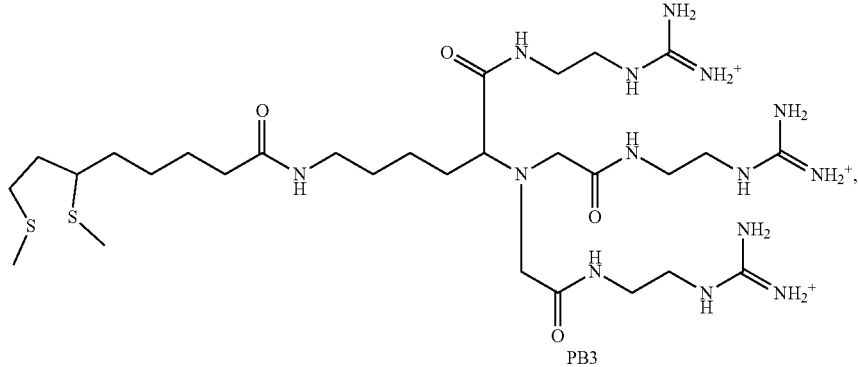

PB2

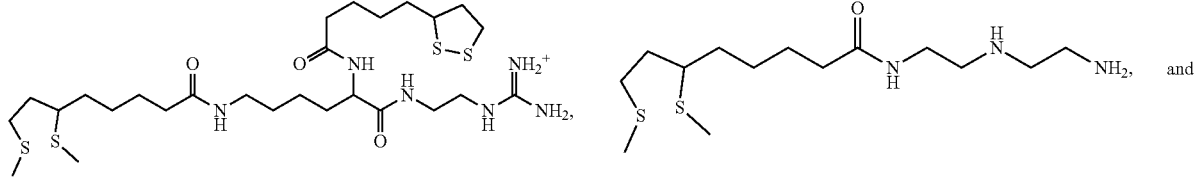

PB3            PB4

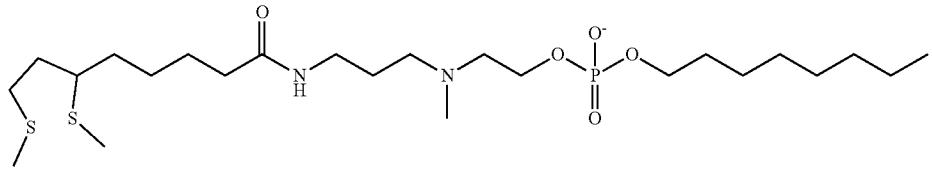

PB5

Embodiment 33. The copolymer of embodiment 32, comprising at least two propagator blocks, wherein the at least two propagator blocks are (1) PB1 and PB5, (2) PB1 and PB4, (3) PB2 and PB5, (4) PB2 and PB5, or (5) P1, P4, and P5.

Embodiment 34. The copolymer of embodiment 33, wherein the initiator block and the at least two propagator block are selected from a group consisting of IB5-PB1/PB5, IB5-PB1/PB4, IB5-PB2/PB5, IB5-PB2/PB4, IB5-PB1/PB4/PB5, IB6-PB1/PB5, IB6-PB1/PB4, IB6-PB2/PB5, IB6-PB2/PB4, IB6-PB1/PB4/PB5, IB7-

PB1/PB5, IB7-PB1/PB4, IB7-PB2/PB5, IB7-PB2/PB4, IB7-PB1/PB4/PB5, IB8-PB1/PB5, IB8-PB1/PB4, IB8-PB2/PB5, IB8-PB2/PB4, IB8-PB1/PB4/PB5, IB9-PB1/PB5, IB9-PB1/PB4, IB9-PB2/PB5, IB9-PB2/PB4, IB9-PB1/PB4/PB5, IB10-PB1/PB5, IB10-PB1/PB4, IB10-PB2/PB5, IB10-PB2/PB4, and IB10-PB1/PB4/PB5.

Embodiment 35. A polymersome, comprising a membrane defining an inner space, wherein the membrane comprises the copolymer of any one of embodiments 1 to 34.

Embodiment 36. The polymersome of embodiment 35, wherein the copolymer comprises at least 50%, 70%, 80%, 90%, 95%, or 99% of the membrane.

Embodiment 37. The polymersome of embodiment 35 or embodiment 36, wherein the membrane encapsulates a payload therewithin.

Embodiment 38 The polymersome of embodiment 37, wherein the payload is a nucleic acid, a compound, a polypeptide, a protein, a glycan, or a combination thereof.

Embodiment 39. The polymersome of embodiment 38, wherein the nucleic acid is RNA or DNA.

Embodiment 40. The polymersome of embodiment 39, wherein the payload encodes a polypeptide.

Embodiment 41. The polymersome of any one of embodiments 37 to 40, wherein the payload is immunogenic, or the payload is a nucleic acid configured to encode an immunogenic polypeptide or protein.

Embodiment 42. The polymersome of any one of embodiments 35 to 41, wherein the copolymer is a first copolymer, and the membrane further comprises a second copolymer, wherein the first copolymer and the second copolymer are independent of any one of embodiments 1 to 34.

Embodiment 43. The polymersome of any one of embodiments 35 to 42, having a diameter of 0.001 to 5 microns or 0.01 to 5 microns.

Embodiment 44. The polymersome of any one of embodiments 35 to 43, wherein the payload is a first payload, and the membrane further encapsulates a second payload.

Embodiment 45. The polymersome of embodiment 44, wherein the second payload is a nucleic acid, a compound, a polypeptide, a protein, a glycan, or a combination thereof.

Embodiment 46. The polymersome of embodiment 45, wherein the first payload and the second payload are different.

Embodiment 47. A formulation, comprising a polymersome of any one of embodiments 35 to 46.

Embodiment 48. The formulation of embodiment 47, comprising 0.01 to 95% (w/w) of the polymersome.

Embodiment 49. The formulation of embodiment 47 or embodiment 48, wherein the polymersome is a first polymersome, and the composition further comprises a second polymersome.

Embodiment 50. The formulation of embodiment 49, wherein the first polymersome and the second polymersome are different in size, copolymers forming the membrane thereof, payload encapsulated within the polymersomes, or a combination thereof.

Embodiment 51. The formulation of any one of embodiments 47 to 50, further comprising a pharmaceutically acceptable excipient, adjuvant, or a combination thereof.

Embodiment 52. The formulation of claim 51, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

Embodiment 53. The formulation of embodiment 51 or embodiment 52, wherein the adjuvant comprises C34, Gluco-C34, 7DW8-5, C17, C23, C30, α-galactosylceramide, Aluminum salt, Squalene, MF59, or QS-21. Other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03, MF59, and CpG 1018, or a combination thereof.

Embodiment 54. A kit for preparing a polymersome, comprising: a first reagent, comprising an initiator, wherein the initiator comprises a glycan head and an initiator linking moiety, and a second reagent, comprising a propagator, wherein the propagator comprises a functional moiety and a propagator linking moiety, wherein the functional moiety comprises a guanidine group, a zwitterion group, a diethylene triamine, or a combination thereof; and wherein the initiator linking moiety is configured to couple with the propagator linking moiety via a linkage comprising a disulfide bond.

Embodiment 55. The kit of embodiment 54, wherein the glycan head comprises a terminal mannoside.

Embodiment 56. The kit of embodiment 54 or embodiment 55, wherein the glycan head comprises an O-aryl mannoside.

Embodiment 57. The kit of any one of embodiments 54 to 56, wherein the glycan head comprises a mono-mannoside, a di-mannoside, or a tri-mannoside.

Embodiment 58. The kit of embodiment 57, wherein the tri-mannoside is a linear or branched tri-mannoside.

Embodiment 59. The kit of embodiment 58, wherein the branched tri-mannoside is a α-1,3-α-1,6-trimannoside.

Embodiment 60. The kit of any one of embodiments 54 to 59, wherein the initiator further comprises an initiator spacer, comprising a saturated carbon moiety, a polyethylene glycol (PEG) moiety, or a combination thereof.

Embodiment 61. The kit of embodiment 60, wherein the saturated carbon moiety comprises at least 2, 3, 4, 5, 6, 7, 8, 9, 10, 11, 12, 13, 14, or 15 carbons (optionally, 2 to 6 carbons).

Embodiment 62. The kit of embodiment 61, wherein the PEG moiety comprises 2 to 72 ($OCH_2CH_2$) subunits.

Embodiment 63. The kit of embodiment 62, wherein the PEG moiety is of a linear, branched, or star configuration.

Embodiment 64. The kit of any one of embodiments 54 to 63, wherein the glycan head is configured to bind a dendritic cell.

Embodiment 65. The kit of embodiment 64, wherein the glycan head is configured to selectively bind DC-SIGN.

Embodiment 66. The kit of embodiment 65, wherein the glycan head is configured to bind DC-SIGN at a $K_D$ ranging from 5 to 8000 nM at pH 7.4.

Embodiment 67. The kit of embodiment 66, wherein the $K_D$ ranges from 5 to 500 nM at pH 7.4.

Embodiment 68. The kit of any one of embodiments 65 to 67, wherein the glycan head is configured to bind DC-SIGN at a $K_D$ ranging from 1 to 800 nM at pH 5.

Embodiment 69. The kit of embodiment 68, wherein the $K_D$ ranges from 1 to 600 nM at pH 5.

Embodiment 70. The kit of any one of embodiments 54 to 69, wherein the glycan head comprises a $9^{BPC}$Neu5Ac conjugated N-glycan (I2), Neu5Ac conjugated N-glycan (I3), $9^{TCC}$Neu5Ac conjugated N-glycan (I4), or a combination thereof.

Embodiment 71. The kit of embodiment 70, wherein the glycan head is configured to bind Siglec-2, Siglec-5/E, Siglec-1, or a combination thereof.

Embodiment 72. The kit of any one of embodiments 54 to 71, wherein the initiator linking moiety is a thiol group or a dithiolane group.

Embodiment 73. The kit of any one of embodiments 54 to 72, wherein the initiator is selected from a group consisting of:

I2

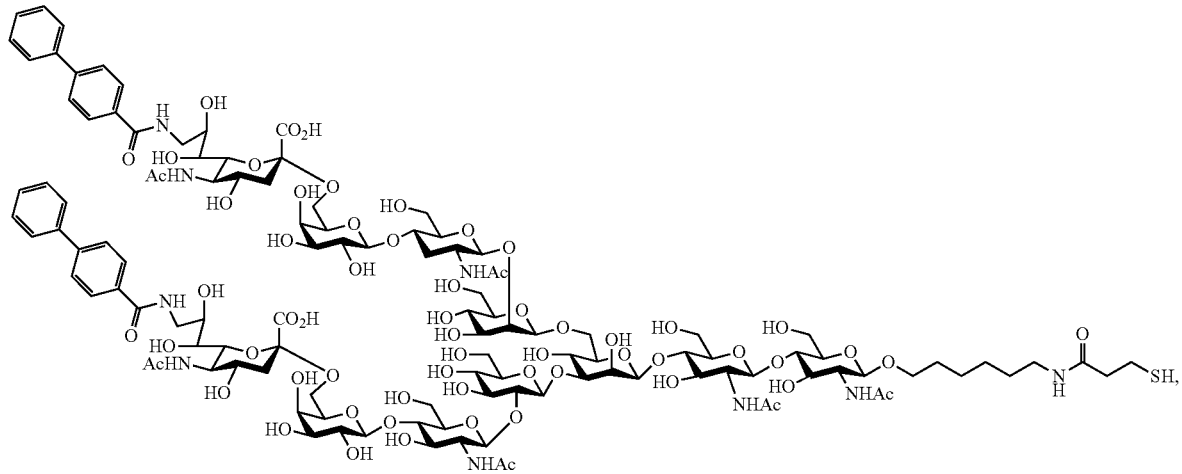

I3

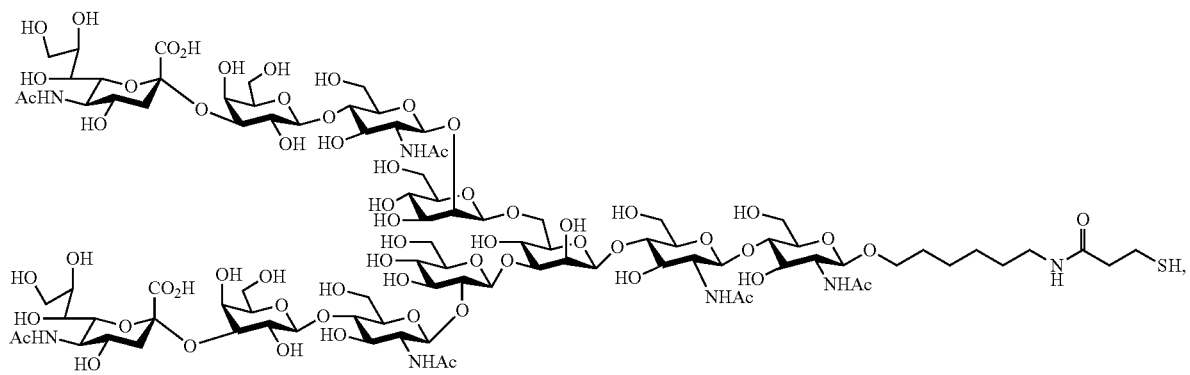

I4

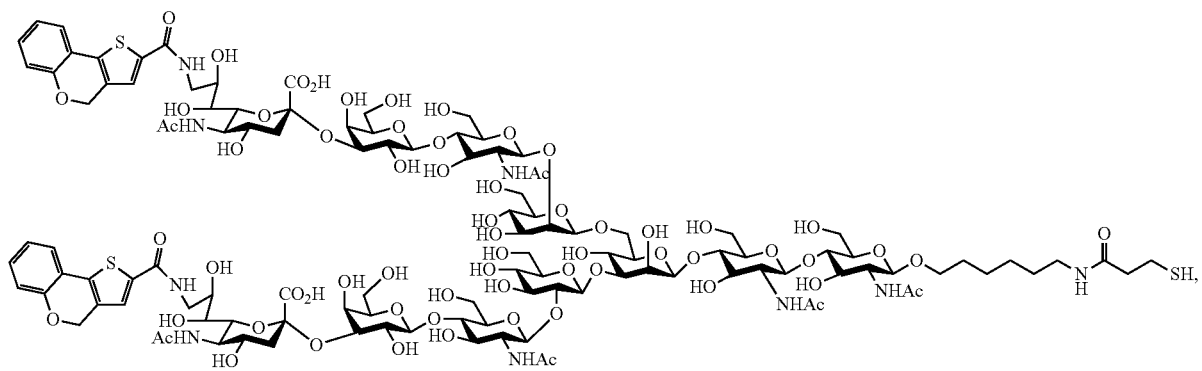

-continued
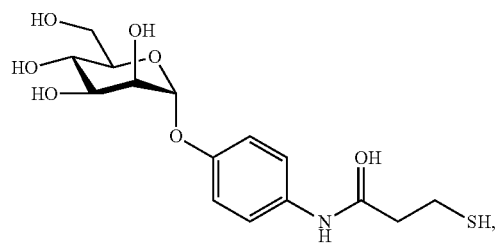
I5
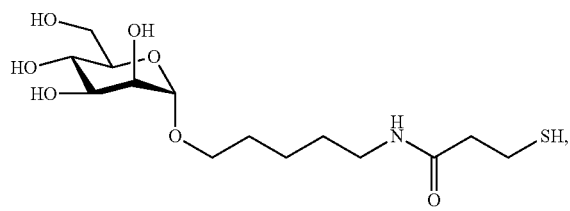
I6
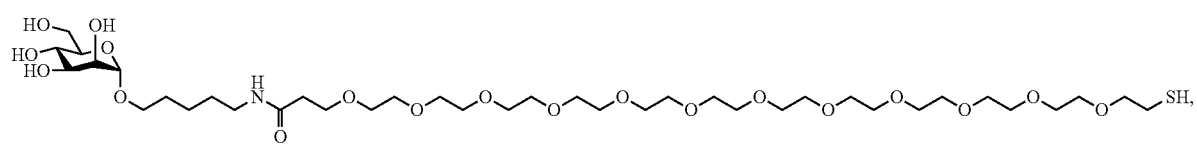
I7
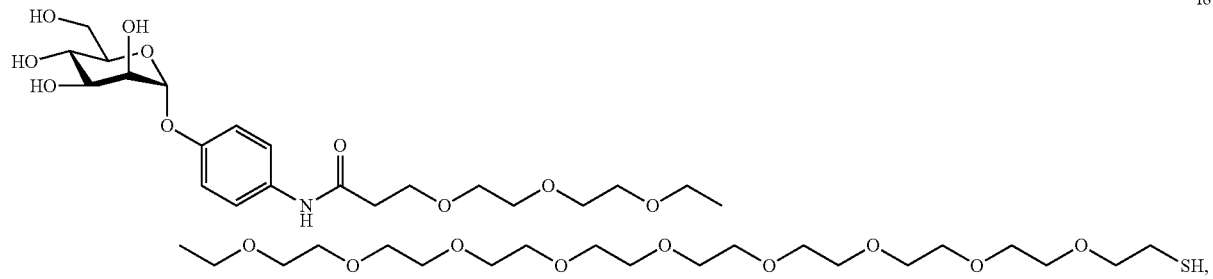
I8
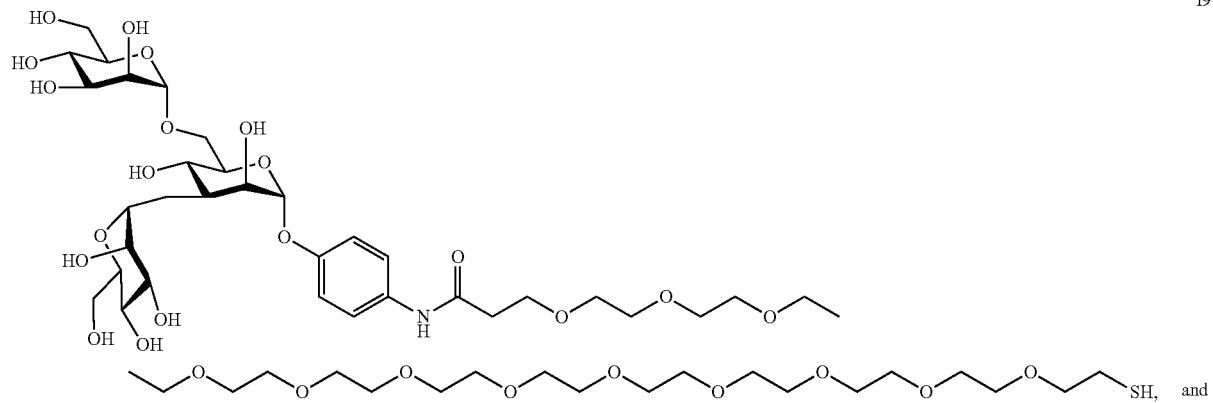
I9
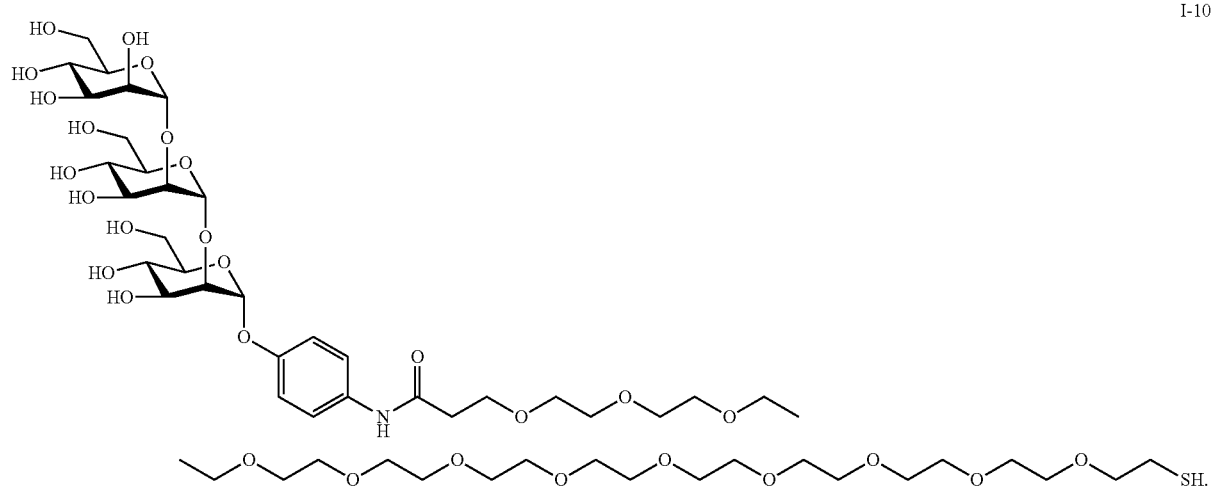
I-10

Embodiment 74. The kit of any one of embodiments 54 to 73, wherein the propagator comprises more than one guanidine group.

Embodiment 75. The kit of embodiment 74, wherein the propagator comprises three guanidine groups.

Embodiment 76. The kit of any one of embodiments 54 to 75, wherein the propagator further comprises a propagator spacer, comprising a saturated carbon moiety, a polyethylene glycol (PEG) moiety, or a combination thereof.

Embodiment 77. The kit of embodiment 76, wherein the saturated carbon moiety comprises at least 2, 3, 4, 5, 6, 7, 8, 9, 10, 11, 12, 13, 14, or 15 carbons (optionally, 2 to 6 carbons).

Embodiment 78. The kit of embodiment 76 or embodiment 77, wherein the PEG moiety comprises 2 to 72 ($OCH_2CH_2$) subunits.

Embodiment 79. The kit of embodiment 78, wherein the PEG moiety is a linear PEG.

Embodiment 80. The kit of any one of embodiments 54 to 79, wherein the propagator of the second reagent is a first propagator, and wherein the second reagent further comprises a second propagator, or the kit further comprises a third reagent comprising the second propagator; and wherein the first propagator and the second propagator independently comprise a functional moiety comprising a guanidine group, a zwitterion group, a diethylene triamine, or a combination thereof.

Embodiment 81. The kit of embodiment 80, wherein the first propagator comprises the guanidine group, and the second propagator comprises the zwitterion group.

Embodiment 82. The kit of embodiment 80, wherein the first propagator comprises the guanidine group, and the second propagator comprises the diethylene triamine.

Embodiment 83. The kit of any one of embodiments 54 to 82, wherein the propagator linking moiety is a thiol group or a dithiolane group.

Embodiment 84. The kit of any one of embodiments 54 to 83, wherein the propagator is selected from a group consisting of:

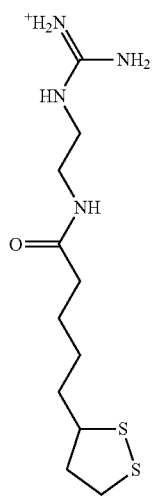

P1

-continued

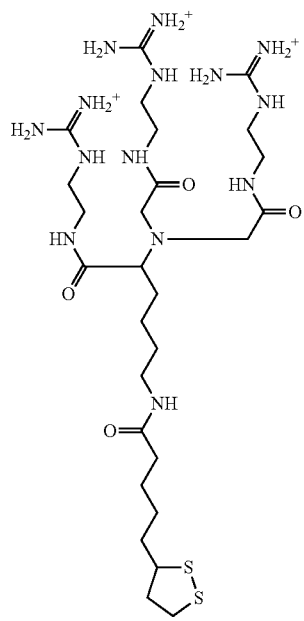

P2

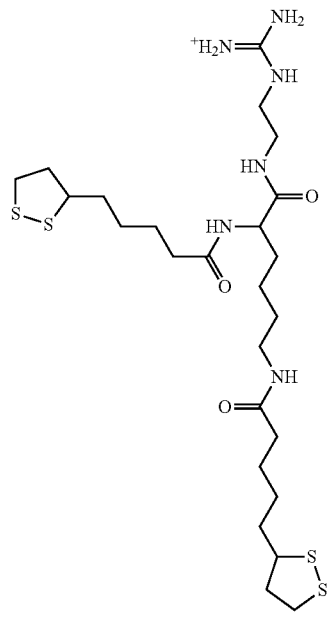

P3

-continued

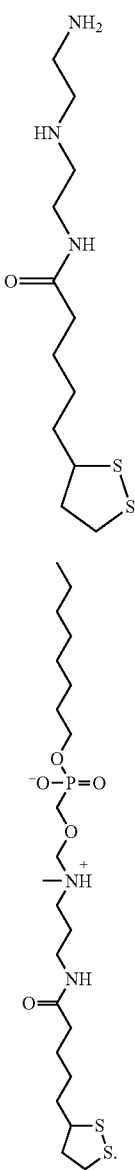

Embodiment 85. The kit of any one of embodiments 54 to 84, wherein the first reagent and the second reagent are contained in the same container.

Embodiment 86. The kit of any one of embodiments 54 to 84, wherein the first reagent and the second reagent are contained in separate containers.

Embodiment 87. The kit of any one of embodiments 54 to 86, further comprising a payload, wherein the payload is a nucleic acid, a compound, a polypeptide, a protein, a glycan, or a combination thereof.

Embodiment 88. The kit of embodiment 87, wherein the nucleic acid is RNA or DNA.

Embodiment 89. The kit of embodiment 88, wherein the payload encodes a polypeptide.

Embodiment 90. The kit of any one of embodiments 87 to 89, wherein the payload is immunogenic, or the payload is a nucleic acid configured to encode an immunogenic polypeptide or protein.

Embodiment 91. A method of targeted delivering a payload in a subject, comprising administering to the subject an effective amount of a pharmaceutical formulation comprising a polymersome, wherein the polymersome comprises a membrane encapsulating the payload, and wherein the membrane comprises a copolymer of any one of embodiments 1 to 34.

Embodiment 92. The method of embodiment 91, wherein the copolymer comprises at least 50%, 70%, 80%, 90%, 95%, or 99% of the membrane.

Embodiment 93. The method of embodiment 92, wherein the copolymer is a first copolymer, and the membrane further comprises a second copolymer, wherein the first copolymer and the second copolymer are independently of any one of embodiments 1 to 34.

Embodiment 94. The method of any one of embodiments 91 to 93, wherein the payload is a nucleic acid, a compound, a peptide, a protein, a glycan, or a combination thereof.

Embodiment 95. The method of embodiment 94, wherein the nucleic acid is RNA or DNA.

Embodiment 96. The method of embodiment 95, wherein the payload encodes a polypeptide.

Embodiment 97. The method of any one of embodiments 91 to 96, wherein the payload is immunogenic, or the payload is a nucleic acid configured to encode an immunogenic polypeptide or protein.

Embodiment 98. The method of any one of embodiments 91 to 97, wherein the payload is a first payload, and the membrane further encapsulates a second payload.

Embodiment 99. The method of embodiment 98, wherein the second payload is a nucleic acid, a compound, a polypeptide, a protein, a glycan, or a combination thereof.

Embodiment 100. The method of embodiment 99, wherein the first payload and the second payload are different.

Embodiment 101. A method of preventing or treating a disease in a subject, comprising administering to the subject an effective amount of a pharmaceutical formulation comprising a polymersome, wherein the polymersome comprises a membrane, wherein the membrane comprises the polymeric component of any one of embodiments 1 to 34; and a payload, encapsulated within the membrane; and wherein the payload is a therapeutic agent or derives a therapeutic agent.

Embodiment 102. The method of embodiment 101, wherein the polymeric component comprises at least 50%, 70%, 80%, 90%, 95%, or 99% of the membrane.

Embodiment 103. The method of embodiment 101 or embodiment 102, wherein the payload is a nucleic acid, a compound, a peptide, a protein, a glycan, or a combination thereof.

Embodiment 104. The method of embodiment 103, wherein nucleic acid is RNA or DNA.

Embodiment 105. The method of embodiment 104, wherein the payload encodes a polypeptide.

Embodiment 106. The method of any one of embodiments 101 to 105, wherein the payload is a first payload, and the membrane further encapsulates a second payload.

Embodiment 107. The method of embodiment 106, wherein the second payload is a nucleic acid, a compound, a polypeptide, a protein, a glycan, or a combination thereof.

Embodiment 108. The method of embodiment 107, wherein the first payload and the second payload are different.

Embodiment 109. The method of any one of embodiments 101 to 108, wherein the polymersome is administered in an initial dose and followed by one, two, three, four, five, or more booster doses.

Embodiment 110. The method of embodiment 109, wherein the booster doses are administered about one month, about two months, about three months, about four months, about five months, or about six months or more following the initial dose.

Embodiment 111. The method of any one of embodiments 101 to 110, wherein the effective amount ranges from about 5 g to 1000 g.

Embodiment 112. A method of boosting an adaptive immune response, comprising administering to a subject an effective amount of an effective amount of a pharmaceutical formulation comprising a polymersome; wherein the polymersome comprises a membrane encapsulating the payload, and wherein the membrane comprises a copolymer of any one of embodiments 1 to 34; wherein the payload is immunogenic or derives an immunogenic biomolecule.

Embodiment 113. The method of embodiment 112, wherein the polymeric component comprises at least 50%, 70%, 80%, 90%, 95%, or 99% of the membrane.

Embodiment 114. The method of embodiment 83 or embodiment 84, wherein the payload is a nucleic acid, a compound, a peptide, a protein, a glycan, or a combination thereof.

Embodiment 115. The method of embodiment 85, wherein nucleic acid is RNA or DNA.

Embodiment 116. The method of any one of embodiments 112 to 115, wherein the biomolecule is a polypeptide or a protein.

Embodiment 117. The method of any one of embodiments 112 to 116, wherein the payload is a first payload, and the membrane further encapsulates a second payload.

Embodiment 118. The method of embodiment 117, wherein the second payload is a nucleic acid, a compound, a polypeptide, a protein, a glycan, or a combination thereof.

Embodiment 119. The method of embodiment 118, wherein the first payload and the second payload are different.

Embodiment 120. The method of any one of embodiments 112 to 119, wherein the polymersome is administered in an initial dose followed by one, two, three, four, five, or more booster doses.

Embodiment 121. The method of embodiment 120, wherein the booster doses are administered about one month, about two months, about three months, about four months, about five months, or about six months or more following the initial dose.

Embodiment 122. The method of any one of embodiments 112 to 121, wherein the effective amount ranges from about 5 g to 1000 g.

What is claimed is:

1. A copolymer for forming a polymersome, wherein the copolymer comprises:

an initiator block, comprising a glycan head;
   a propagator block, comprising a functional moiety, which comprises a guanidine group, a zwitterion group, a diethylene triamine, or a combination thereof, and
   a linkage, covalently connecting the initiator block and the propagator block, wherein the linkage comprises a disulfide bond.

2. The copolymer of claim 1, wherein the glycan head comprises a terminal mannoside.

3. The copolymer of claim 1 or claim 2, wherein the glycan head comprises an O-aryl mannoside comprising an optionally substituted benzene ring.

4. The copolymer of claim 1, wherein the glycan head comprises a mono-mannoside, a di-mannoside, or a tri-mannoside.

5. The copolymer of claim 4, wherein the tri-mannoside is a linear or branched tri-mannoside.

6. The copolymer of claim 5, wherein the branched tri-mannoside is a α-1,3-α-1,6-trimannoside.

7. The copolymer of claim 1, wherein the initiator block further comprises an initiator spacer.

8. The copolymer of claim 7, wherein the initiator spacer comprises a saturated carbon moiety, a polyethylene glycol (PEG) moiety, or a combination thereof.

9. The copolymer of claim 8, wherein the saturated carbon moiety comprises at least 2, 3, 4, 5, 6, 7, 8, 9, 10, 11, 12, 13, 14, or 15 carbons (optionally, 2 to 6 carbons).

10. The copolymer of claim 8, wherein the PEG moiety comprises 2 to 72 ($OCH_2CH_2$) subunits.

11. The copolymer of claim 10, wherein the PEG moiety is of a linear, branched, or star configuration.

12. The copolymer of claim 1, wherein the glycan head is configured to bind a dendritic cell.

13. The copolymer of claim 12, wherein the glycan head is configured to selectively bind DC-SIGN.

14. The copolymer of claim 13, wherein the glycan head is configured to bind DC-SIGN at a $K_D$ ranging from 5 to 8000 nM at pH 7.4.

15. The copolymer of claim 14, wherein the $K_D$ ranges from 5 to 500 nM at pH 7.4.

16. The copolymer of claim 13, wherein the glycan head is configured to bind DC-SIGN at a $K_D$ ranging from 1 to 2000 nM at pH 5.

17. The copolymer of claim 16, wherein the $K_D$ ranges from 1 to 600 nM at pH 5.

18. The copolymer of claim 1, wherein the glycan head comprises a $9^{BPC}$Neu5Ac conjugated N-glycan, Neu5Ac conjugated N-glycan, $9^{TCC}$Neu5Ac conjugated N-glycan, or a combination thereof, wherein BPC denotes biphenylcarboxyl, TCC denotes 4H-thieno[3,2-c]chromene-2-carbamoyl), and Neu5Ac denotes N-Acetylneuraminic acid.

19. The copolymer of claim 18, wherein the initiator block is configured to bind Siglec-2, Siglec-5/E, Siglec-1, or a combination thereof.

20. The copolymer of claim 1, wherein the initiator block is selected from a group consisting of:

111
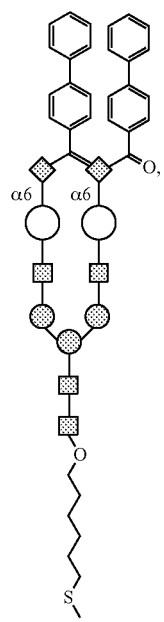
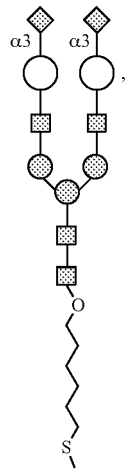
112
-continued
IB2
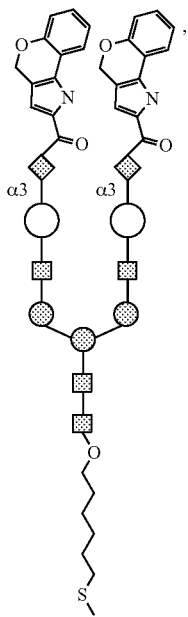
IB4
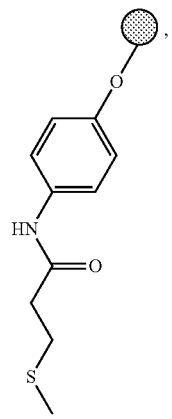
IB5
IB3
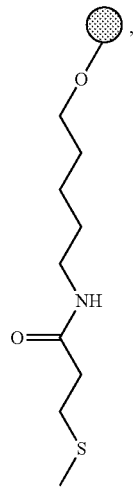
IB6

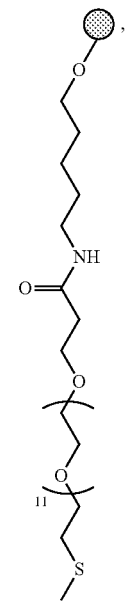

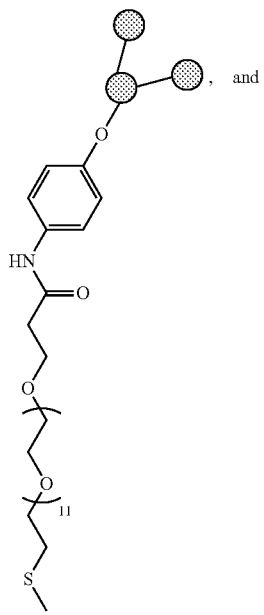

wherein the solid circle represents mannoside, the open circle represents Galactose, the solid square represents GlcNAc, and the diamond represents Neu5Ac.

21. The copolymer of claim 1, wherein the propagator block comprises more than one guanidine group.

22. The copolymer of claim 21, wherein the propagator block comprises three guanidine groups.

23. The copolymer of claim 1, wherein the propagator block comprises a propagator spacer, comprising a saturated carbon moiety, a polyethylene glycol (PEG) moiety, or a combination thereof.

24. The copolymer of claim 23, wherein the saturated carbon moiety comprises at least 2, 3, 4, 5, 6, 7, 8, 9, 10, 11, 12, 13, 14, or 15 carbons (optionally, 2 to 6 carbons).

25. The copolymer of claim 23, wherein the PEG moiety comprises 2 to 72 (OCH$_2$CH$_2$) subunits.

26. The copolymer of claim 25, wherein the PEG moiety is of a linear, branched, or star configuration.

27. The copolymer of claim 1, comprising a plurality of the propagator blocks and a plurality of the linkages, and each propagator block of the plurality of the propagator blocks connects to at least another propagator block of the propagator blocks or the initiator block via one of the plurality of the linkages.

28. The copolymer of claim 1,
wherein the propagator block is a first propagator block, the linkage is a first linkage, and the copolymer further comprises a second propagator block, connecting to the first propagator block via a second linkage;
wherein the first propagator block and the second propagator block independently comprise a guanidine group, a zwitterion group, a diethylene triamine, or a combination thereof, and
wherein the second linkage comprises a disulfide bond.

29. The copolymer of claim 28, wherein the first propagator block comprises the guanidine group, and the second propagator block comprises the zwitterion group.

30. The copolymer of claim 28, wherein the first propagator block comprises the guanidine group, and the second propagator block comprises the diethylene triamine.

31. The copolymer of claim 28, wherein the copolymer further comprises a third propagator block, wherein the third propagator block is linked to the first propagator block or the second propagator block via a third linkage comprising a disulfide bond.

32. The copolymer of claim 1, wherein the propagator block is selected from a group consisting of:

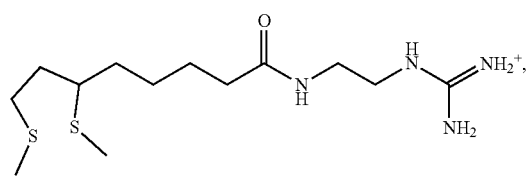

PB1

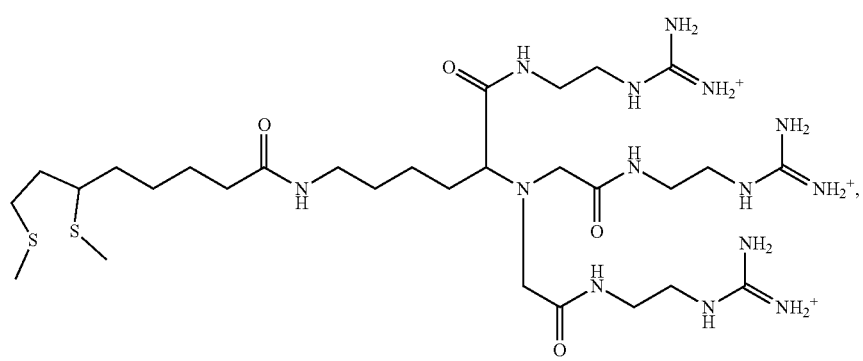

PB2

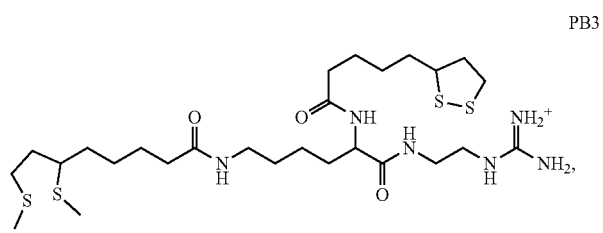

PB3

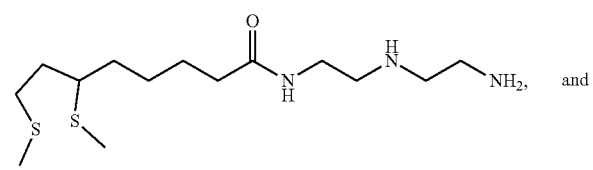

PB4 and

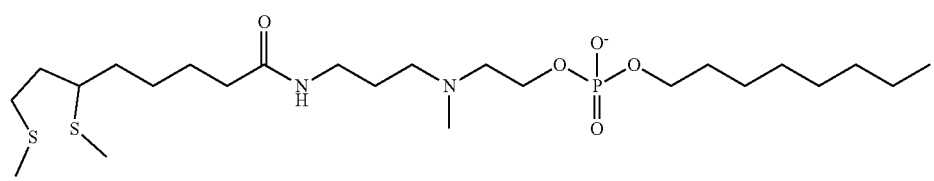

PB5

33. The copolymer of claim 32, comprising at least two propagator blocks, wherein the at least two propagator blocks are (1) PB1 and PB5, (2) PB1 and PB4, (3) PB2 and PB5, (4) PB2 and PB5, or (5) PB1, PB4, and PB5.

34. The copolymer of claim 33, wherein the initiator block is selected from a group consisting of 117
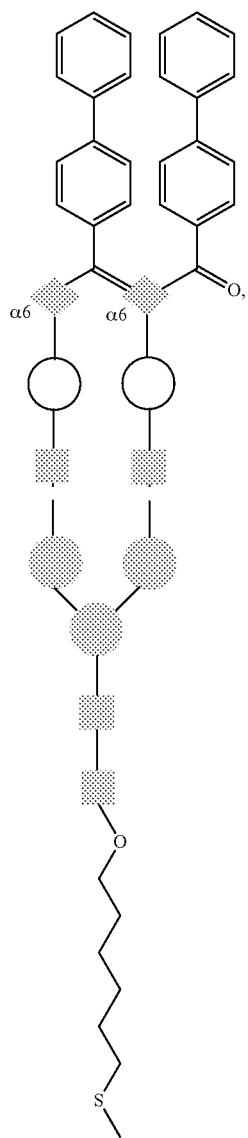
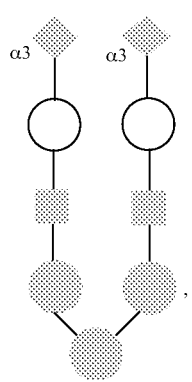
118
IB2
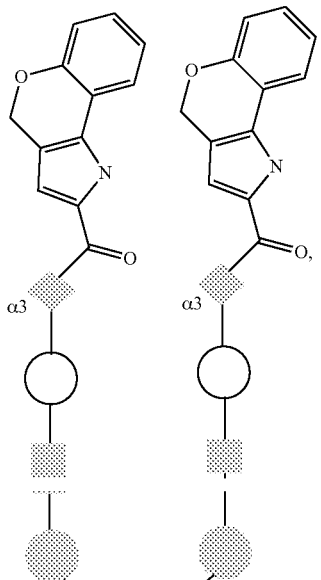
IB3

IB5
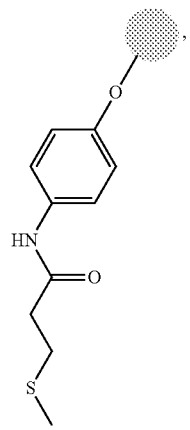
IB6
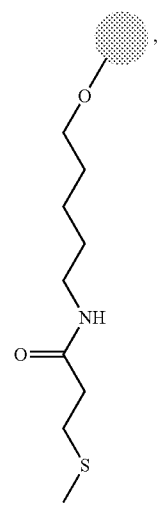
IB7
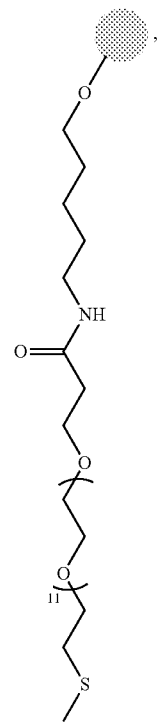
IB8
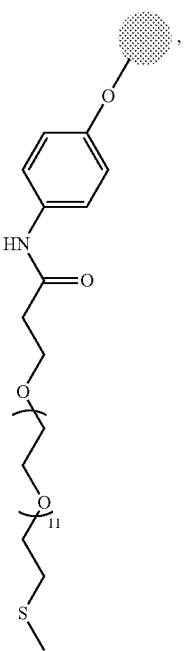
IB9
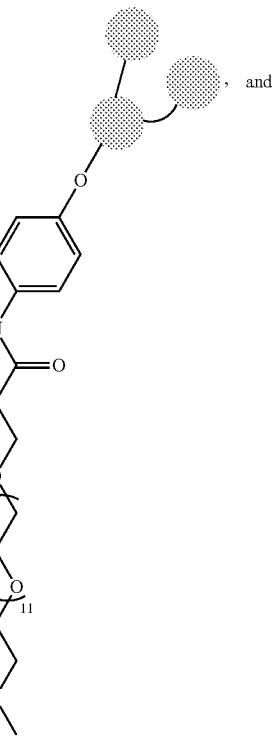, and

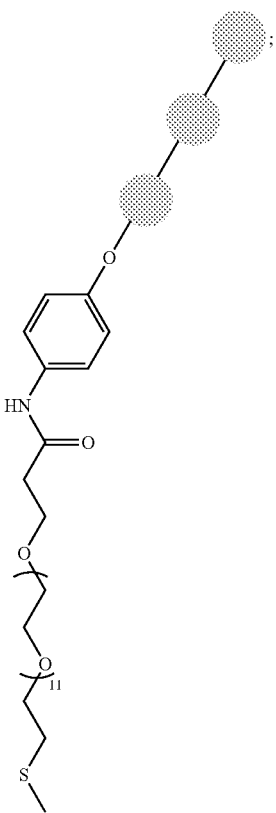

IB10 wherein the solid circle represents mannoside, the open circle represents Galactose, the solid square represents GlcNAc, and the diamond represents Neu5Ac, and wherein the initiator block and the at least two propagator block are selected from a group consisting of IB5-PB1/PB5, IB5-PB1/PB4, IB5-PB2/PB5, IB5-PB2/PB4, IB5-PB1/PB4/PB5, IB6-PB1/PB5, IB6-PB1/PB4, IB6-PB2/PB5, IB6-PB2/PB4, IB6-PB1/PB4/PB5, IB7-PB1/PB5, IB7-PB1/PB4, IB7-PB2/PB5, IB7-PB2/PB4, IB7-PB1/PB4/PB5, IB8-PB1/PB5, IB8-PB1/PB4, IB8-PB2/PB5, IB8-PB2/PB4, IB8-PB1/PB4/PB5, IB9-PB1/PB5, IB9-PB1/PB4, IB9-PB2/PB5, IB9-PB2/PB4, IB9-PB1/PB4/PBS, IB10-PB1/PBS, IB10-PB1/PB4, IB10-PB2/PBS, IB10-PB2/PB4, and IB10-PB1/PB4/PB5.

35. A polymersome, comprising a membrane defining an inner space, wherein the membrane comprises the copolymer of any one of claims 1 to 34.

36. The polymersome of claim 35, wherein the copolymer comprises at least 50%, 70%, 80%, 90%, 95%, or 99% of the membrane.

37. The polymersome of claim 35, wherein the membrane encapsulates a payload therewithin.

38. The polymersome of claim 37, wherein the payload is a nucleic acid, a compound, a polypeptide, a protein, a glycan, or a combination thereof.

39. The polymersome of claim 38, wherein the nucleic acid is RNA or DNA.

40. The polymersome of claim 39, wherein the payload encodes a polypeptide.

41. The polymersome of claim 37, wherein the payload is immunogenic, or the payload is a nucleic acid configured to encode an immunogenic polypeptide or protein.

42. The polymersome of claim 35, wherein the copolymer is a first copolymer, and the membrane further comprises a second copolymer, wherein the first copolymer and the second copolymer are independent of any one of claims 1 to 34.

43. The polymersome of claim 35, having a diameter of 0.001 to 5 microns or 0.01 to 5 microns.

44. The polymersome of claim 35, wherein the payload is a first payload, and the membrane further encapsulates a second payload.

45. The polymersome of claim 44, wherein the second payload is a nucleic acid, a compound, a polypeptide, a protein, a glycan, or a combination thereof.

46. The polymersome of claim 45, wherein the first payload and the second payload are different.

47. A formulation, comprising a polymersome of claim 35.

48. The formulation of claim 47, comprising 0.01 to 95% (w/w) of the polymersome.

49. The formulation of claim 47, wherein the polymersome is a first polymersome, and the composition further comprises a second polymersome.

50. The formulation of claim 49, wherein the first polymersome and the second polymersome are different in size, copolymers forming the membrane thereof, payload encapsulated within the polymersomes, or a combination thereof.

51. The formulation of claim 47, further comprising a pharmaceutically acceptable excipient, adjuvant, or a combination thereof.

52. The formulation of claim 51, wherein the excipient comprises a solvent, dispersion media, diluent, dispersion, suspension aid, surface active agent, isotonic agent, thickening or emulsifying agent, preservative, polymer, peptide, protein, cell, hyaluronidase, or mixtures thereof.

53. The formulation of claim 51, wherein the adjuvant comprises C34, Gluco-C34, 7DW8-5, C17, C23, C30, α-galactosylceramide, Aluminum salt, Squalene, MF59, or QS-21; other examples of adjuvants in some vaccines that can be used in the composition of the present disclosure are aluminum hydroxide, aluminum phosphate, alum (potassium aluminum sulfate), mixed aluminum salts, Freund's complete adjuvant, Freund's incomplete adjuvant, AS03, MF59, and CpG 1018, or a combination thereof.

54. A kit for preparing a polymersome, comprising:
a first reagent, comprising an initiator, wherein the initiator comprises a glycan head and an initiator linking moiety, and
a second reagent, comprising a propagator, wherein the propagator comprises a functional moiety and a propagator linking moiety, wherein the functional moiety comprises a guanidine group, a zwitterion group, a diethylene triamine, or a combination thereof, and
wherein the initiator linking moiety is configured to couple with the propagator linking moiety via a linkage comprising a disulfide bond.

55. The kit of claim 54, wherein the glycan head comprises a terminal mannoside.

56. The kit of claim 54, wherein the glycan head comprises an O-aryl mannoside.

57. The kit of claim 54, wherein the glycan head comprises a mono-mannoside, a di-mannoside, or a tri-mannoside.

58. The kit of claim 57, wherein the tri-mannoside is a linear or branched tri-mannoside.

59. The kit of claim 58, wherein the branched tri-mannoside is a α-1,3-α-1,6-trimannoside.

60. The kit of claim 54, wherein the initiator further comprises an initiator spacer, comprising a saturated carbon moiety, a polyethylene glycol (PEG) moiety, or a combination thereof.

61. The kit of claim 60, wherein the saturated carbon moiety comprises at least 2, 3, 4, 5, 6, 7, 8, 9, 10, 11, 12, 13, 14, or 15 carbons (optionally, 2 to 6 carbons).

62. The kit of claim 61, wherein the PEG moiety comprises 2 to 72 ($OCH_2CH_2$) subunits.

63. The kit of claim 62, wherein the PEG moiety is of a linear, branched, or star configuration.

64. The kit of claim 54, wherein the glycan head is configured to bind a dendritic cell.

65. The kit of claim 64, wherein the glycan head is configured to selectively bind DC-SIGN.

66. The kit of claim 65, wherein the glycan head is configured to bind DC-SIGN at a $K_D$ ranging from 5 to 8000 nM at pH 7.4.

67. The kit of claim 66, wherein the $K_D$ ranges from 5 to 500 nM at pH 7.4.

68. The kit of claim 65, wherein the glycan head is configured to bind DC-SIGN at a $K_D$ ranging from 1 to 800 nM at pH 5.

69. The kit of claim 68, wherein the $K_D$ ranges from 1 to 600 nM at pH 5.

70. The kit of claim 54, wherein the glycan head comprises a $9^{BPC}$Neu5Ac conjugated N-glycan (I2), Neu5Ac conjugated N-glycan (I3), $9^{TCC}$Neu5Ac conjugated N-glycan (I4), or a combination thereof; wherein BPC denotes biphenylcarboxyl, TCC denotes 4H-thieno[3,2-c]chromene-2-carbamoyl), and Neu5Ac denotes N-Acetylneuraminic acid.

71. The kit of claim 70, wherein the glycan head is configured to bind Siglec-2, Siglec-5/E, Siglec-1, or a combination thereof.

72. The kit of claim 54, wherein the initiator linking moiety is a thiol group or a dithiolane group.

73. The kit of claim 54, wherein the initiator is selected from a group consisting of:

I2

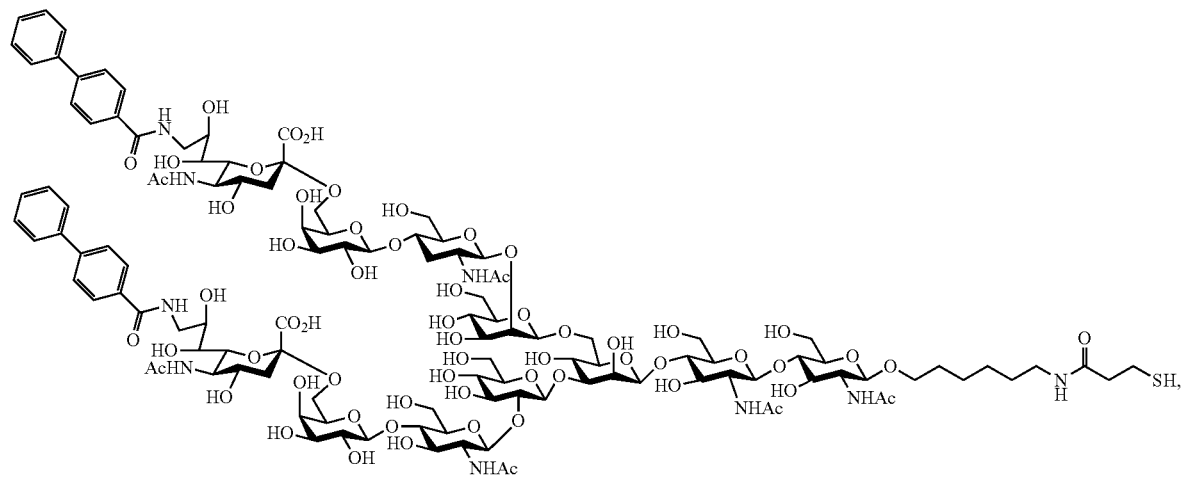

I3

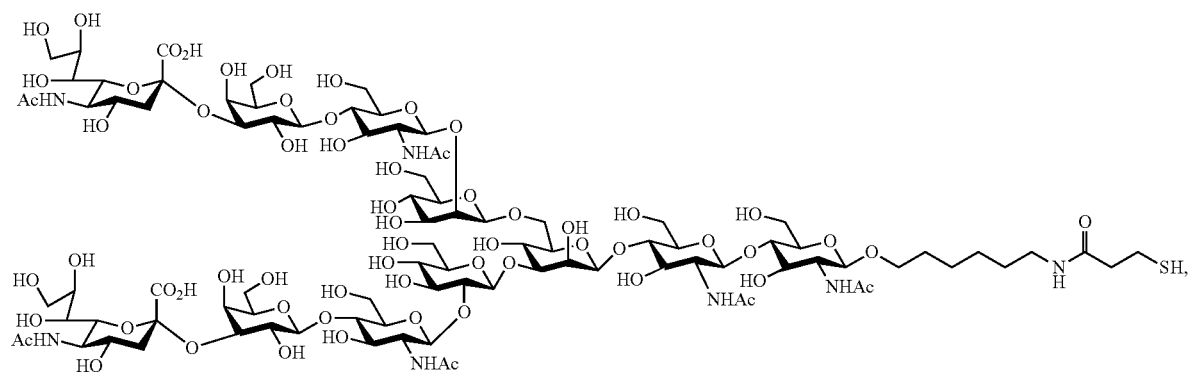

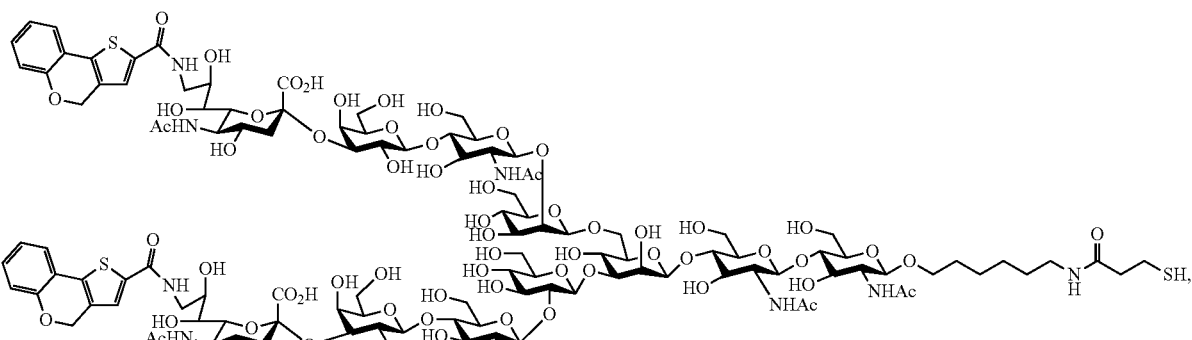
I4
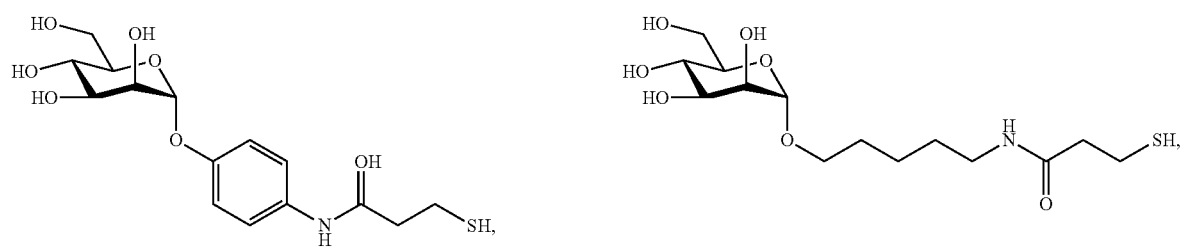
I5
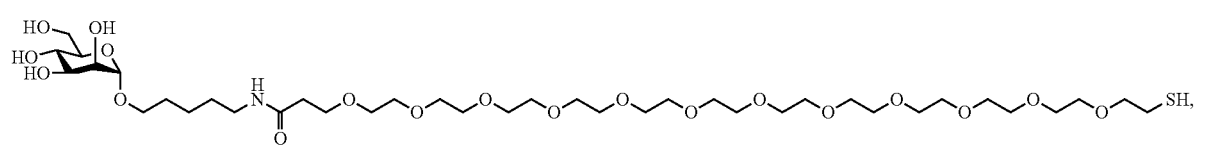
I6
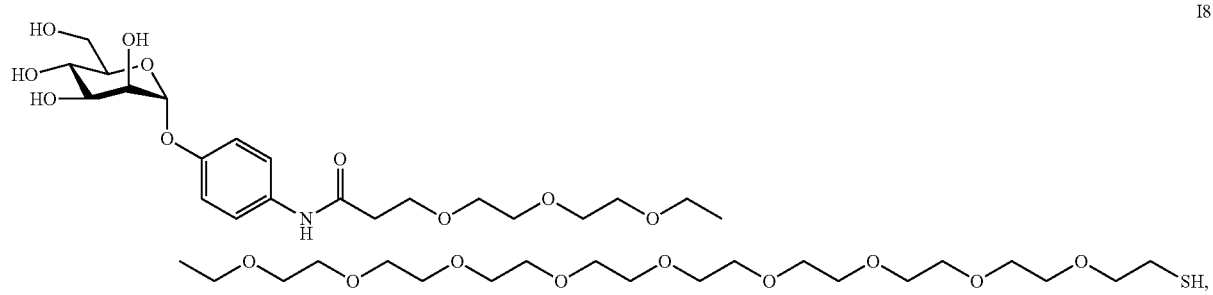
I7
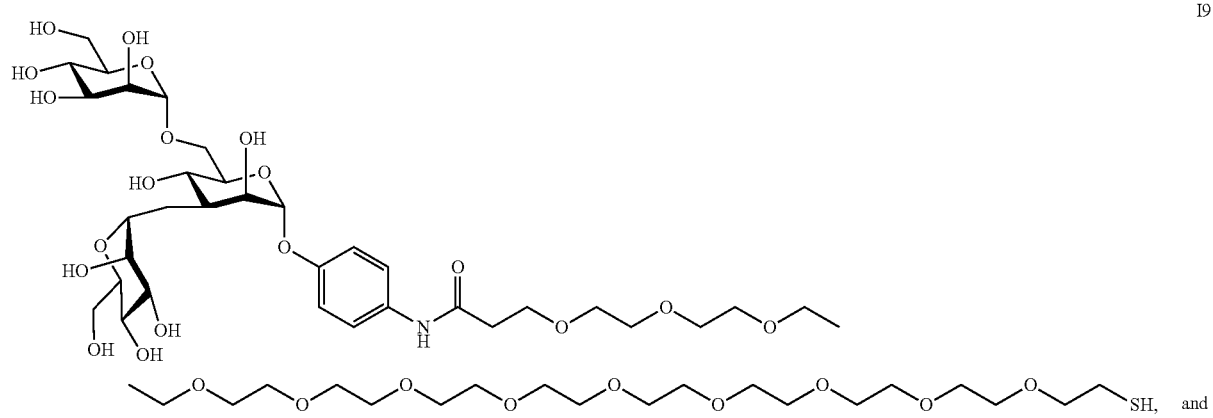
I8
I9
and

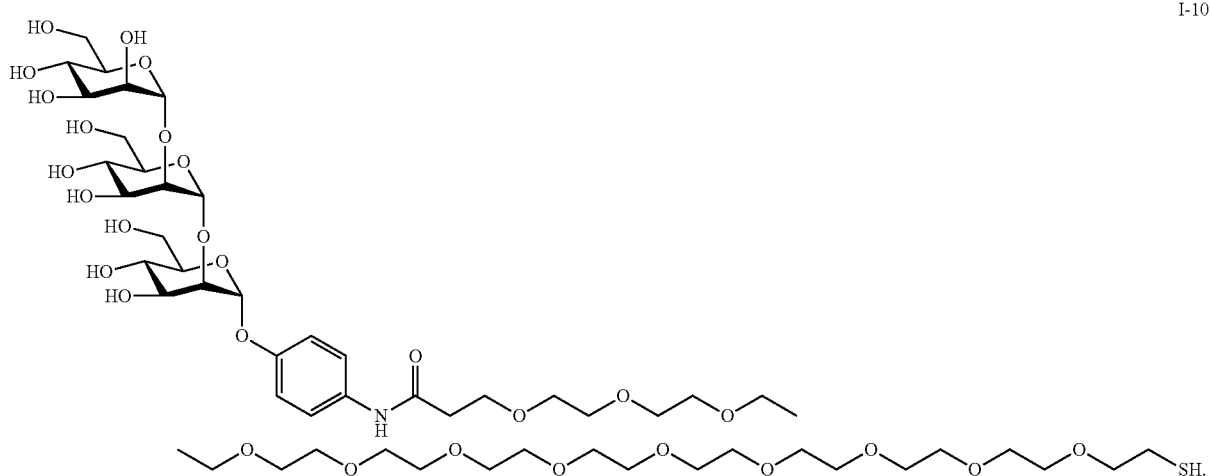

I-10

74. The kit of claim 54, wherein the propagator comprises more than one guanidine group.

75. The kit of claim 74, wherein the propagator comprises three guanidine groups.

76. The kit of claim 54, wherein the propagator further comprises a propagator spacer, comprising a saturated carbon moiety, a polyethylene glycol (PEG) moiety, or a combination thereof.

77. The kit of claim 76, wherein the saturated carbon moiety comprises at least 2, 3, 4, 5, 6, 7, 8, 9, 10, 11, 12, 13, 14, or 15 carbons (optionally, 2 to 6 carbons).

78. The kit of claim 76, wherein the PEG moiety comprises 2 to 72 ($OCH_2CH_2$) subunits.

79. The kit of claim 78, wherein the PEG moiety is a linear PEG.

80. The kit of claim 54,
wherein the propagator of the second reagent is a first propagator, and wherein the second reagent further comprises a second propagator, or the kit further comprises a third reagent comprising the second propagator; and
wherein the first propagator and the second propagator independently comprise a functional moiety comprising a guanidine group, a zwitterion group, a diethylene triamine, or a combination thereof.

81. The kit of claim 80, wherein the first propagator comprises the guanidine group, and the second propagator comprises the zwitterion group.

82. The kit of claim 80, wherein the first propagator comprises the guanidine group, and the second propagator comprises the diethylene triamine.

83. The kit of claim 54, wherein the propagator linking moiety is a thiol group or a dithiolane group.

84. The kit of claim 54, wherein the propagator is selected from a group consisting of:

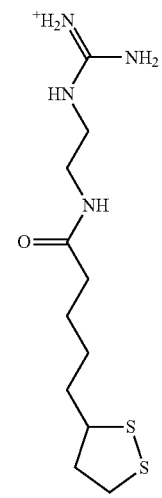

P1

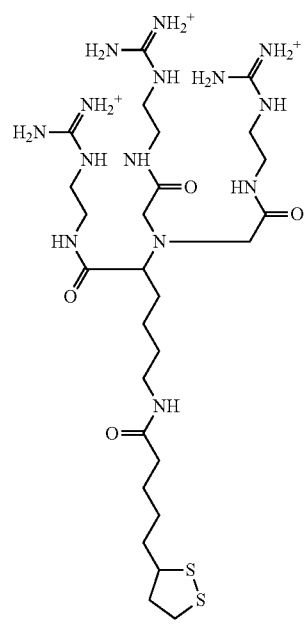

P2

P3

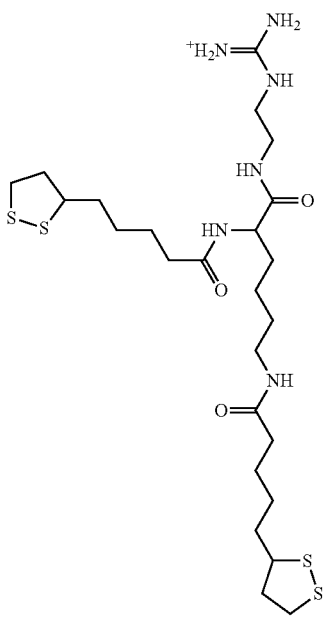

P4

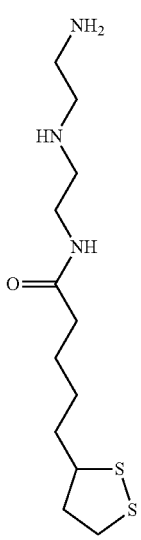

P5

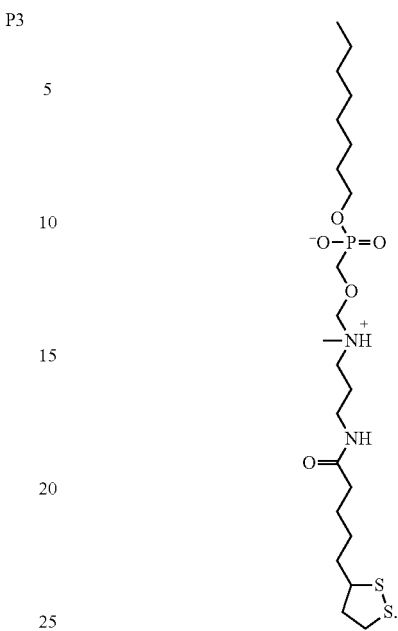

85. The kit of claim 54, wherein the first reagent and the second reagent are contained in the same container.

86. The kit of claim 54, wherein the first reagent and the second reagent are contained in separate containers.

87. The kit of claim 54, further comprising a payload, wherein the payload is a nucleic acid, a compound, a polypeptide, a protein, a glycan, or a combination thereof.

88. The kit of claim 87, wherein the nucleic acid is RNA or DNA.

89. The kit of claim 88, wherein the payload encodes a polypeptide.

90. The kit of claim 87, wherein the payload is immunogenic, or the payload is a nucleic acid configured to encode an immunogenic polypeptide or protein.

91. A method of targeted delivering a payload in a subject, comprising administering to the subject an effective amount of a pharmaceutical formulation comprising a polymersome, wherein the polymersome comprises a membrane encapsulating the payload, and wherein the membrane comprises a copolymer of any one of claims 1 to 34.

92. The method of claim 91, wherein the copolymer comprises at least 50%, 70%, 80%, 90%, 95%, or 99% of the membrane.

93. The method of claim 92, wherein the copolymer is a first copolymer, and the membrane further comprises a second copolymer, wherein the first copolymer and the second copolymer are independently of any one of claims 1 to 34.

94. The method of claim 91, wherein the payload is a nucleic acid, a compound, a peptide, a protein, a glycan, or a combination thereof.

95. The method of claim 94, wherein the nucleic acid is RNA or DNA.

96. The method of claim 95, wherein the payload encodes a polypeptide.

97. The method of claim 91, wherein the payload is immunogenic, or the payload is a nucleic acid configured to encode an immunogenic polypeptide or protein.

98. The method of claim 91, wherein the payload is a first payload, and the membrane further encapsulates a second payload.

99. The method of claim 98, wherein the second payload is a nucleic acid, a compound, a polypeptide, a protein, a glycan, or a combination thereof.

100. The method of claim 99, wherein the first payload and the second payload are different.

101. A method of preventing or treating a disease in a subject, comprising administering to the subject an effective amount of a pharmaceutical formulation comprising a polymersome,
wherein the polymersome comprises a membrane, wherein the membrane comprises the polymeric component of any one of claims 1 to 34; and a payload, encapsulated within the membrane; and
wherein the payload is a therapeutic agent or derives a therapeutic agent.

102. The method of claim 101, wherein the polymeric component comprises at least 50%, 70%, 80%, 90%, 95%, or 99% of the membrane.

103. The method of claim 101, wherein the payload is a nucleic acid, a compound, a peptide, a protein, a glycan, or a combination thereof.

104. The method of claim 103, wherein nucleic acid is RNA or DNA.

105. The method of claim 104, wherein the payload encodes a polypeptide.

106. The method of claim 101, wherein the payload is a first payload, and the membrane further encapsulates a second payload.

107. The method of claim 106, wherein the second payload is a nucleic acid, a compound, a polypeptide, a protein, a glycan, or a combination thereof.

108. The method of claim 107, wherein the first payload and the second payload are different.

109. The method of claim 101, wherein the polymersome is administered in an initial dose and followed by one, two, three, four, five, or more booster doses.

110. The method of claim 109, wherein the booster doses are administered about one month, about two months, about three months, about four months, about five months, or about six months or more following the initial dose.

111. The method of claim 101, wherein the effective amount ranges from about 5 µg to 1000 µg.

112. A method of boosting an adaptive immune response, comprising administering to a subject an effective amount of an effective amount of a pharmaceutical formulation comprising a polymersome;
wherein the polymersome comprises a membrane encapsulating the payload, and
wherein the membrane comprises a copolymer of any one of claims 1 to 34;
wherein the payload is immunogenic or derives an immunogenic biomolecule.

113. The method of claim 112, wherein the polymeric component comprises at least 50%, 70%, 80%, 90%, 95%, or 99% of the membrane.

114. The method of claim 112, wherein the payload is a nucleic acid, a compound, a peptide, a protein, a glycan, or a combination thereof.

115. The method of claim 114, wherein nucleic acid is RNA or DNA.

116. The method of claim 112, wherein the biomolecule is a polypeptide or a protein.

117. The method of claim 112, wherein the payload is a first payload, and the membrane further encapsulates a second payload.

118. The method of claim 117, wherein the second payload is a nucleic acid, a compound, a polypeptide, a protein, a glycan, or a combination thereof.

119. The method of claim 118, wherein the first payload and the second payload are different.

120. The method of claim 112, wherein the polymersome is administered in an initial dose followed by one, two, three, four, five, or more booster doses.

121. The method of claim 120, wherein the booster doses are administered about one month, about two months, about three months, about four months, about five months, or about six months or more following the initial dose.

122. The method of claim 112, wherein the effective amount ranges from about 5 µg to 1000 µg.

* * * * *